US011781160B2

(12) United States Patent
Disley et al.

(10) Patent No.: US 11,781,160 B2
(45) Date of Patent: Oct. 10, 2023

(54) METHODS FOR THE PRODUCTION OF METHACRYLATES

(71) Applicant: Mitsubishi Chemical UK Limited, Billingham (GB)

(72) Inventors: Zoe Disley, Nottingham (GB); Graham Ronald Eastham, Redcar (GB); David William Johnson, Redcar (GB); Laura Martins, Nottingham (GB); Russel Menchavez, Nottingham (GB); Luca Rossoni, Nottingham (GB); Gill Stephens, Nottingham (GB)

(73) Assignee: Mitsubishi Chemical UK Limited, Billingham (GB)

( * ) Notice: Subject to any disclaimer, the term of this patent is extended or adjusted under 35 U.S.C. 154(b) by 57 days.

(21) Appl. No.: 17/057,051

(22) PCT Filed: May 23, 2019

(86) PCT No.: PCT/GB2019/051427
§ 371 (c)(1),
(2) Date: Nov. 19, 2020

(87) PCT Pub. No.: WO2019/224548
PCT Pub. Date: Nov. 28, 2019

(65) Prior Publication Data
US 2021/0207177 A1 Jul. 8, 2021

(30) Foreign Application Priority Data
May 23, 2018 (GB) ...................... 1808424

(51) Int. Cl.
*C12P 7/62* (2022.01)
*C12N 1/38* (2006.01)
*C12N 15/70* (2006.01)

(52) U.S. Cl.
CPC .................. *C12P 7/62* (2013.01); *C12N 1/38* (2013.01); *C12N 15/70* (2013.01)

(58) Field of Classification Search
CPC ...................................................... C12P 7/62
See application file for complete search history.

(56) References Cited

U.S. PATENT DOCUMENTS

2013/0065279 A1  3/2013  Burk et al.

FOREIGN PATENT DOCUMENTS

| CA | 2688292 A1 | 12/2008 | |
| EP | 2894224 A1 | 7/2015 | |
| KR | 20140018787 A | 2/2014 | |
| RU | 2491346 C2 | 8/2013 | |
| WO | 2015031653 A2 | 3/2015 | |
| WO | 2016185211 A1 | 11/2016 | |
| WO | WO-2018096326 A1 * | 5/2018 | ............... C12N 9/00 |

OTHER PUBLICATIONS

Studer. Residue mutations and their impact on protein structure and function: detecting beneficial and pathogenic changes. Biochem. J. (2013) 449, 581-594.*
Koutsolioutsou. Constitutive soxR mutations contribute to multiple-antibiotic resistance in clinical *Escherichia coli* isolates. Antimicrob Agents Chemother. Jul. 2005;49(7):2746-52.*
"International Preliminary Report on Patentability corresponding to International Application No. PCT/GB2019/051427 dated Nov. 24, 2020".
"International Search Report and Written Opinion corresponding to International Application No. PCT/GB2019/051427 dated Dec. 13, 2019".
Alekshun, Michael N., et al., "Characterization of marR Super-repressor Mutants", Journal of Bacteriology 181(10):3303-3306 (May 15, 1999).
Aono, Rikizo , et al., "Involvement of Outer Membrane Protein TolC, a Possible Member of the mar-sox Reguion, in Maintenance and Improvement of Organic Solvent Tolerance of *Escherichia coli* K-12", Journal of Bacteriology 180(4):938-944 (Feb. 1, 1998).
Curson, Andrew R.J., et al., "Screening of Metagenomic and Genomic Libraries Reveals Three Classes of Bacterial Enzymes That Overcome the Toxicity of Acrylate", PLOS One 9(5):e97660 (May 21, 2014) (13 pages).
Disley, Zoe B.C., "Towards the bioproduction of methyl methacrylate: solving the problem of product toxicity", PhD Thesis, The University of Nottingham (Jul. 2018) (Abstract) Retrieved from Internet URL:https://eprints.nottingham.ac.uk/48281/ [retrieved Aug. 26, 2019].
Oh, Hye Yun, et al., "Increase of organic solvent tolerance of *Escherichia coli* by the deletion of two regulator genes, fadR and marR", Appl. Microbiol. Biotechnol. 96(6):1619-1627 (Oct. 10, 2012).
Schellhorn, Herb E., et al., "Regulators of oxidative stress response genes in *Escherichia coli* and their conservation in bacteria", Chapter 10.5 Stress and Environmental Regulation of Gene Expression and Adaptation in Bacteria pp. 632-637 (Aug. 12, 2016).
Sun, Jingjing , et al., "Bacterial multidrug efflux pumps: Mechanisms, physiology and pharmacological exploitations", Biochemical and Biophysical Research Communications 453(2):254-267 (May 27, 2014).
Watanabe, Rei , et al., "Contributions of mutations in acrR and marR genes to organic solvent tolerance in *Escherichia ecoli*", AMB Express 2(58):1-11 (Jan. 1, 2012).
"Combined Search and Examination Report corresponding to British Application No. GB1808424.4 dated Jul. 31, 2018".
Broun , et al., "Catalytic Plasticity of Fatty Acid Modification Enzymes Underlying Chemical Diversity of Plant Lipids", Science 282:315-1317 (1998).
Seffernick, J L, et al., "Melamine deaminase and atrazine chlorohydrolase: 98 percent identical but functionally different", J. Bacteriol. 183(8):2405-2410 (Jan. 22, 2001).

(Continued)

*Primary Examiner* — Yong D Pak
(74) *Attorney, Agent, or Firm* — Myers Bigel, P.A.

(57) ABSTRACT

The invention relates to methods for the production of methacrylates using methacrylate tolerant microorganisms.

9 Claims, 8 Drawing Sheets

Figure 1:
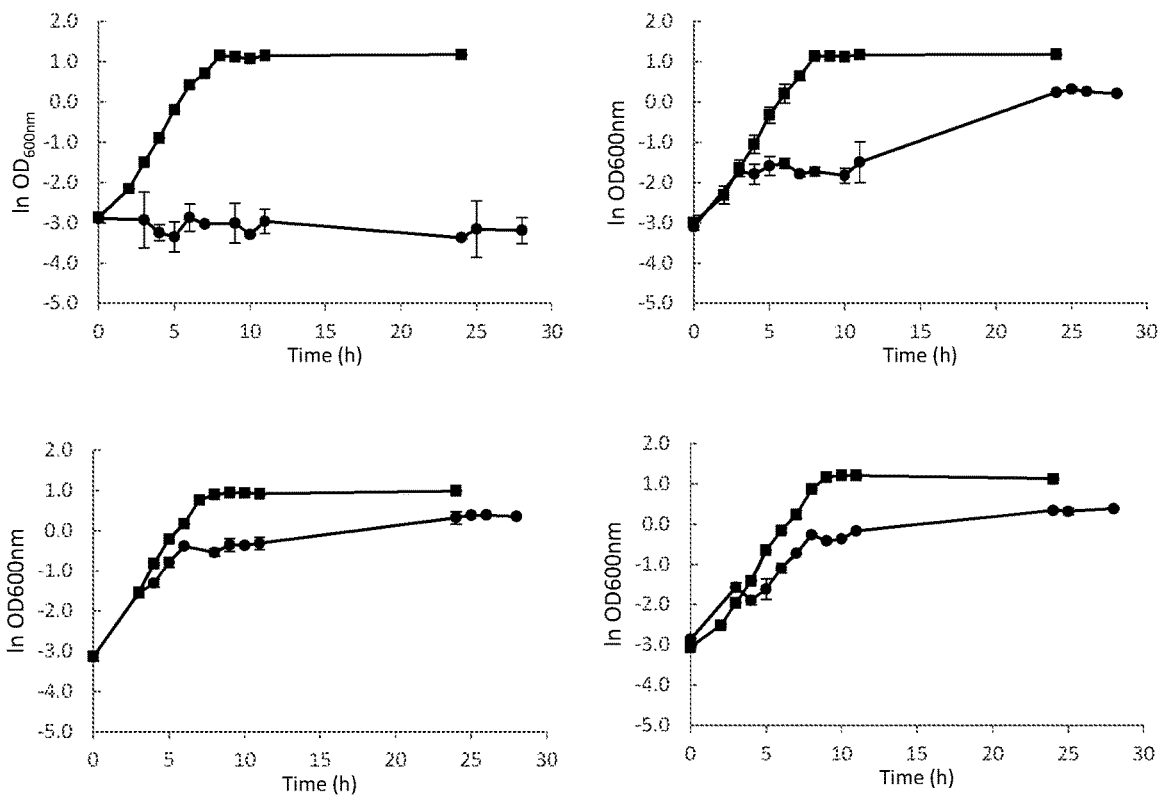

Specification includes a Sequence Listing.

(56) References Cited

OTHER PUBLICATIONS

Whisstock, James C, et al., "Prediction of protein function from protein sequence and structure", Q Rev Biophys. 36(3):307-40 (Aug. 2003).
Witkowski, A , et al., "Conversion of a beta ketoacyl synthase to a malonyl decarboxylase by replacement of the active site cysteine with glutamine", Biochemistry 38:11643-11650 (1999).
"The Ecetoc scheme for the joint assessment of commodity chemicals", Joint Assessment of Commodity Chemicals No. 36 (Dec. 1996) 84 pages.

\* cited by examiner

SEQUENCE LISTING

<160> NUMBER OF SEQ ID NOS: 33

<210> SEQ ID NO 1
<211> LENGTH: 465
<212> TYPE: DNA
<213> ORGANISM: Escherichia coli

<400> SEQUENCE: 1

| | | | | | |
|---|---|---|---|---|---|
| atggaaaaga | aattacccg | cattaaagcg | ctgctaaccc | ccggcgaagt | ggcgaaacgc | 60 |
| agcggtgtgg | cggtatcggc | gctgcatttc | tatgaaagta | aagggttgat | taccagtatc | 120 |
| cgtaacagcg | gcaatcagcg | gcgatataaa | cgtgatgtgt | tgcgatatgt | tgcaattatc | 180 |
| aaaattgctc | agcgtattgg | cattccgctg | gcgaccattg | gtgaagcgtt | tggcgtgttg | 240 |
| cccgaagggc | atacgttaag | tgcgaaagag | tggaaacagc | tttcgtccca | atggcgagaa | 300 |
| gagttggatc | ggcgcattca | taccttagtg | gcgctgcgtg | acgaactgga | cggatgtatt | 360 |
| ggttgtggct | gcctttcgcg | cagtgattgc | ccgttgcgta | acccgggcga | ccgcttagga | 420 |
| gaagaaggta | ccggcgcacg | cttgctggaa | gatgaacaaa | actaa | | 465 |

<210> SEQ ID NO 2
<211> LENGTH: 154
<212> TYPE: PRT
<213> ORGANISM: Escherichia coli

<400> SEQUENCE: 2

Met Glu Lys Lys Leu Pro Arg Ile Lys Ala Leu Leu Thr Pro Gly Glu
1               5                   10                  15

Val Ala Lys Arg Ser Gly Val Ala Val Ser Ala Leu His Phe Tyr Glu
            20                  25                  30

Ser Lys Gly Leu Ile Thr Ser Ile Arg Asn Ser Gly Asn Gln Arg Arg
        35                  40                  45

Tyr Lys Arg Asp Val Leu Arg Tyr Val Ala Ile Ile Lys Ile Ala Gln
    50                  55                  60

Arg Ile Gly Ile Pro Leu Ala Thr Ile Gly Glu Ala Phe Gly Val Leu
65                  70                  75                  80

Pro Glu Gly His Thr Leu Ser Ala Lys Glu Trp Lys Gln Leu Ser Ser
                85                  90                  95

Gln Trp Arg Glu Glu Leu Asp Arg Arg Ile His Thr Leu Val Ala Leu
            100                 105                 110

Arg Asp Glu Leu Asp Gly Cys Ile Gly Cys Gly Cys Leu Ser Arg Ser
        115                 120                 125

Asp Cys Pro Leu Arg Asn Pro Gly Asp Arg Leu Gly Glu Glu Gly Thr
    130                 135                 140

Gly Ala Arg Leu Leu Glu Asp Glu Gln Asn
145                 150

<210> SEQ ID NO 3
<211> LENGTH: 648
<212> TYPE: DNA
<213> ORGANISM: Escherichia coli

<400> SEQUENCE: 3

| | | | | | |
|---|---|---|---|---|---|
| atggcacgaa | aaaccaaaca | agaagcgcaa | gaaacgcgcc | aacacatcct | cgatgtggct | 60 |
| ctacgtcttt | tctcacagca | gggggtatca | tccacctcgc | tgggcgagat | tgcaaaagca | 120 |
| gctggcgtta | cgcgcggtgc | aatctactgg | catttaaag | acaagtcgga | tttgttcagt | 180 |
| gagatctggg | aactgtcaga | atccaatatt | ggtgaactag | agcttgagta | tcaggcaaaa | 240 |

```
ttccctggcg atccactctc agtattaaga gagatattaa ttcatgttct tgaatccacg    300
gtgacagaag aacggcgtcg attattgatg gagattatat tccacaaatg cgaatttgtc    360
ggagaaatgg ctgttgtgca acaggcacaa cgtaatctct gtctggaaag ttatgaccgt    420
atagaacaaa cgttaaaaca ttgtattgaa gcgaaaatgt tgcctgcgga tttaatgacg    480
cgtcgcgcag caattattat gcgcggctat atttccggcc tgatggaaaa ctggctcttt    540
gccccgcaat cttttgatct taaaaaagaa gcccgcgatt acgttgccat cttactggag    600
atgtatctcc tgtgccccac gcttcgtaat cctgccacta cgaataa                 648

<210> SEQ ID NO 4
<211> LENGTH: 215
<212> TYPE: PRT
<213> ORGANISM: Escherichia coli

<400> SEQUENCE: 4

Met Ala Arg Lys Thr Lys Gln Glu Ala Gln Glu Thr Arg Gln His Ile
1               5                   10                  15

Leu Asp Val Ala Leu Arg Leu Phe Ser Gln Gln Gly Val Ser Ser Thr
                20                  25                  30

Ser Leu Gly Glu Ile Ala Lys Ala Ala Gly Val Thr Arg Gly Ala Ile
            35                  40                  45

Tyr Trp His Phe Lys Asp Lys Ser Asp Leu Phe Ser Glu Ile Trp Glu
        50                  55                  60

Leu Ser Glu Ser Asn Ile Gly Glu Leu Glu Leu Glu Tyr Gln Ala Lys
65                  70                  75                  80

Phe Pro Gly Asp Pro Leu Ser Val Leu Arg Glu Ile Leu Ile His Val
                85                  90                  95

Leu Glu Ser Thr Val Thr Glu Glu Arg Arg Arg Leu Leu Met Glu Ile
                100                 105                 110

Ile Phe His Lys Cys Glu Phe Val Gly Glu Met Ala Val Val Gln Gln
            115                 120                 125

Ala Gln Arg Asn Leu Cys Leu Glu Ser Tyr Asp Arg Ile Glu Gln Thr
        130                 135                 140

Leu Lys His Cys Ile Glu Ala Lys Met Leu Pro Ala Asp Leu Met Thr
145                 150                 155                 160

Arg Arg Ala Ala Ile Ile Met Arg Gly Tyr Ile Ser Gly Leu Met Glu
                165                 170                 175

Asn Trp Leu Phe Ala Pro Gln Ser Phe Asp Leu Lys Lys Glu Ala Arg
                180                 185                 190

Asp Tyr Val Ala Ile Leu Leu Glu Met Tyr Leu Leu Cys Pro Thr Leu
            195                 200                 205

Arg Asn Pro Ala Thr Asn Glu
        210                 215

<210> SEQ ID NO 5
<211> LENGTH: 867
<212> TYPE: DNA
<213> ORGANISM: Escherichia coli

<400> SEQUENCE: 5
acgacggatc ggaatcagca gttcacagcg tagattaatt gggcgatctc ccgctttggc    60
atcttctgcc gggtagtatc gctcaatatc ctgacctta cggcgcgtca ggttgagcat    120
tggcatgcac gttccgtata ccgtcaggat aaactcctgc acgccggttc ccagaccttc    180
```

```
ataggtaaac atcacatatt cgccgccctg cagcatcacc ggatgccccg tcagtacata    240
gccatctgcc tgatcctggg ctaacgcggt ggtatagaat acctcttgct cgtcgtcttt    300
atcctgactc ggacgcgttt cattcaggcc gtagagcacc ggcggaatgg tcggcgcgtt    360
gccgagaaaa tcgtgccaga actgataacg catttcatgg cggaaatcag agatttgctc    420
cagcgaacag gagtagctct gggtaacacc aatcagcggc gtatcttcca gggtgacaaa    480
tttgtgctct ggcatagtga attcacccag gcgtagcggc gggcgaatac caaaggcgct    540
ccattcagga gaacggcggt aaagtgcagg agtctgggca aactgcttct tgaatgcgcg    600
ggtaaatgtc tgttgagagt cgaagcggta ttgcagcgcg atgtccagaa tcggacgcgc    660
agtcaggcgt agtgcgaccg ccgatttcga caaacgacga gcacgaatat acgcgccaat    720
agcatggcca gtgacatctt taaacattct ctgtaagtgc acttggaat aacctgcttt     780
cgccgctaca ttgtcgagcg acaggggctg atccagatga ccttccagcc agattaaaag    840
gtcgcgaata atgccggcct gatccat                                        867
```

<210> SEQ ID NO 6
<211> LENGTH: 289
<212> TYPE: PRT
<213> ORGANISM: Escherichia coli

<400> SEQUENCE: 6

```
Met Asp Gln Ala Gly Ile Ile Arg Asp Leu Leu Ile Trp Leu Glu Gly
1               5                   10                  15

His Leu Asp Gln Pro Leu Ser Leu Asp Asn Val Ala Ala Lys Ala Gly
            20                  25                  30

Tyr Ser Lys Trp His Leu Gln Arg Met Phe Lys Asp Val Thr Gly His
        35                  40                  45

Ala Ile Gly Ala Tyr Ile Arg Ala Arg Arg Leu Ser Lys Ser Ala Val
    50                  55                  60

Ala Leu Arg Leu Thr Ala Arg Pro Ile Leu Asp Ile Ala Leu Gln Tyr
65                  70                  75                  80

Arg Phe Asp Ser Gln Gln Thr Phe Thr Arg Ala Phe Lys Lys Gln Phe
                85                  90                  95

Ala Gln Thr Pro Ala Leu Tyr Arg Arg Ser Pro Glu Trp Ser Ala Phe
            100                 105                 110

Gly Ile Arg Pro Pro Leu Arg Leu Gly Glu Phe Thr Met Pro Glu His
        115                 120                 125

Lys Phe Val Thr Leu Glu Asp Thr Pro Leu Ile Gly Val Thr Gln Ser
    130                 135                 140

Tyr Ser Cys Ser Leu Glu Gln Ile Ser Asp Phe Arg His Glu Met Arg
145                 150                 155                 160

Tyr Gln Phe Trp His Asp Phe Leu Gly Asn Ala Pro Thr Ile Pro Pro
                165                 170                 175

Val Leu Tyr Gly Leu Asn Glu Thr Arg Pro Ser Gln Asp Lys Asp Asp
            180                 185                 190

Glu Gln Glu Val Phe Tyr Thr Thr Ala Leu Ala Gln Asp Gln Ala Asp
        195                 200                 205

Gly Tyr Val Leu Thr Gly His Pro Val Met Leu Gln Gly Gly Glu Tyr
    210                 215                 220

Val Met Phe Thr Tyr Glu Gly Leu Gly Thr Gly Val Gln Glu Phe Ile
225                 230                 235                 240

Leu Thr Val Tyr Gly Thr Cys Met Pro Met Leu Asn Leu Thr Arg Arg
                245                 250                 255
```

```
Lys Gly Gln Asp Ile Glu Arg Tyr Tyr Pro Ala Glu Asp Ala Lys Ala
            260                 265                 270

Gly Asp Arg Pro Ile Asn Leu Arg Cys Glu Leu Leu Ile Pro Ile Arg
        275                 280                 285

Arg

<210> SEQ ID NO 7
<211> LENGTH: 432
<212> TYPE: DNA
<213> ORGANISM: Escherichia coli

<400> SEQUENCE: 7
gtgaaaagta ccagcgatct gttcaatgaa attattccat tgggtcgctt aatccatatg    60
gttaatcaga agaaagatcg cctgcttaac gagtatctgt ctccgctgga tattaccgcg   120
gcacagttta aggtgctctg ctctatccgc tgcgcggcgt gtattactcc ggttgaactg   180
aaaaaggtat tgtcggtcga cctgggagca ctgacccgta tgctggatcg cctggtctgt   240
aaaggctggg tggaaaggtt gccgaacccg aatgacaagc gcggcgtact ggtaaaactt   300
accaccggcg gcgcggcaat atgtgaacaa tgccatcaat tagttggcca ggacctgcac   360
caagaattaa caaaaaacct gacggcggac gaagtggcaa cacttgagta tttgcttaag   420
aaagtcctgc cg                                                       432

<210> SEQ ID NO 8
<211> LENGTH: 144
<212> TYPE: PRT
<213> ORGANISM: Escherichia coli

<400> SEQUENCE: 8

Met Lys Ser Thr Ser Asp Leu Phe Asn Glu Ile Ile Pro Leu Gly Arg
1               5                   10                  15

Leu Ile His Met Val Asn Gln Lys Lys Asp Arg Leu Leu Asn Glu Tyr
            20                  25                  30

Leu Ser Pro Leu Asp Ile Thr Ala Ala Gln Phe Lys Val Leu Cys Ser
        35                  40                  45

Ile Arg Cys Ala Ala Cys Ile Thr Pro Val Glu Leu Lys Lys Val Leu
    50                  55                  60

Ser Val Asp Leu Gly Ala Leu Thr Arg Met Leu Asp Arg Leu Val Cys
65                  70                  75                  80

Lys Gly Trp Val Glu Arg Leu Pro Asn Pro Asn Asp Lys Arg Gly Val
                85                  90                  95

Leu Val Lys Leu Thr Thr Gly Gly Ala Ala Ile Cys Glu Gln Cys His
            100                 105                 110

Gln Leu Val Gly Gln Asp Leu His Gln Glu Leu Thr Lys Asn Leu Thr
        115                 120                 125

Ala Asp Glu Val Ala Thr Leu Glu Tyr Leu Leu Lys Lys Val Leu Pro
    130                 135                 140

<210> SEQ ID NO 9
<211> LENGTH: 3150
<212> TYPE: DNA
<213> ORGANISM: Escherichia coli

<400> SEQUENCE: 9
atgcctaatt tctttatcga tcgcccgatt tttgcgtggg tgatcgccat tatcatcatg    60
ttggcagggg ggctggcgat cctcaaactg ccggtggcgc aatatcctac gattgcaccg   120
```

```
ccggcagtaa cgatctccgc ctcctacccc ggcgctgatg cgaaaacagt gcaggacacg    180
gtgacacagg ttatcgaaca gaatatgaac ggtatcgata acctgatgta catgtcctct    240
aacagtgact ccacgggtac cgtgcagatc accctgacct ttgagtctgg tactgatgcg    300
gatatcgcgc aggttcaggt gcagaacaaa ctgcagctgg cgatgccgtt gctgccgcaa    360
gaagttcagc agcaaggggt gagcgttgag aaatcatcca gcagcttcct gatggttgtc    420
ggcgttatca acaccgatgg caccatgacg caggaggata tctccgacta cgtggcggcg    480
aatatgaaag atgccatcag ccgtacgtcg ggcgtgggtg atgttcagtt gttcggttca    540
cagtacgcga tgcgtatctg gatgaacccg aatgagctga acaaattcca gctaacgccg    600
gttgatgtca ttaccgccat caaagcgcag aacgcccagg ttgcggcggg tcagctcggt    660
ggtacgccgc cggtgaaagg ccaacagctt aacgcctcta ttattgctca gacgcgtctg    720
acctctactg aagagttcgg caaaatcctg ctgaaagtga atcaggatgg ttcccgcgtg    780
ctgctgcgtg acgtcgcgaa gattgagctg ggtggtgaga actacgacat catcgcagag    840
tttaacggcc aaccggcttc cggtctgggg atcaagctgg cgaccggtgc aaacgcgctg    900
gataccgctg cggcaatccg tgctgaactg gcgaagatgg aaccgttctt cccgtcgggt    960
ctgaaaattg tttacccata cgacaccacg ccgttcgtga aaatctctat tcacgaagtg   1020
gttaaaacgc tggtcgaagc gatcatcctc gtgttcctgg ttatgtatct gttcctgcag   1080
aacttccgcg cgacgttgat tccgaccatt gccgtaccgg tggtattgct cgggacccttt  1140
gccgtccttg ccgcctttgg cttctcgata aacacgctaa caatgttcgg gatggtgctc   1200
gccatcggcc tgttggtgga tgacgccatc gttgtggtag aaaacgttga gcgtgttatg   1260
gcggaagaag gtttgccgcc aaaagaagct acccgtaagt cgatggggca gattcagggc   1320
gctctggtcg gtatcgcgat ggtactgtcg gcggtattcg taccgatggc cttcttggc    1380
ggttctactg gtgctatcta tcgtcagttc tctattacca ttgtttcagc aatggcgctg   1440
tcggtactgg tggcgttgat cctgactcca gctctttgtg ccaccatgct gaaaccgatt   1500
gccaaaggcg atcacgggga aggtaaaaaa ggcttcttcg gctggtttaa ccgcatgttc   1560
gagaagagca cgcaccacta caccgacagc gtaggcggta ttctgcgcag tacggggcgt   1620
tacctggtgc tgtatctgat catcgtggtc ggcatggcct atctgttcgt gcgtctgcca   1680
agctccttct tgccagatga ggaccagggc gtgtttatga ccatggttca gctgccagca   1740
ggtgcaacgc aggaacgtac acagaaagtg ctcaatgagg taacgcatta ctatctgacc   1800
aaagaaaaga caacgttga gtcggtgttc gccgttaacg gcttcggctt tgcgggacgt   1860
ggtcagaata ccggtattgc gttcgttttcc ttgaaggact gggccgatcg tccgggcgaa   1920
gaaaacaaag ttgaagcgat taccatgcgt gcaacgcgcg ctttctcgca aatcaaagat   1980
gcgatggttt tcgcctttaa cctgcccgca atcgtggaac tgggtactgc aaccggcttt   2040
gactttgagc tgattgacca ggctggcctt ggtcacgaaa aactgactca ggcgcgtaac   2100
cagttgcttg cagaagcagc gaagcaccct gatatgttga ccagcgtacg tccaaacggt   2160
ctggaagata ccccgcagtt taagattgat atcgaccagg aaaaagcgca ggcgctgggt   2220
gtttctatca acgacattaa caccactctg ggcgctgcat ggggcggcag ctatgtgaac   2280
gactttatcg accgcggtcg tgtgaagaaa gtttatgtca tgtcagaagc gaaataccgt   2340
atgctgccgg atgatatcgg cgactggtat gttcgtgctg ctgatggtca gatggtgcca   2400
ttctcggcgt tctcctcttc tcgttgggag tacggttcgc cgcgtctgga acgttacaac   2460
```

-continued

```
ggcctgccat ccatggaaat cttaggccag gcggcaccgg gtaaaagtac cggtgaagca    2520
atggagctga tggaacaact ggcgagcaaa ctgcctaccg tgttggctta tgactggacg    2580
gggatgtcct atcaggaacg tctctccggc aaccaggcac cttcactgta cgcgatttcg    2640
ttgattgtcg tgttcctgtg tctggcggcg ctgtacgaga gctggtcgat ccgttctcc     2700
gttatgctgg tcgttccgct gggggttatc ggtgcgttgc tggctgccac cttccgtggc    2760
ctgaccaatg acgtttactt ccaggtaggc ctgctcacaa ccattgggtt gtcggcgaag    2820
aacgcgatcc ttatcgtcga attcgccaaa gacttgatgg ataaagaagg taaaggtctg    2880
attgaagcga cgcttgatgc ggtgcggatg cgtttacgtc cgatcctgat gacctcgctg    2940
gcgtttatcc tcggcgttat gccgctggtt atcagtactg gtgctggttc cggcgcgcag    3000
aacgcagtag gtaccggtgt aatgggcggg atggtgaccg caacggtact ggcaatcttc    3060
ttcgttccgg tattctttgt ggtggttcgc cgccgcttta gccgcaagaa tgaagatatc    3120
gagcacagcc atactgtcga tcatcattga                                    3150
```

<210> SEQ ID NO 10
<211> LENGTH: 1049
<212> TYPE: PRT
<213> ORGANISM: Escherichia coli

<400> SEQUENCE: 10

```
Met Pro Asn Phe Phe Ile Asp Arg Pro Ile Phe Ala Trp Val Ile Ala
1               5                   10                  15

Ile Ile Ile Met Leu Ala Gly Gly Leu Ala Ile Leu Lys Leu Pro Val
            20                  25                  30

Ala Gln Tyr Pro Thr Ile Ala Pro Pro Ala Val Thr Ile Ser Ala Ser
        35                  40                  45

Tyr Pro Gly Ala Asp Ala Lys Thr Val Gln Asp Thr Val Thr Gln Val
    50                  55                  60

Ile Glu Gln Asn Met Asn Gly Ile Asp Asn Leu Met Tyr Met Ser Ser
65                  70                  75                  80

Asn Ser Asp Ser Thr Gly Thr Val Gln Ile Thr Leu Thr Phe Glu Ser
                85                  90                  95

Gly Thr Asp Ala Asp Ile Ala Gln Val Gln Val Gln Asn Lys Leu Gln
            100                 105                 110

Leu Ala Met Pro Leu Leu Pro Gln Glu Val Gln Gln Gln Gly Val Ser
        115                 120                 125

Val Glu Lys Ser Ser Ser Ser Phe Leu Met Val Gly Val Ile Asn
    130                 135                 140

Thr Asp Gly Thr Met Thr Gln Glu Asp Ile Ser Asp Tyr Val Ala Ala
145                 150                 155                 160

Asn Met Lys Asp Ala Ile Ser Arg Thr Ser Gly Val Gly Asp Val Gln
                165                 170                 175

Leu Phe Gly Ser Gln Tyr Ala Met Arg Ile Trp Met Asn Pro Asn Glu
            180                 185                 190

Leu Asn Lys Phe Gln Leu Thr Pro Val Asp Val Ile Thr Ala Ile Lys
        195                 200                 205

Ala Gln Asn Ala Gln Val Ala Ala Gly Gln Leu Gly Gly Thr Pro Pro
    210                 215                 220

Val Lys Gly Gln Gln Leu Asn Ala Ser Ile Ile Ala Gln Thr Arg Leu
225                 230                 235                 240

Thr Ser Thr Glu Glu Phe Gly Lys Ile Leu Leu Lys Val Asn Gln Asp
                245                 250                 255
```

```
Gly Ser Arg Val Leu Arg Asp Val Ala Lys Ile Glu Leu Gly Gly
            260                 265                 270

Glu Asn Tyr Asp Ile Ile Ala Glu Phe Asn Gly Gln Pro Ala Ser Gly
        275                 280                 285

Leu Gly Ile Lys Leu Ala Thr Gly Ala Asn Ala Leu Asp Thr Ala Ala
    290                 295                 300

Ala Ile Arg Ala Glu Leu Ala Lys Met Glu Pro Phe Phe Pro Ser Gly
305                 310                 315                 320

Leu Lys Ile Val Tyr Pro Tyr Asp Thr Thr Pro Phe Val Lys Ile Ser
                325                 330                 335

Ile His Glu Val Val Lys Thr Leu Val Glu Ala Ile Ile Leu Val Phe
            340                 345                 350

Leu Val Met Tyr Leu Phe Leu Gln Asn Phe Arg Ala Thr Leu Ile Pro
        355                 360                 365

Thr Ile Ala Val Pro Val Val Leu Leu Gly Thr Phe Ala Val Leu Ala
    370                 375                 380

Ala Phe Gly Phe Ser Ile Asn Thr Leu Thr Met Phe Gly Met Val Leu
385                 390                 395                 400

Ala Ile Gly Leu Leu Val Asp Asp Ala Ile Val Val Val Glu Asn Val
                405                 410                 415

Glu Arg Val Met Ala Glu Glu Gly Leu Pro Pro Lys Glu Ala Thr Arg
            420                 425                 430

Lys Ser Met Gly Gln Ile Gln Gly Ala Leu Val Gly Ile Ala Met Val
        435                 440                 445

Leu Ser Ala Val Phe Val Pro Met Ala Phe Phe Gly Gly Ser Thr Gly
    450                 455                 460

Ala Ile Tyr Arg Gln Phe Ser Ile Thr Ile Val Ser Ala Met Ala Leu
465                 470                 475                 480

Ser Val Leu Val Ala Leu Ile Leu Thr Pro Ala Leu Cys Ala Thr Met
                485                 490                 495

Leu Lys Pro Ile Ala Lys Gly Asp His Gly Glu Gly Lys Lys Gly Phe
            500                 505                 510

Phe Gly Trp Phe Asn Arg Met Phe Glu Lys Ser Thr His His Tyr Thr
        515                 520                 525

Asp Ser Val Gly Gly Ile Leu Arg Ser Thr Gly Arg Tyr Leu Val Leu
    530                 535                 540

Tyr Leu Ile Ile Val Val Gly Met Ala Tyr Leu Phe Val Arg Leu Pro
545                 550                 555                 560

Ser Ser Phe Leu Pro Asp Glu Asp Gln Gly Val Phe Met Thr Met Val
                565                 570                 575

Gln Leu Pro Ala Gly Ala Thr Gln Glu Arg Thr Gln Lys Val Leu Asn
            580                 585                 590

Glu Val Thr His Tyr Tyr Leu Thr Lys Glu Lys Asn Asn Val Glu Ser
        595                 600                 605

Val Phe Ala Val Asn Gly Phe Gly Phe Ala Gly Arg Gly Gln Asn Thr
    610                 615                 620

Gly Ile Ala Phe Val Ser Leu Lys Asp Trp Ala Asp Arg Pro Gly Glu
625                 630                 635                 640

Glu Asn Lys Val Glu Ala Ile Thr Met Arg Ala Thr Arg Ala Phe Ser
                645                 650                 655

Gln Ile Lys Asp Ala Met Val Phe Ala Phe Asn Leu Pro Ala Ile Val
            660                 665                 670
```

```
Glu Leu Gly Thr Ala Thr Gly Phe Asp Phe Glu Leu Ile Asp Gln Ala
            675                 680                 685

Gly Leu Gly His Glu Lys Leu Thr Gln Ala Arg Asn Gln Leu Leu Ala
        690                 695                 700

Glu Ala Ala Lys His Pro Asp Met Leu Thr Ser Val Arg Pro Asn Gly
705                 710                 715                 720

Leu Glu Asp Thr Pro Gln Phe Lys Ile Asp Ile Asp Gln Glu Lys Ala
                725                 730                 735

Gln Ala Leu Gly Val Ser Ile Asn Asp Ile Asn Thr Thr Leu Gly Ala
            740                 745                 750

Ala Trp Gly Gly Ser Tyr Val Asn Asp Phe Ile Asp Arg Gly Arg Val
        755                 760                 765

Lys Lys Val Tyr Val Met Ser Glu Ala Lys Tyr Arg Met Leu Pro Asp
770                 775                 780

Asp Ile Gly Asp Trp Tyr Val Arg Ala Ala Asp Gly Gln Met Val Pro
785                 790                 795                 800

Phe Ser Ala Phe Ser Ser Arg Trp Glu Tyr Gly Ser Pro Arg Leu
                805                 810                 815

Glu Arg Tyr Asn Gly Leu Pro Ser Met Glu Ile Leu Gly Gln Ala Ala
            820                 825                 830

Pro Gly Lys Ser Thr Gly Glu Ala Met Glu Leu Met Glu Gln Leu Ala
        835                 840                 845

Ser Lys Leu Pro Thr Gly Val Gly Tyr Asp Trp Thr Gly Met Ser Tyr
850                 855                 860

Gln Glu Arg Leu Ser Gly Asn Gln Ala Pro Ser Leu Tyr Ala Ile Ser
865                 870                 875                 880

Leu Ile Val Val Phe Leu Cys Leu Ala Ala Leu Tyr Glu Ser Trp Ser
                885                 890                 895

Ile Pro Phe Ser Val Met Leu Val Val Pro Leu Gly Val Ile Gly Ala
            900                 905                 910

Leu Leu Ala Ala Thr Phe Arg Gly Leu Thr Asn Asp Val Tyr Phe Gln
        915                 920                 925

Val Gly Leu Leu Thr Thr Ile Gly Leu Ser Ala Lys Asn Ala Ile Leu
930                 935                 940

Ile Val Glu Phe Ala Lys Asp Leu Met Asp Lys Glu Gly Lys Gly Leu
945                 950                 955                 960

Ile Glu Ala Thr Leu Asp Ala Val Arg Met Arg Leu Arg Pro Ile Leu
                965                 970                 975

Met Thr Ser Leu Ala Phe Ile Leu Gly Val Met Pro Leu Val Ile Ser
            980                 985                 990

Thr Gly Ala Gly Ser Gly Ala Gln Asn Ala Val Gly Thr Gly Val Met
        995                 1000                1005

Gly Gly Met Val Thr Ala Thr Val Leu Ala Ile Phe Phe Val Pro
1010                1015                1020

Val Phe Phe Val Val Val Arg Arg Arg Phe Ser Arg Lys Asn Glu
    1025                1030                1035

Asp Ile Glu His Ser His Thr Val Asp His His
    1040                1045

<210> SEQ ID NO 11
<211> LENGTH: 399
<212> TYPE: DNA
<213> ORGANISM: Escherichia coli

<400> SEQUENCE: 11
```

```
atgagtaaga cactgaacat tatctggcaa tatttacgcg ctttcgtcct gatttatgcc    60
tgcctgtatg caggcatttt cattgcttcc ctgctaccgg taaccattcc gggcagcatc   120
atcgggatgc tgatcctgtt tgtcctgctg gccttgcaaa ttcttccggc aaaatgggtc   180
aatccggggt gctacgtact gattcgctat atggcgctat tgtttgtgcc gattggcgta   240
ggcgtcatgc aatattttga tttgctccgc gcacagtttg gcccggtagt ggtttcctgt   300
gcagtcagta cgctggtggt tttctggtg gtgagctgga gttcgcaact ggtacacggt   360
gaacgtaaag tcgtaggtca gaaaggatca gaagaatga                          399
```

```
<210> SEQ ID NO 12
<211> LENGTH: 132
<212> TYPE: PRT
<213> ORGANISM: Escherichia coli

<400> SEQUENCE: 12
```

```
Met Ser Lys Thr Leu Asn Ile Ile Trp Gln Tyr Leu Arg Ala Phe Val
1               5                   10                  15

Leu Ile Tyr Ala Cys Leu Tyr Ala Gly Ile Phe Ile Ala Ser Leu Leu
            20                  25                  30

Pro Val Thr Ile Pro Gly Ser Ile Ile Gly Met Leu Ile Leu Phe Val
        35                  40                  45

Leu Leu Ala Leu Gln Ile Leu Pro Ala Lys Trp Val Asn Pro Gly Cys
    50                  55                  60

Tyr Val Leu Ile Arg Tyr Met Ala Leu Leu Phe Val Pro Ile Gly Val
65                  70                  75                  80

Gly Val Met Gln Tyr Phe Asp Leu Leu Arg Ala Gln Phe Gly Pro Val
                85                  90                  95

Val Val Ser Cys Ala Val Ser Thr Leu Val Val Phe Leu Val Val Ser
            100                 105                 110

Trp Ser Ser Gln Leu Val His Gly Glu Arg Lys Val Val Gly Gln Lys
        115                 120                 125

Gly Ser Glu Glu
    130
```

```
<210> SEQ ID NO 13
<211> LENGTH: 1101
<212> TYPE: DNA
<213> ORGANISM: Escherichia coli

<400> SEQUENCE: 13
```

```
atgcgaggga aaaacgcat tgggttattg tttttgctga tagcggttgt ggttggtggc    60
ggcgggttat tgctggcgca aaaagtctta cataaaacgt cggatacagc attttgcctt   120
tcctgccact cgatgagtaa accttttgag gaatatcagg gaactgtcca cttttcgaac   180
cagaaaggga tacgtgcgga atgtgccgat tgccatattc aaagtcagg gatggattat   240 ttatttgcta aattaaaggc atctaaagat atttatcatg aatttgttag cggcaaaata   300
gacagtgacg ataagttcga agctcatcgc caggaaatgg ccgaaacagt atggaaagaa   360
ttaaaagcca ctgactctgc aacgtgccgt agttgccatt cttttgatgc catggatatt   420
gcctcgcaaa gtgaatctgc gcagaaaatg cataacaaag cacaaaagga cagcgaaacc   480
tgtatcgatt gtcataaagg cattgcccat tttccgccag aaataaaaat ggatgacaac   540
gcggcgcatg agctgaaaag tcaggccgct acttcagtta ctaatggcgc acatatttat   600
cctttcaaaa cttctcacat aggcgagctg gctaccgtga atcctggaac cgatctcacc   660
```

```
gtcgttgatg ccagtggcaa acagccgatc gttctgttgc agggttatca aatgcagggc      720
agtgaaaaca cgctctacct ggcggcaggt caacggctgg cgctagccac attaagtgaa      780
gaaggtatca aggcgctcac tgtaaacggg gaatggcagg ctgacgaata cggcaatcaa      840
tggcgtcagg cgtctttaca gggtgcgctt accgatcccg cattagcgga ccgtaaaccg      900
ctatggcaat acgctgaaaa acttgacgat acctattgcg ctggttgtca tgccccctatt      960 gccgccgacc attacaccgt caatgcgtgg ccgtccattg ccaaaggaat ggggggcacga     1020 accagcatga gcgaaaacga actggacatt ttaacgcggt atttccagta caacgccaaa     1080
gatattaccg agaaacagtg a                                                1101

<210> SEQ ID NO 14
<211> LENGTH: 366
<212> TYPE: PRT
<213> ORGANISM: Escherichia coli

<400> SEQUENCE: 14

Met Arg Gly Lys Lys Arg Ile Gly Leu Leu Phe Leu Leu Ile Ala Val
1               5                   10                  15

Val Val Gly Gly Gly Leu Leu Ala Gln Lys Val Leu His Lys
            20                  25                  30

Thr Ser Asp Thr Ala Phe Cys Leu Ser Cys His Ser Met Ser Lys Pro
        35                  40                  45

Phe Glu Glu Tyr Gln Gly Thr Val His Phe Ser Asn Gln Lys Gly Ile
    50                  55                  60

Arg Ala Glu Cys Ala Asp Cys His Ile Pro Lys Ser Gly Met Asp Tyr
65                  70                  75                  80

Leu Phe Ala Lys Leu Lys Ala Ser Lys Asp Ile Tyr His Glu Phe Val
                85                  90                  95

Ser Gly Lys Ile Asp Ser Asp Lys Phe Glu Ala His Arg Gln Glu
            100                 105                 110

Met Ala Glu Thr Val Trp Lys Glu Leu Lys Ala Thr Asp Ser Ala Thr
        115                 120                 125

Cys Arg Ser Cys His Ser Phe Asp Ala Met Asp Ile Ala Ser Gln Ser
    130                 135                 140

Glu Ser Ala Gln Lys Met His Asn Lys Ala Gln Lys Asp Ser Glu Thr
145                 150                 155                 160

Cys Ile Asp Cys His Lys Gly Ile Ala His Phe Pro Pro Glu Ile Lys
                165                 170                 175

Met Asp Asp Asn Ala Ala His Glu Leu Glu Ser Gln Ala Ala Thr Ser
            180                 185                 190

Val Thr Asn Gly Ala His Ile Tyr Pro Phe Lys Thr Ser His Ile Gly
        195                 200                 205

Glu Leu Ala Thr Val Asn Pro Gly Thr Asp Leu Thr Val Val Asp Ala
    210                 215                 220

Ser Gly Lys Gln Pro Ile Val Leu Leu Gln Gly Tyr Gln Met Gln Gly
225                 230                 235                 240

Ser Glu Asn Thr Leu Tyr Leu Ala Ala Gly Gln Arg Leu Ala Leu Ala
                245                 250                 255

Thr Leu Ser Glu Glu Gly Ile Lys Ala Leu Thr Val Asn Gly Glu Trp
            260                 265                 270

Gln Ala Asp Glu Tyr Gly Asn Gln Trp Arg Gln Ala Ser Leu Gln Gly
        275                 280                 285
```

```
Ala Leu Thr Asp Pro Ala Leu Ala Asp Arg Lys Pro Leu Trp Gln Tyr
    290                 295                 300

Ala Glu Lys Leu Asp Asp Thr Tyr Cys Ala Gly Cys His Ala Pro Ile
305                 310                 315                 320

Ala Ala Asp His Tyr Thr Val Asn Ala Trp Pro Ser Ile Ala Lys Gly
                325                 330                 335

Met Gly Ala Arg Thr Ser Met Ser Glu Asn Glu Leu Asp Ile Leu Thr
            340                 345                 350

Arg Tyr Phe Gln Tyr Asn Ala Lys Asp Ile Thr Glu Lys Gln
        355                 360                 365

<210> SEQ ID NO 15
<211> LENGTH: 972
<212> TYPE: DNA
<213> ORGANISM: Escherichia coli

<400> SEQUENCE: 15
atggaaacga aaaaaataa tagcgaatac attcctgagt ttgataaatc ctttcgccac      60
ccgcgctact ggggagcatg gctgggcgta gcagcgatgg cgggtatcgc tttaacgccg     120
ccaaagttcc gtgatcccat tctggcacgg ctgggacgtt ttgccggacg actgggaaaa     180
agctcacgcc gtcgtgcgtt aatcaatctg tcgctctgct tccagaacg tagtgaagct     240
gaacgcgaag cgattgttga tgagatgttt gccaccgcgc cgcaagcgat ggcaatgatg     300
gctgagttgg caatacgcgg gccggagaaa attcagccgc gcgttgactg caagggctg      360
gagatcatcg aagagatgcg gcgtaataac gagaaagtta tctttctggt gccgcacggt     420
tgggccgtcg atattcctgc catgctgatg gcctcgcaag gcagaaaat ggcagcgatg      480
ttccataatc agggcaaccc ggttttttgat tatgtctgga cacggtgcg tcgtcgcttt    540
ggcggtcgtc tgcatgcgag aaatgacggt attaaaccat tcatccagtc ggtacgtcag     600
gggtactggg atattatttt acccgatcag gatcatggcc cagagcacag cgaatttgtg    660
gatttctttg ccacctataa agcgacgttg cccgcgattg gtcgtttgat gaaagtgtgc    720
cgtgcgcgcg ttgtaccgct gtttccgatt tatgatggca agacgcatcg tctgacgatt    780
caggtgcgcc caccgatgga tgatctgtta gaggcggatg atcatacgat gcgcggcgg      840
atgaatgaag aagtcgagat ttttgttggt ccgcgaccag aacaatacac ctggatacta    900
aaattgctga aactcgcaa accgggcgaa atccagccgt ataagcgcaa agatctttat     960
cccatcaaat aa                                                         972

<210> SEQ ID NO 16
<211> LENGTH: 323
<212> TYPE: PRT
<213> ORGANISM: Escherichia coli

<400> SEQUENCE: 16

Met Glu Thr Lys Lys Asn Asn Ser Glu Tyr Ile Pro Glu Phe Asp Lys
1               5                   10                  15

Ser Phe Arg His Pro Arg Tyr Trp Gly Ala Trp Leu Gly Val Ala Ala
            20                  25                  30

Met Ala Gly Ile Ala Leu Thr Pro Pro Lys Phe Arg Asp Pro Ile Leu
        35                  40                  45

Ala Arg Leu Gly Arg Phe Ala Gly Arg Leu Gly Lys Ser Ser Arg Arg
    50                  55                  60

Arg Ala Leu Ile Asn Leu Ser Leu Cys Phe Pro Glu Arg Ser Glu Ala
65                  70                  75                  80
```

Glu Arg Glu Ala Ile Val Asp Glu Met Phe Ala Thr Ala Pro Gln Ala
                85                  90                  95

Met Ala Met Met Ala Glu Leu Ala Ile Arg Gly Pro Glu Lys Ile Gln
            100                 105                 110

Pro Arg Val Asp Trp Gln Gly Leu Glu Ile Ile Glu Glu Met Arg Arg
        115                 120                 125

Asn Asn Glu Lys Val Ile Phe Leu Val Pro His Gly Trp Ala Val Asp
130                 135                 140

Ile Pro Ala Met Leu Met Ala Ser Gln Gly Gln Lys Met Ala Ala Met
145                 150                 155                 160

Phe His Asn Gln Gly Asn Pro Val Phe Asp Tyr Val Trp Asn Thr Val
                165                 170                 175

Arg Arg Arg Phe Gly Gly Arg Leu His Ala Arg Asn Asp Gly Ile Lys
            180                 185                 190

Pro Phe Ile Gln Ser Val Arg Gln Gly Tyr Trp Gly Tyr Tyr Leu Pro
        195                 200                 205

Asp Gln Asp His Gly Pro Glu His Ser Glu Phe Val Asp Phe Phe Ala
210                 215                 220

Thr Tyr Lys Ala Thr Leu Pro Ala Ile Gly Arg Leu Met Lys Val Cys
225                 230                 235                 240

Arg Ala Arg Val Val Pro Leu Phe Pro Ile Tyr Asp Gly Lys Thr His
                245                 250                 255

Arg Leu Thr Ile Gln Val Arg Pro Pro Met Asp Asp Leu Leu Glu Ala
            260                 265                 270

Asp Asp His Thr Ile Ala Arg Arg Met Asn Glu Glu Val Glu Ile Phe
        275                 280                 285

Val Gly Pro Arg Pro Glu Gln Tyr Thr Trp Ile Leu Lys Leu Leu Lys
290                 295                 300

Thr Arg Lys Pro Gly Glu Ile Gln Pro Tyr Lys Arg Lys Asp Leu Tyr
305                 310                 315                 320

Pro Ile Lys

<210> SEQ ID NO 17
<211> LENGTH: 1917
<212> TYPE: DNA
<213> ORGANISM: Escherichia coli

<400> SEQUENCE: 17
atgggtaaaa taattggtat cgacctgggt actaccaact cttgtgtagc gattatggat    60
ggcaccactc ctcgcgtgct ggagaacgcc gaaggcgatc gcaccacgcc ttctatcatt   120
gcctataccc aggatggtga aactctagtt ggtcagccgg ctaaacgtca ggcagtgacg   180
aacccgcaaa acactctgtt tgcgattaaa cgcctgattg gtcgccgctt ccaggacgaa   240
gaagtacagc gtgatgtttc catcatgccg ttcaaaatta ttgctgctga taacggcgac   300
gcatgggtcg aagttaaagg ccagaaaatg gcaccgccgc agatttctgc tgaagtgctg   360
aaaaaaatga agaaaaccgc tgaagattac ctgggtgaac ggtaactga agctgttatc   420 accgtaccgg catactttaa cgatgctcag cgtcaggcaa ccaaagacgc aggccgtatc   480
gctggtctgg aagtaaaacg tatcatcaac gaaccgaccg cagctgcgct ggcttacggt   540
ctggacaaag gcactggcaa ccgtactatc gcggtttatg acctgggtgg tggtactttc   600
gatatttcta ttatcgaaat cgacgaagtt gacggcgaaa aaaccttcga agttctggca   660
accaacggtg ataccccacct gggggggtgaa gacttcgaca gccgtctgat caactatctg   720

```
gttgaagaat tcaagaaaga tcagggcatt gacctgcgca acgatccgct ggcaatgcag      780
cgcctgaaag aagcggcaga aaaagcgaaa atcgaactgt cttccgctca gcagaccgac      840
gttaacctgc catacatcac tgcagacgcg accggtccga acacatgaa catcaaagtg      900 actcgtgcga aactggaaag cctggttgaa gatctggtaa accgttccat tgagccgctg      960
aaagttgcac tgcaggacgc tggcctgtcc gtatctgata tcgacgacgt tatcctcgtt     1020
ggtggtcaga ctcgtatgcc aatggttcag aagaaagttg ctgagttctt tggtaaagag     1080
ccgcgtaaag acgttaaccc ggacgaagct gtagcaatcg gtgctgctgt tcagggtggt     1140
gttctgactg gtgacgtaaa agactactg ctgctggacg ttaccccgct gtctctgggt      1200
atcgaaacca tgggcggtgt gatgacgacg ctgatcgcga aaacaccac tatcccgacc      1260 aagcacagcc aggtgttctc taccgctgaa gacaaccagt ctgcggtaac catccatgtg     1320
ctgcagggtg aacgtaaacg tgcggctgat aacaaatctc tgggtcagtt caacctagat     1380
ggtatcaacc cggcaccgcg cggcatgccg cagatcgaag ttaccttcga tatcgatgct     1440
gacggtatcc tgcacgtttc cgcgaaagat aaaaacagcg gtaaagagca agatcacc     1500 atcaaggctt cttctggtct gaacgaagat gaaatccaga aaatggtacg cgacgcagaa     1560
gctaacgccg aagctgaccg taagtttgaa gagctggtac agactcgcaa ccagggcgac     1620
catctgctgc acagcacccg taagcaggtt gaagaagcag cgacaaaact gccggctgac     1680
gacaaaactg ctatcgagtc tgcgctgact gcactggaaa ctgctctgaa aggtgaagac     1740
aaagccgcta tcgaagcgaa aatgcaggaa ctggcacagg tttcccagaa actgatggaa     1800
atcgcccagc agcaacatgc ccagcagcag actgccggtg ctgatgcttc tgcaaacaac     1860
gcgaaagatg acgatgttgt cgacgctgaa tttgaagaag tcaaagacaa aaaataa       1917

<210> SEQ ID NO 18
<211> LENGTH: 638
<212> TYPE: PRT
<213> ORGANISM: Escherichia coli

<400> SEQUENCE: 18

Met Gly Lys Ile Ile Gly Ile Asp Leu Gly Thr Thr Asn Ser Cys Val
1               5                   10                  15

Ala Ile Met Asp Gly Thr Thr Pro Arg Val Leu Glu Asn Ala Glu Gly
            20                  25                  30

Asp Arg Thr Thr Pro Ser Ile Ile Ala Tyr Thr Gln Asp Gly Glu Thr
        35                  40                  45

Leu Val Gly Gln Pro Ala Lys Arg Gln Ala Val Thr Asn Pro Gln Asn
    50                  55                  60

Thr Leu Phe Ala Ile Lys Arg Leu Ile Gly Arg Arg Phe Gln Asp Glu
65                  70                  75                  80

Glu Val Gln Arg Asp Val Ser Ile Met Pro Phe Lys Ile Ile Ala Ala
                85                  90                  95

Asp Asn Gly Asp Ala Trp Val Glu Val Lys Gly Gln Lys Met Ala Pro
            100                 105                 110

Pro Gln Ile Ser Ala Glu Val Leu Lys Lys Met Lys Lys Thr Ala Glu
        115                 120                 125

Asp Tyr Leu Gly Glu Pro Val Thr Glu Ala Val Ile Thr Val Pro Ala
    130                 135                 140

Tyr Phe Asn Asp Ala Gln Arg Gln Ala Thr Lys Asp Ala Gly Arg Ile
145                 150                 155                 160
```

Ala Gly Leu Glu Val Lys Arg Ile Ile Asn Glu Pro Thr Ala Ala Ala
            165                 170                 175

Leu Ala Tyr Gly Leu Asp Lys Gly Thr Gly Asn Arg Thr Ile Ala Val
        180                 185                 190

Tyr Asp Leu Gly Gly Gly Thr Phe Asp Ile Ser Ile Ile Glu Ile Asp
        195                 200                 205

Glu Val Asp Gly Glu Lys Thr Phe Glu Val Leu Ala Thr Asn Gly Asp
        210                 215                 220

Thr His Leu Gly Gly Glu Asp Phe Asp Ser Arg Leu Ile Asn Tyr Leu
225                 230                 235                 240

Val Glu Glu Phe Lys Lys Asp Gln Gly Ile Asp Leu Arg Asn Asp Pro
            245                 250                 255

Leu Ala Met Gln Arg Leu Lys Glu Ala Ala Glu Lys Ala Lys Ile Glu
        260                 265                 270

Leu Ser Ser Ala Gln Gln Thr Asp Val Asn Leu Pro Tyr Ile Thr Ala
        275                 280                 285

Asp Ala Thr Gly Pro Lys His Met Asn Ile Lys Val Thr Arg Ala Lys
        290                 295                 300

Leu Glu Ser Leu Val Glu Asp Leu Val Asn Arg Ser Ile Glu Pro Leu
305                 310                 315                 320

Lys Val Ala Leu Gln Asp Ala Gly Leu Ser Val Ser Asp Ile Asp Asp
            325                 330                 335

Val Ile Leu Val Gly Gly Gln Thr Arg Met Pro Met Val Gln Lys Lys
        340                 345                 350

Val Ala Glu Phe Phe Gly Lys Glu Pro Arg Lys Asp Val Asn Pro Asp
        355                 360                 365

Glu Ala Val Ala Ile Gly Ala Ala Val Gln Gly Gly Val Leu Thr Gly
        370                 375                 380

Asp Val Lys Asp Val Leu Leu Leu Asp Val Thr Pro Leu Ser Leu Gly
385                 390                 395                 400

Ile Glu Thr Met Gly Gly Val Met Thr Thr Leu Ile Ala Lys Asn Thr
            405                 410                 415

Thr Ile Pro Thr Lys His Ser Gln Val Phe Ser Thr Ala Glu Asp Asn
        420                 425                 430

Gln Ser Ala Val Thr Ile His Val Leu Gln Gly Glu Arg Lys Arg Ala
        435                 440                 445

Ala Asp Asn Lys Ser Leu Gly Gln Phe Asn Leu Asp Gly Ile Asn Pro
450                 455                 460

Ala Pro Arg Gly Met Pro Gln Ile Glu Val Thr Phe Asp Ile Asp Ala
465                 470                 475                 480

Asp Gly Ile Leu His Val Ser Ala Lys Asp Lys Asn Ser Gly Lys Glu
            485                 490                 495

Gln Lys Ile Thr Ile Lys Ala Ser Ser Gly Leu Asn Glu Asp Glu Ile
        500                 505                 510

Gln Lys Met Val Arg Asp Ala Glu Ala Asn Ala Glu Ala Asp Arg Lys
        515                 520                 525

Phe Glu Glu Leu Val Gln Thr Arg Asn Gln Gly Asp His Leu Leu His
        530                 535                 540

Ser Thr Arg Lys Gln Val Glu Glu Ala Gly Asp Lys Leu Pro Ala Asp
545                 550                 555                 560

Asp Lys Thr Ala Ile Glu Ser Ala Leu Thr Ala Leu Glu Thr Ala Leu
            565                 570                 575

Lys Gly Glu Asp Lys Ala Ala Ile Glu Ala Lys Met Gln Glu Leu Ala

```
            580                 585                 590
Gln Val Ser Gln Lys Leu Met Glu Ile Ala Gln Gln His Ala Gln
        595                 600                 605

Gln Gln Thr Ala Gly Ala Asp Ala Ser Ala Asn Asn Ala Lys Asp Asp
    610                 615                 620

Asp Val Val Asp Ala Glu Phe Glu Glu Val Lys Asp Lys Lys
625                 630                 635
```

<210> SEQ ID NO 19
<211> LENGTH: 1647
<212> TYPE: DNA
<213> ORGANISM: Escherichia coli

<400> SEQUENCE: 19

| | | | | | |
|---|---|---|---|---|---|
| atggcagcta | aagacgtaaa | attcggtaac | gacgctcgtg | tgaaaatgct | gcgcggcgta | 60 |
| aacgtactgg | cagatgcagt | gaaagttacc | ctcggtccaa | aaggccgtaa | cgtagttctg | 120 |
| gataaatctt | tcggtgcacc | gaccatcacc | aaagatggtt | tttccgttgc | tcgtgaaatc | 180 |
| gaactggaag | acaagttcga | aaatatgggt | gcgcagatgg | tgaaagaagt | tgcctctaaa | 240 |
| gcaaacgacg | ctgcaggcga | cggtaccacc | actgcaaccg | tactggctca | ggctatcatc | 300 |
| actgaaggtc | tgaaagctgt | tgctgcgggc | atgaacccga | tggacctgaa | acgtggtatc | 360 |
| gacaaagcgg | ttaccgctgc | agttgaagaa | ctgaaagcgc | tgtccgtacc | atgctctgac | 420 |
| tctaaagcga | ttgctcaggt | tggtaccatc | tccgctaact | ccgacgaaac | cgtaggtaaa | 480 |
| ctgatcgctg | aagcgatgga | caaagtcggt | aaagaaggcg | ttatcaccgt | tgaagacggt | 540 |
| accggtctgc | aggacgaact | ggacgtggtt | gaaggtatgc | agttcgaccg | tggctacctg | 600 |
| tctccttact | tcatcaacaa | gccggaaact | ggcgcagtag | aactgaaaag | cccgttcatc | 660 |
| ctgctggctg | acaagaaaat | ctccaacatc | cgcgaaatgc | tgccggttct | ggaagctgtt | 720 |
| gccaaagcag | gcaaaccgct | gctgatcatc | gctgaagatg | tagaaggcga | agcgctggca | 780 |
| actctggttg | ttaacaccat | gcgtggcatc | gtgaaagtcg | ctgcggttaa | agcaccgggc | 840 |
| ttcggcgatc | gtcgtaaagc | tatgctgcag | gatatcgcaa | ccctgactgg | cggtaccgtg | 900 |
| atctctgaag | agatcggtat | ggagctggaa | aaagcaaccc | tggaagacct | gggtcaggct | 960 |
| aaacgtgttg | tgatcaacaa | agacaccacc | actatcatcg | atggcgtggg | tgaagaagct | 1020 |
| gcaatccagg | gccgtgttgc | tcagatccgt | cagcagattg | aagaagcaac | ttctgactac | 1080 |
| gaccgtgaaa | aactgcagga | acgcgtagcg | aaactggcag | gcggcgttgc | agttatcaaa | 1140 |
| gtgggtgctg | ctaccgaagt | tgaaatgaaa | gagaaaaaag | cacgcgttga | agatgccctg | 1200 |
| cacgcgaccc | gtgctgcggt | agaagaaggc | gtggttgctg | gtggtggtgt | tgcgctgatc | 1260 |
| cgcgtagcgt | ctaaactggc | tgacctgcgt | ggtcagaacg | aagaccagaa | cgtgggtatc | 1320 |
| aaagttgcac | tgcgtgcaat | ggaagctccg | ctgcgtcaga | tcgtattgaa | ctgcggcgaa | 1380 |
| gaaccgtctg | ttgttgctaa | caccgttaaa | ggcggcgacg | gcaactacgg | ttacaacgca | 1440 |
| gcaaccgaag | aatacggcaa | catgatcgac | atgggtatcc | tggatccaac | caaagtaact | 1500 |
| cgttctgctc | tgcagtacgc | agcttctgtg | gctggcctga | tgatcaccac | cgaatgcatg | 1560 |
| gttaccgacc | tgccgaaaaa | cgatgcagct | gacttaggcg | ctgctggcgg | tatgggcggc | 1620 |
| atgggtggca | tgggcggcat | gatgtaa | | | | 1647 |

<210> SEQ ID NO 20
<211> LENGTH: 548
<212> TYPE: PRT

<213> ORGANISM: Escherichia coli

<400> SEQUENCE: 20

```
Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
            20                  25                  30

Pro Lys Gly Arg Asn Val Val Leu Asp Lys Ser Phe Gly Ala Pro Thr
        35                  40                  45

Ile Thr Lys Asp Gly Val Ser Val Ala Arg Glu Ile Glu Leu Glu Asp
    50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
        115                 120                 125

Glu Glu Leu Lys Ala Leu Ser Val Pro Cys Ser Asp Ser Lys Ala Ile
130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205

Glu Thr Gly Ala Val Glu Leu Glu Ser Pro Phe Ile Leu Leu Ala Asp
    210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Leu Val Val Asn Thr Met Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Gly Gly Thr Val Ile Ser Glu Glu
    290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
            340                 345                 350

Ile Glu Glu Ala Thr Ser Asp Tyr Asp Arg Glu Lys Leu Gln Glu Arg
        355                 360                 365

Val Ala Lys Leu Ala Gly Gly Val Ala Val Ile Lys Val Gly Ala Ala
    370                 375                 380

Thr Glu Val Glu Met Lys Glu Lys Lys Ala Arg Val Glu Asp Ala Leu
385                 390                 395                 400
```

His Ala Thr Arg Ala Ala Val Glu Glu Gly Val Ala Gly Gly Gly
                405                 410                 415

Val Ala Leu Ile Arg Val Ala Ser Lys Leu Ala Asp Leu Arg Gly Gln
            420                 425                 430

Asn Glu Asp Gln Asn Val Gly Ile Lys Val Ala Leu Arg Ala Met Glu
        435                 440                 445

Ala Pro Leu Arg Gln Ile Val Leu Asn Cys Gly Glu Pro Ser Val
    450                 455                 460

Val Ala Asn Thr Val Lys Gly Gly Asp Gly Asn Tyr Gly Tyr Asn Ala
465                 470                 475                 480

Ala Thr Glu Glu Tyr Gly Asn Met Ile Asp Met Gly Ile Leu Asp Pro
                485                 490                 495

Thr Lys Val Thr Arg Ser Ala Leu Gln Tyr Ala Ala Ser Val Ala Gly
            500                 505                 510

Leu Met Ile Thr Thr Glu Cys Met Val Thr Asp Leu Pro Lys Asn Asp
        515                 520                 525

Ala Ala Asp Leu Gly Ala Ala Gly Gly Met Gly Gly Met Gly Gly Met
    530                 535                 540

Gly Gly Met Met
545

<210> SEQ ID NO 21
<211> LENGTH: 291
<212> TYPE: DNA
<213> ORGANISM: Escherichia coli

<400> SEQUENCE: 21
atgcaaaaca caactcatga caacgtaatt ctggagctca ccgttcgcaa ccatccgggc      60
gtaatgaccc acgtttgtgg cctttttgcc cgccgcgctt ttaacgttga aggcattctt     120
tgtctgccga ttcaggacag cgacaaaagc catatctggc tactggtcaa tgacgaccag     180
cgtctggagc agatgataag ccaaatcgat aagctggaag atgtcgtgaa agtgcagcgt     240
aatcagtccg atccgacgat gtttaacaag atcgcggtgt tttttcagta a              291

<210> SEQ ID NO 22
<211> LENGTH: 96
<212> TYPE: PRT
<213> ORGANISM: Escherichia coli

<400> SEQUENCE: 22

Met Gln Asn Thr Thr His Asp Asn Val Ile Leu Glu Leu Thr Val Arg
1               5                   10                  15

Asn His Pro Gly Val Met Thr His Val Cys Gly Leu Phe Ala Arg Arg
            20                  25                  30

Ala Phe Asn Val Glu Gly Ile Leu Cys Leu Pro Ile Gln Asp Ser Asp
        35                  40                  45

Lys Ser His Ile Trp Leu Leu Val Asn Asp Asp Gln Arg Leu Glu Gln
    50                  55                  60

Met Ile Ser Gln Ile Asp Lys Leu Glu Asp Val Val Lys Val Gln Arg
65                  70                  75                  80

Asn Gln Ser Asp Pro Thr Met Phe Asn Lys Ile Ala Val Phe Phe Gln
                85                  90                  95

<210> SEQ ID NO 23
<211> LENGTH: 1167
<212> TYPE: DNA
<213> ORGANISM: Escherichia coli

<400> SEQUENCE: 23

```
atgatcaaga ttggcgttat cgccgatgat tttaccggcg cgacggatat cgccagtttt    60
ctggtggaaa acggtctacc aacggtacaa attaacggtg ttccaacagg taaaatgccg   120
gaagcaatcg acgcactggt gatcagcctg aaaacgcgct cctgtccagt ggttgaagcc   180
acacagcaat cgctggcggc tctgagctgg ttgcaacagc aaggttgcaa acagatctat   240
ttcaaatact gctctacttt cgacagtacg gcgaaaggta atattggccc ggttaccgat   300
gccttaatgg atgctctcga cacgccgttt acggtcttct ctccggccct gccggtcaac   360
ggacgtacgg tttatcaggg gtatttgttc gtaatgaatc aactgctggc cgaatccggg   420
atgcgccatc acccggtaaa tcccatgacc gacagctatc ttccccgtct ggttgaagcg   480
caatccacag ggcgctgcgg cgtcgtttcg gcacatgttt tcgaacaagg tgtggatgcc   540
gttcgtcaag agctggctcg cttacagcaa gagggctacc gctacgcggt gcttgatgcg   600
ctgaccgaac accatctgga aattcaggga gaagccttgc gcgatgcccc actggtaacg   660
ggcggttctg gtctggcgat tggcctggcc cggcagtggg cgcaagaaaa cggtaaccag   720
gctcgcaaag cagggcgtcc gctcgctggg cgcggcgtag tgctctccgg ttcatgctct   780
caaatgacca accgccaggt agcacattac cgtcaaattg caccagcccg tgaagttgat   840
gtggcacgct gcctctcaat tgaaactctg gccgcttatg cacacgaact ggcagagtgg   900
gttctgggcc aggaaagtgt acttgctcca ctggttttg  ccaccgccag cactgacgca   960
ttggcagcaa ttcaacagca atacggtgca caaaaagcca gtcaggcagt agaaacactg  1020
ttttctcaac tagcggcgcg gttagcagcg gaaggcgtga cacgctttat tgtcgcaggc  1080
ggtgagacct ccggcgtagt cacacagagc ctgggaataa aagggtttca tattggccca  1140
accatttccc cggcgtgccg tgggtaa                                       1167
```

<210> SEQ ID NO 24
<211> LENGTH: 420
<212> TYPE: PRT
<213> ORGANISM: Escherichia coli

<400> SEQUENCE: 24

```
Met Ile Lys Ile Gly Val Ile Ala Asp Asp Phe Thr Gly Ala Thr Asp
1               5                   10                  15

Ile Ala Ser Phe Leu Val Glu Asn Gly Leu Pro Thr Val Gln Ile Asn
            20                  25                  30

Gly Val Pro Thr Gly Lys Met Pro Glu Ala Ile Asp Ala Leu Val Ile
        35                  40                  45

Ser Leu Lys Thr Arg Ser Cys Pro Val Val Glu Ala Thr Gln Gln Ser
    50                  55                  60

Leu Ala Ala Leu Ser Trp Leu Gln Gln Gln Gly Cys Lys Gln Ile Tyr
65                  70                  75                  80

Phe Lys Tyr Cys Ser Thr Phe Asp Ser Thr Ala Lys Gly Asn Ile Gly
                85                  90                  95

Pro Val Thr Asp Ala Leu Met Asp Ala Leu Asp Thr Pro Phe Thr Val
            100                 105                 110

Phe Ser Pro Ala Leu Pro Val Asn Gly Arg Thr Val Tyr Gln Gly Tyr
        115                 120                 125

Leu Phe Val Met Asn Gln Leu Leu Ala Glu Ser Gly Met Arg His His
    130                 135                 140

Pro Val Asn Pro Met Thr Asp Ser Tyr Leu Pro Arg Leu Val Glu Ala
```

```
         145                 150                 155                 160
    Gln Ser Thr Gly Arg Cys Gly Val Val Ser Ala His Val Phe Glu Gln
                    165                 170                 175
    Gly Val Asp Ala Val Arg Gln Glu Leu Ala Arg Leu Gln Gln Glu Gly
                180                 185                 190
    Tyr Arg Tyr Ala Val Leu Asp Ala Leu Thr Glu His His Leu Glu Ile
                195                 200                 205
    Gln Gly Glu Ala Leu Arg Asp Ala Pro Leu Val Thr Gly Gly Ser Gly
    210                 215                 220
    Leu Ala Ile Gly Leu Ala Arg Gln Trp Ala Gln Glu Asn Gly Asn Gln
    225                 230                 235                 240
    Ala Arg Glu Ala Gly His Pro Leu Ala Gly Arg Gly Val Val Leu Ser
                    245                 250                 255
    Gly Ser Cys Ser Gln Met Thr Asn Arg Gln Val Ala His Tyr Arg Gln
                260                 265                 270
    Ile Ala Pro Ala Arg Glu Val Asp Val Ala Arg Cys Leu Ser Thr Glu
                275                 280                 285
    Thr Leu Ala Ala Tyr Ala His Glu Leu Ala Glu Trp Val Leu Gly Gln
                290                 295                 300
    Glu Ser Val Leu Ala Pro Leu Val Phe Ala Thr Ala Ser Thr Asp Ala
    305                 310                 315                 320
    Leu Ala Ala Ile Gln Gln Gln Tyr Gly Ala Gln Lys Ala Ser Gln Ala
                    325                 330                 335
    Val Glu Thr Leu Phe Ser Gln Leu Ala Ala Arg Leu Ala Ala Glu Gly
                340                 345                 350
    Val Thr Arg Phe Ile Val Ala Gly Gly Glu Thr Ser Gly Val Val Thr
                355                 360                 365
    Gln Ser Leu Gly Ile Lys Gly Phe His Ile Gly Pro Thr Ile Ser Pro
                    370                 375                 380
    Gly Val Pro Trp Val Asn Ala Leu Asp Lys Pro Val Ser Leu Ala Leu
    385                 390                 395                 400
    Lys Ser Gly Asn Phe Gly Asp Glu Ala Phe Phe Ser Arg Ala Gln Arg
                    405                 410                 415
    Glu Phe Leu Ser
                420

<210> SEQ ID NO 25
<211> LENGTH: 4029
<212> TYPE: DNA
<213> ORGANISM: Escherichia coli

<400> SEQUENCE: 25
atggtttact cctataccga gaaaaaacgt attcgtaagg attttggtaa acgtccacaa      60
gttctggatg taccttatct cctttctatc cagcttgact cgtttcagaa atttatcgag     120
caagatcctg aagggcagta tggtctggaa gctgctttcc gttccgtatt cccgattcag     180
agctacagcg gtaattccga gctgcaatac gtcagctacc gccttggcga accggtgttt     240
gacgtccagg aatgtcaaat ccgtggcgtg acctattccg caccgctgcg cgttaaactg     300
cgtctggtga tctatgagcg cgaagcgccg gaaggcaccg taaagacat taaagaacaa     360 gaagtctaca tgggcgaaat tccgctcatg acagacaacg gtacctttgt tatcaacggt     420
actgagcgtg ttatcgtttc ccagctgcac cgtagtccgg cgtcttctt tgactccgac     480 aaaggtaaaa cccactcttc gggtaaagtg ctgtataacg cgcgtatcat cccttaccgt     540
```

-continued

```
ggttcctggc tggacttcga attcgatccg aaggacaacc tgttcgtacg tatcgaccgt      600
cgccgtaaac tgcctgcgac catcattctg cgcgccctga actacaccac agagcagatc      660
ctcgacctgt tctttgaaaa agttatcttt gaaatccgtg ataacaagct gcagatggaa      720
ctggtgccgg aacgcctgcg tggtgaaacc gcatcttttg catcgaagc taacggtaaa       780 gtgtacgtag aaaaaggccg ccgtatcact gcgcgccaca ttcgccagct ggaaaaagac      840
gacgtcaaac tgatcgaagt cccggttgag tacatcgcag gtaaagtggt tgctaaagac     900
tatattgatg agtctaccgg cgagctgatc tgcgcagcga acatggagct gagcctggat     960
ctgctggcta agctgagcca gtctggtcac aagcgtatcg aaacgctgtt caccaacgat    1020
ctggatcacg cccatatat ctctgaaacc ttacgtgtcg acccaactaa cgaccgtctg     1080
agcgcactgg tagaaatcta ccgcatgatg cgccctggcg agccgccgac tcgtgaagca     1140
gctgaaagcc tgttcgagaa cctgttcttc tccgaagacc gttatgactt gtctgcggtt     1200
ggtcgtatga agttcaaccg ttctctgctg cgcgaagaaa tcgaaggttc cggtatcctg     1260
agcaaagacg acatcattga tgttatgaaa aagctcatcg atatccgtaa cggtaaaggc     1320
gaagtcgatg atatcgacca cctcggcaac cgtcgtatcc gttccgttgg cgaaatggcg     1380
gaaaaccagt tccgcgttgg cctggtacgt gtagagcgtg cggtgaaaga gcgtctgtct     1440
ctgggcgatc tggatacct gatgccacag gatatgatca acgccaagcc gatttccgca     1500
gcagtgaaag agttcttcgg ttccagccag ctgtctcagt ttatggacca gaacaacccg    1560
ctgtctgaga ttacgcacaa acgtcgtatc tccgcactcg gcccaggcgg tctgacccgt     1620
gaacgtgcag gcttcgaagt tcgagacgta cacccgactc actacggtcg cgtatgtcca     1680
atcgaaaccc ctgaaggtcc gaacatcggt ctgatcaact ctctgtccgt gtacgcacag     1740
actaacgaat acgcttcct tgagactccg tatcgtaaag tgaccgacgg tgttgtaact     1800
gacgaaattc actacctgtc tgctatcgaa gaaggcaact acgttatcgc ccaggcgaac     1860
tccaacttgg atgaagaagg ccacttcgta gaagacctgg taacttgccg tagcaaaggc     1920
gaatccagct tgttcagccg cgaccaggtt gactacatgg acgtatccac ccagcaggtg    1980
gtatccgtcg gtgcgtccct gatcccgttc ctggaacacg atgacgccaa ccgtgcattg     2040
atgggtgcga acatgcaacg tcaggccgtt ccgactctgc gcgctgataa gccgctggtt     2100
ggtactggta tggaacgtgc tgttgccgtt gactccggtg taactgcggt agctaaacgt     2160
ggtggtgtcg ttcagtacgt ggatgcttcc cgtatcgtta tcaaagttaa cgaagacgag     2220
atgtatccgg gtgaagcagg tatcgacatc tacaacctga ccaaatacac ccgttctaac     2280
cagaacacct gtatcaacca gatgccgtgt gtgtctctgg gtgaaccggt tgaacgtggc     2340
gacgtgctgg cagacggtcc gtccaccgac ctcggtgaac tggcgcttgg tcagaacatg     2400
cgcgtagcgt tcatgccgtg gaatggttac aacttcgaag actccatcct cgtatccgag     2460
cgtgttgttc aggaagaccg tttcaccacc atccacattc aggaactggc gtgtgtgtcc     2520
cgtgacacca gctgggtcc ggaagagatc accgctgaca tcccgaacgt gggtgaagct     2580
gcgctctcca aactggatga atccggtatc gtttacattg gtgcggaagt gaccggtggc     2640
gacattctgg ttggtaaggt aacgccgaaa ggtgaaactc agctgacccc agaagaaaaa     2700
ctgctgcgtg cgatcttcgg tgagaaagcc tctgacgtta agactcttc tctgcgcgta     2760 ccaaacggtg tatccggtac ggttatcgac gttcaggtct ttactcgcga tggcgtagaa     2820
aaagacaaac gtcgctgga atcgaagaa atgcagctca acaggcgaa gaaagacctg      2880 tctgaagaac tgcagatcct cgaagcgggt ctgttcagcc gtatccgtgc tgtgctggta     2940
```

```
gccggtggcg ttgaagctga aagctcgac aaactgccgc gcgatcgctg gctggagctg    3000
ggcctgacag acgaagagaa acaaaatcag ctggaacagc tggctgagca gtatgacgaa    3060
ctgaaacacg agttcgagaa gaaactcgaa gcgaaacgcc gcaaaatcac ccagggcgac    3120
gatctggcac cgggcgtgct gaagattgtt aaggtatatc tggcggttaa acgccgtatc    3180
cagcctggtg acaagatggc aggtcgtcac ggtaacaagg gtgtaatttc taagatcaac    3240
ccgatcgaag atatgcctta cgatgaaaac ggtacgccgg tagacatcgt actgaacccg    3300
ctgggcgtac cgtctcgtat gaacatcggt cagatcctcg aaacccacct gggtatggct    3360
gcgaaaggta tcggcgacaa gatcaacgcc atgctgaaaac agcagcaaga agtcgcgaaa    3420
ctgcgcgaat tcatccagcg tgcgtacgat ctgggcgctg acgttcgtca gaaagttgac    3480
ctgagtacct tcagcgatga agaagttatg cgtctggctg aaaacctgcg caaaggtatg    3540
ccaatcgcaa cgccggtgtt cgacggtgcg aaagaagcag aaattaaaga gctgctgaaa    3600
cttggcgacc tgccgacttc cggtcagatc cgcctgtacg atggtcgcac tggtgaacag    3660
ttcgagcgtc cggtaaccgt tggttacatg tacatgctga aactgaacca cctggtcgac    3720
gacaagatgc acgcgcgttc caccggttct tacagcctgg ttactcagca gccgctgggt    3780
ggtaaggcac agttcggtgg tcagcgtttc ggggagatgg aagtgtgggc gctggaagca    3840
tacggcgcag catacaccct gcaggaaatg ctcaccgtta agtctgatga cgtgaacggt    3900
cgtaccaaga tgtataaaaa catcgtggac ggcaaccatc agatggagcc gggcatgcca    3960
gaatccttca acgtattgtt gaaagagatt cgttcgctgg gtatcaacat cgaactggaa    4020
gacgagtaa                                                             4029
```

<210> SEQ ID NO 26
<211> LENGTH: 1342
<212> TYPE: PRT
<213> ORGANISM: Escherichia coli

<400> SEQUENCE: 26

```
Met Val Tyr Ser Tyr Thr Glu Lys Lys Arg Ile Arg Lys Asp Phe Gly
1               5                   10                  15

Lys Arg Pro Gln Val Leu Asp Val Pro Tyr Leu Leu Ser Ile Gln Leu
            20                  25                  30

Asp Ser Phe Gln Lys Phe Ile Glu Gln Asp Pro Glu Gly Gln Tyr Gly
        35                  40                  45

Leu Glu Ala Ala Phe Arg Ser Val Phe Pro Ile Gln Ser Tyr Ser Gly
    50                  55                  60

Asn Ser Glu Leu Gln Tyr Val Ser Tyr Arg Leu Gly Glu Pro Val Phe
65                  70                  75                  80

Asp Val Gln Glu Cys Gln Ile Arg Gly Val Thr Tyr Ser Ala Pro Leu
                85                  90                  95

Arg Val Lys Leu Arg Leu Val Ile Tyr Glu Arg Glu Ala Pro Glu Gly
            100                 105                 110

Thr Val Lys Asp Ile Lys Glu Gln Glu Val Tyr Met Gly Glu Ile Pro
        115                 120                 125

Leu Met Thr Asp Asn Gly Thr Phe Val Ile Asn Gly Thr Glu Arg Val
    130                 135                 140

Ile Val Ser Gln Leu His Arg Ser Pro Gly Val Phe Phe Asp Ser Asp
145                 150                 155                 160

Lys Gly Lys Thr His Ser Ser Gly Lys Val Leu Tyr Asn Ala Arg Ile
                165                 170                 175
```

```
Ile Pro Tyr Arg Gly Ser Trp Leu Asp Phe Glu Phe Asp Pro Lys Asp
            180                 185                 190

Asn Leu Phe Val Arg Ile Asp Arg Arg Lys Leu Pro Ala Thr Ile
            195                 200                 205

Ile Leu Arg Ala Leu Asn Tyr Thr Thr Glu Gln Ile Leu Asp Leu Phe
            210                 215                 220

Phe Glu Lys Val Ile Phe Glu Ile Arg Asp Asn Lys Leu Gln Met Glu
225                 230                 235                 240

Leu Val Pro Glu Arg Leu Arg Gly Glu Thr Ala Ser Phe Asp Ile Glu
                245                 250                 255

Ala Asn Gly Lys Val Tyr Val Glu Lys Gly Arg Arg Ile Thr Ala Arg
                260                 265                 270

His Ile Arg Gln Leu Glu Lys Asp Asp Val Lys Leu Ile Glu Val Pro
            275                 280                 285

Val Glu Tyr Ile Ala Gly Lys Val Ala Lys Asp Tyr Ile Asp Glu
            290                 295                 300

Ser Thr Gly Glu Leu Ile Cys Ala Ala Asn Met Glu Leu Ser Leu Asp
305                 310                 315                 320

Leu Leu Ala Lys Leu Ser Gln Ser Gly His Lys Arg Ile Glu Thr Leu
                325                 330                 335

Phe Thr Asn Asp Leu Asp His Gly Pro Tyr Ile Ser Glu Thr Leu Arg
            340                 345                 350

Val Asp Pro Thr Asn Asp Arg Leu Ser Ala Leu Val Glu Ile Tyr Arg
            355                 360                 365

Met Met Arg Pro Gly Glu Pro Pro Thr Arg Glu Ala Ala Glu Ser Leu
            370                 375                 380

Phe Glu Asn Leu Phe Phe Ser Glu Asp Arg Tyr Asp Leu Ser Ala Val
385                 390                 395                 400

Gly Arg Met Lys Phe Asn Arg Ser Leu Leu Arg Glu Glu Ile Glu Gly
                405                 410                 415

Ser Gly Ile Leu Ser Lys Asp Asp Ile Ile Asp Val Met Lys Lys Leu
            420                 425                 430

Ile Asp Ile Arg Asn Gly Lys Gly Glu Val Asp Asp Ile Asp His Leu
            435                 440                 445

Gly Asn Arg Arg Ile Arg Ser Val Gly Glu Met Ala Glu Asn Gln Phe
            450                 455                 460

Arg Val Gly Leu Val Arg Val Glu Arg Ala Val Lys Glu Arg Leu Ser
465                 470                 475                 480

Leu Gly Asp Leu Asp Thr Leu Met Pro Gln Asp Met Ile Asn Ala Lys
                485                 490                 495

Pro Ile Ser Ala Ala Val Lys Glu Phe Phe Gly Ser Ser Gln Leu Ser
            500                 505                 510

Gln Phe Met Asp Gln Asn Asn Pro Leu Ser Glu Ile Thr His Lys Arg
            515                 520                 525

Arg Ile Ser Ala Leu Gly Pro Gly Gly Leu Thr Arg Glu Arg Ala Gly
            530                 535                 540

Phe Glu Val Arg Asp Val His Pro Thr His Tyr Gly Arg Val Cys Pro
545                 550                 555                 560

Ile Glu Thr Pro Glu Gly Pro Asn Ile Gly Leu Ile Asn Ser Leu Ser
                565                 570                 575

Val Tyr Ala Gln Thr Asn Glu Tyr Gly Phe Leu Glu Thr Pro Tyr Arg
            580                 585                 590
```

-continued

```
Lys Val Thr Asp Gly Val Val Thr Asp Glu Ile His Tyr Leu Ser Ala
            595                 600                 605

Ile Glu Glu Gly Asn Tyr Val Ile Ala Gln Ala Asn Ser Asn Leu Asp
    610                 615                 620

Glu Glu Gly His Phe Val Glu Asp Leu Val Thr Cys Arg Ser Lys Gly
625                 630                 635                 640

Glu Ser Ser Leu Phe Ser Arg Asp Gln Val Asp Tyr Met Asp Val Ser
                645                 650                 655

Thr Gln Gln Val Val Ser Val Gly Ala Ser Leu Ile Pro Phe Leu Glu
                660                 665                 670

His Asp Asp Ala Asn Arg Ala Leu Met Gly Ala Asn Met Gln Arg Gln
            675                 680                 685

Ala Val Pro Thr Leu Arg Ala Asp Lys Pro Leu Val Gly Thr Gly Met
    690                 695                 700

Glu Arg Ala Val Ala Val Asp Ser Gly Val Thr Ala Val Ala Lys Arg
705                 710                 715                 720

Gly Gly Val Val Gln Tyr Val Asp Ala Ser Arg Ile Val Ile Lys Val
                725                 730                 735

Asn Glu Asp Glu Met Tyr Pro Gly Glu Ala Gly Ile Asp Ile Tyr Asn
                740                 745                 750

Leu Thr Lys Tyr Thr Arg Ser Asn Gln Asn Thr Cys Ile Asn Gln Met
            755                 760                 765

Pro Cys Val Ser Leu Gly Glu Pro Val Glu Arg Gly Asp Val Leu Ala
    770                 775                 780

Asp Gly Pro Ser Thr Asp Leu Gly Glu Leu Ala Leu Gly Gln Asn Met
785                 790                 795                 800

Arg Val Ala Phe Met Pro Trp Asn Gly Tyr Asn Phe Glu Asp Ser Ile
                805                 810                 815

Leu Val Ser Glu Arg Val Val Gln Glu Asp Arg Phe Thr Thr Ile His
                820                 825                 830

Ile Gln Glu Leu Ala Cys Val Ser Arg Asp Thr Lys Leu Gly Pro Glu
            835                 840                 845

Glu Ile Thr Ala Asp Ile Pro Asn Val Gly Glu Ala Ala Leu Ser Lys
    850                 855                 860

Leu Asp Glu Ser Gly Ile Val Tyr Ile Gly Ala Glu Val Thr Gly Gly
865                 870                 875                 880

Asp Ile Leu Val Gly Lys Val Thr Pro Lys Gly Glu Thr Gln Leu Thr
                885                 890                 895

Pro Glu Glu Lys Leu Leu Arg Ala Ile Phe Gly Glu Lys Ala Ser Asp
                900                 905                 910

Val Lys Asp Ser Ser Leu Arg Val Pro Asn Gly Val Ser Gly Thr Val
            915                 920                 925

Ile Asp Val Gln Val Phe Thr Arg Asp Gly Val Glu Lys Asp Lys Arg
    930                 935                 940

Ala Leu Glu Ile Glu Glu Met Gln Leu Lys Ala Lys Lys Asp Leu
945                 950                 955                 960

Ser Glu Glu Leu Gln Ile Leu Glu Ala Gly Leu Phe Ser Arg Ile Arg
                965                 970                 975

Ala Val Leu Val Ala Gly Gly Val Glu Ala Glu Lys Leu Asp Lys Leu
                980                 985                 990

Pro Arg Asp Arg Trp Leu Glu Leu  Gly Leu Thr Asp Glu  Glu Lys Gln
            995                 1000                1005

Asn Gln  Leu Glu Gln Leu Ala  Glu Gln Tyr Asp Glu  Leu Lys His
```

| | | | | | | | | | | |
|---|---|---|---|---|---|---|---|---|---|---|
| | | 1010 | | | 1015 | | | 1020 | | |

Glu Phe Glu Lys Lys Leu Glu Ala Lys Arg Arg Lys Ile Thr Gln
1025      1030      1035

Gly Asp Asp Leu Ala Pro Gly Val Leu Lys Ile Val Lys Val Tyr
1040      1045      1050

Leu Ala Val Lys Arg Arg Ile Gln Pro Gly Asp Lys Met Ala Gly
1055      1060      1065

Arg His Gly Asn Lys Gly Val Ile Ser Lys Ile Asn Pro Ile Glu
1070      1075      1080

Asp Met Pro Tyr Asp Glu Asn Gly Thr Pro Val Asp Ile Val Leu
1085      1090      1095

Asn Pro Leu Gly Val Pro Ser Arg Met Asn Ile Gly Gln Ile Leu
1100      1105      1110

Glu Thr His Leu Gly Met Ala Ala Lys Gly Ile Gly Asp Lys Ile
1115      1120      1125

Asn Ala Met Leu Lys Gln Gln Gln Glu Val Ala Lys Leu Arg Glu
1130      1135      1140

Phe Ile Gln Arg Ala Tyr Asp Leu Gly Ala Asp Val Arg Gln Lys
1145      1150      1155

Val Asp Leu Ser Thr Phe Ser Asp Glu Glu Val Met Arg Leu Ala
1160      1165      1170

Glu Asn Leu Arg Lys Gly Met Pro Ile Ala Thr Pro Val Phe Asp
1175      1180      1185

Gly Ala Lys Glu Ala Glu Ile Lys Glu Leu Leu Lys Leu Gly Asp
1190      1195      1200

Leu Pro Thr Ser Gly Gln Ile Arg Leu Tyr Asp Gly Arg Thr Gly
1205      1210      1215

Glu Gln Phe Glu Arg Pro Val Thr Val Gly Tyr Met Tyr Met Leu
1220      1225      1230

Lys Leu Asn His Leu Val Asp Asp Lys Met His Ala Arg Ser Thr
1235      1240      1245

Gly Ser Tyr Ser Leu Val Thr Gln Gln Pro Leu Gly Gly Lys Ala
1250      1255      1260

Gln Phe Gly Gly Gln Arg Phe Gly Glu Met Glu Val Trp Ala Leu
1265      1270      1275

Glu Ala Tyr Gly Ala Ala Tyr Thr Leu Gln Glu Met Leu Thr Val
1280      1285      1290

Lys Ser Asp Asp Val Asn Gly Arg Thr Lys Met Tyr Lys Asn Ile
1295      1300      1305

Val Asp Gly Asn His Gln Met Glu Pro Gly Met Pro Glu Ser Phe
1310      1315      1320

Asn Val Leu Leu Lys Glu Ile Arg Ser Leu Gly Ile Asn Ile Glu
1325      1330      1335

Leu Glu Asp Glu
1340

<210> SEQ ID NO 27
<211> LENGTH: 4224
<212> TYPE: DNA
<213> ORGANISM: Escherichia coli

<400> SEQUENCE: 27
gtgaaagatt tattaaagtt tctgaaagcg cagactaaaa ccgaagagtt tgatgcgatc  60
aaaattgctc tggcttcgcc agacatgatc cgttcatggt ctttcggtga agttaaaaag  120

```
ccggaaaccca tcaactaccg tacgttcaaa ccagaacgtg acggccttttt ctgcgcccgt      180 atctttgggc cggtaaaaga ttacgagtgc ctgtgcggta agtacaagcg cctgaaacac      240
cgtggcgtca tctgtgagaa gtgcggcgtt gaagtgaccc agactaaagt acgccgtgag      300
cgtatgggcc acatcgaact ggcttccccg actgcgcaca tctggttcct gaaatcgctg      360
ccgtcccgta tcggtctgct gctcgatatg ccgctgcgcg atatcgaacg cgtactgtac      420
tttgaatcct atgtggttat cgaaggcggt atgaccaacc tggaacgtca gcagatcctg      480
actgaagagc agtatctgga cgcgctggaa gagttcggtg acgaattcga cgcgaagatg      540
ggggcggaag caatccaggc tctgctgaag agcatggatc tggagcaaga gtgcgaacag      600
ctgcgtgaag agctgaacga aaccaactcc gaaaccaagc gtaaaaagct gaccaagcgt      660
atcaaactgc tggaagcgtt cgttcagtct ggtaacaaac cagagtggat gatcctgacc      720
gttctgccgg tactgccgcc agatctgcgt ccgctggttc cgctggatgg tggtcgtttc      780
gcgacttctg acctgaacga tctgtatcgt cgcgtcatta accgtaacaa ccgtctgaaa      840
cgtctgctgg atctggctgc gccggacatc atcgtacgta acgaaaaacg tatgctgcag      900
gaagcggtag acgccctgct ggataacggt cgtcgcggtc gtgcgatcac cggttctaac      960
aagcgtcctc tgaaatcttt ggccgacatg atcaaaggta acagggtcg tttccgtcag     1020 aacctgctcg gtaagcgtgt tgactactcc ggtcgttctg taatcaccgt aggtccatac     1080
ctgcgtctgc atcagtgcgg tctgccgaag aaaatggcac tggagctgtt caaaccgttc     1140
atctacggca gctggaact gcgtggtctt gctaccacca ttaaagctgc gaagaaaatg     1200
gttgagcgcg aagaagctgt cgtttgggat atcctggacg aagttatccg cgaacacccg     1260
gtactgctga accgtgcacc gactctgcac cgtctgggta tccaggcatt gaaccggta     1320 ctgatcgaag gtaaagctat ccagctgcac ccgctggttt gtgcggcata taacgccgac     1380
ttcgatggtg accagatggc tgttcacgta ccgctgacgc tggaagccca gctggaagcg     1440
cgtgcgctga tgatgtctac caacaacatc ctgtccccgg cgaacggcga accaatcatc     1500
gttccgtctc aggacgttgt actgggtctg tactacatga cccgtgactg tgttaacgcc     1560
aaaggcgaag catggtgct gactggcccg aaagaagcag aacgtctgta tcgctctggt     1620
ctggcttctc tgcatgcgcg cgttaaagtg cgtatcaccg agtatgaaaa agatgctaac     1680
ggtgaattag tagcgaaaac cagcctgaaa gacacgactg ttggccgtgc cattctgtgg     1740
atgattgtac cgaaaggtct gccttactcc atcgtcaacc aggcgctggg taaaaaagca     1800
atctccaaaa tgctgaacac ctgctaccgc attctcggtc tgaaaccgac cgttattttt     1860
gcggaccaga tcatgtacac cggcttcgcc tatgcagcgc gttctggtgc atctgttggt     1920
atcgatgaca tggtcatccc ggagaagaaa acgaaatca tctccgaggc agaagcagaa     1980
gttgctgaaa ttcaggagca gttccagtct ggtctggtaa ctgcgggcga acgctacaac     2040
aaagttatcg atatctgggc tgcggcgaac gatcgtgtat ccaaagcgat gatggataac     2100
ctgcaaactg aaaccgtgat taaccgtgac ggtcaggaag agaagcaggt ttccttcaac     2160
agcatctaca tgatggccga ctccggtgcg cgtggttctg cggcacagat tcgtcagctt     2220
gctggtatgc gtggtctgat ggcgaagccg gatggctcca tcatcgaaac gccaatcacc     2280
gcgaacttcc gtgaaggtct gaacgtactc cagtacttca tctccaccca cggtgctcgt     2340
aaaggtctgg cggataccgc actgaaaact gcgaactccg ttacctgac tcgtcgtctg     2400 gttgacgtgg cgcaggacct ggtggttacc gaagacgatt gtggtaccca tgaaggtatc     2460
```

```
atgatgactc cggttatcga gggtggtgac gttaaagagc cgctgcgcga tcgcgtactg    2520
ggtcgtgtaa ctgctgaaga cgttctgaag ccgggtactg ctgatatcct cgttccgcgc    2580
aacacgctgc tgcacgaaca gtggtgtgac ctgctggaag agaactctgt cgacgcggtt    2640
aaagtacgtt ctgttgtatc ttgtgacacc gactttggtg tatgtgcgca ctgctacggt    2700
cgtgacctgg cgcgtggcca tcatcaac aagggtgaag caatcggtgt tatcgcggca      2760
cagtccatcg gtgaaccggg tacacagctg accatgcgta cgttccacat cggtggtgcg    2820
gcatctcgtg cggctgctga atccagcatc caagtgaaaa acaaaggtag catcaagctc    2880
agcaacgtga agtcggttgt gaactccagc ggtaaactgg ttatcacttc ccgtaatact    2940
gaactgaaac tgatcgacga attcggtcgt actaaagaaa gctacaaagt accttacggt    3000
gcggtactgg cgaaaggcga tggcgaacag gttgctggcg cgaaaccgt tgcaaactgg      3060
gacccgcaca ccatgccggt tatcaccgaa gtaagcggtt ttgtacgctt tactgacatg    3120
atcgacggcc agaccattac gcgtcagacc gacgaactga ccggtctgtc ttcgctggtg    3180
gttctggatt ccgcagaacg taccgcaggt ggtaaagatc tgcgtccggc actgaaaatc    3240
gttgatgctc agggtaacga cgttctgatc ccaggtaccg atatgccagc gcagtacttc    3300
ctgccgggta aagcgattgt tcagctggaa gatggcgtac agatcagctc tggtgacacc    3360
ctggcgcgta ttccgcagga atccggcggt accaaggaca tcaccggtgg tctgccgcgc    3420
gttgcggacc tgttcgaagc acgtcgtccg aaagagccgg caatcctggc tgaaatcagc    3480
ggtatcgttt ccttcggtaa agaaaccaaa ggtaaacgtc gtctggttat caccccggta    3540
gacggtagcg atccgtacga agagatgatt ccgaaatggc gtcagctcaa cgtgttcgaa    3600
ggtgaacgtg tagaacgtgg tgacgtaatt tccgacggtc cggaagcgcc gcacgacatt    3660
ctgcgtctgc gtggtgttca tgctgttact cgttacatcg ttaacgaagt acaggacgta    3720
taccgtctgc agggcgttaa gattaacgat aaacacatcg aagttatcgt tcgtcagatg    3780
ctgcgtaaag ctaccatcgt taacgcgggt agctccgact tcctggaagg cgaacaggtt    3840
gaatactctc gcgtcaagat cgcaaaccgc gaactggaag cgaacggcaa agtgggtgca    3900
acttactccc gcgatctgct gggtatcacc aaagcgtctc tggcaaccga gtccttcatc    3960
tccgcggcat cgttccagga gaccactcgc gtgctgaccg aagcagccgt tgcgggcaaa    4020
cgcgacgaac tgcgcggcct gaaagagaac gttatcgtgg gtcgtctgat cccggcaggt    4080
accggttacg cgtaccacca ggatcgtatg cgtcgccgtg ctgcgggtga agctccggct    4140
gcaccgcagg tgactgcaga agacgcatct gccagcctgg cagaactgct gaacgcaggt    4200
ctgggcggtt ctgataacga gtaa                                          4224
```

<210> SEQ ID NO 28
<211> LENGTH: 1407
<212> TYPE: PRT
<213> ORGANISM: Escherichia coli

<400> SEQUENCE: 28

Met Lys Asp Leu Leu Lys Phe Leu Lys Ala Gln Thr Lys Thr Glu Glu
1               5                   10                  15

Phe Asp Ala Ile Lys Ile Ala Leu Ala Ser Pro Asp Met Ile Arg Ser
            20                  25                  30

Trp Ser Phe Gly Glu Val Lys Lys Pro Glu Thr Ile Asn Tyr Arg Thr
        35                  40                  45

Phe Lys Pro Glu Arg Asp Gly Leu Phe Cys Ala Arg Ile Phe Gly Pro
    50                  55                  60

```
Val Lys Asp Tyr Glu Cys Leu Cys Gly Lys Tyr Lys Arg Leu Lys His
 65                  70                  75                  80

Arg Gly Val Ile Cys Glu Lys Cys Gly Val Glu Val Thr Gln Thr Lys
             85                  90                  95

Val Arg Arg Glu Arg Met Gly His Ile Glu Leu Ala Ser Pro Thr Ala
                100                 105                 110

His Ile Trp Phe Leu Lys Ser Leu Pro Ser Arg Ile Gly Leu Leu Leu
            115                 120                 125

Asp Met Pro Leu Arg Asp Ile Glu Arg Val Leu Tyr Phe Glu Ser Tyr
        130                 135                 140

Val Val Ile Glu Gly Gly Met Thr Asn Leu Arg Gln Gln Ile Leu
145                 150                 155                 160

Thr Glu Glu Gln Tyr Leu Asp Ala Leu Glu Glu Phe Gly Asp Glu Phe
                165                 170                 175

Asp Ala Lys Met Gly Ala Glu Ala Ile Gln Ala Leu Leu Lys Ser Met
                180                 185                 190

Asp Leu Glu Gln Glu Cys Glu Gln Leu Arg Glu Glu Leu Asn Glu Thr
        195                 200                 205

Asn Ser Glu Thr Lys Arg Lys Lys Leu Thr Lys Arg Ile Lys Leu Leu
210                 215                 220

Glu Ala Phe Val Gln Ser Gly Asn Lys Pro Glu Trp Met Ile Leu Thr
225                 230                 235                 240

Val Leu Pro Val Leu Pro Pro Asp Leu Arg Pro Leu Val Pro Leu Asp
                245                 250                 255

Gly Gly Arg Phe Ala Thr Ser Asp Leu Asn Asp Leu Tyr Arg Arg Val
            260                 265                 270

Ile Asn Arg Asn Asn Arg Leu Lys Arg Leu Leu Asp Leu Ala Ala Pro
        275                 280                 285

Asp Ile Ile Val Arg Asn Glu Lys Arg Met Leu Gln Glu Ala Val Asp
    290                 295                 300

Ala Leu Leu Asp Asn Gly Arg Arg Gly Arg Ala Ile Thr Gly Ser Asn
305                 310                 315                 320

Lys Arg Pro Leu Lys Ser Leu Ala Asp Met Ile Lys Gly Lys Gln Gly
                325                 330                 335

Arg Phe Arg Gln Asn Leu Leu Gly Lys Arg Val Asp Tyr Ser Gly Arg
                340                 345                 350

Ser Val Ile Thr Val Gly Pro Tyr Leu Arg Leu His Gln Cys Gly Leu
            355                 360                 365

Pro Lys Lys Met Ala Leu Glu Leu Phe Lys Pro Phe Ile Tyr Gly Lys
        370                 375                 380

Leu Glu Leu Arg Gly Leu Ala Thr Thr Ile Lys Ala Ala Lys Lys Met
385                 390                 395                 400

Val Glu Arg Glu Glu Ala Val Val Trp Asp Ile Leu Asp Glu Val Ile
                405                 410                 415

Arg Glu His Pro Val Leu Leu Asn Arg Ala Pro Thr Leu His Arg Leu
            420                 425                 430

Gly Ile Gln Ala Phe Glu Pro Val Leu Ile Glu Gly Lys Ala Ile Gln
        435                 440                 445

Leu His Pro Leu Val Cys Ala Ala Tyr Asn Ala Asp Phe Asp Gly Asp
    450                 455                 460

Gln Met Ala Val His Val Pro Leu Thr Leu Glu Ala Gln Leu Glu Ala
465                 470                 475                 480
```

-continued

```
Arg Ala Leu Met Met Ser Thr Asn Asn Ile Leu Ser Pro Ala Asn Gly
                485                 490                 495

Glu Pro Ile Ile Val Pro Ser Gln Asp Val Val Leu Gly Leu Tyr Tyr
            500                 505                 510

Met Thr Arg Asp Cys Val Asn Ala Lys Gly Glu Gly Met Val Leu Thr
        515                 520                 525

Gly Pro Lys Glu Ala Glu Arg Leu Tyr Arg Ser Gly Leu Ala Ser Leu
    530                 535                 540

His Ala Arg Val Lys Val Arg Ile Thr Glu Tyr Glu Lys Asp Ala Asn
545                 550                 555                 560

Gly Glu Leu Val Ala Lys Thr Ser Leu Lys Asp Thr Thr Val Gly Arg
                565                 570                 575

Ala Ile Leu Trp Met Ile Val Pro Lys Gly Leu Pro Tyr Ser Ile Val
            580                 585                 590

Asn Gln Ala Leu Gly Lys Lys Ala Ile Ser Lys Met Leu Asn Thr Cys
        595                 600                 605

Tyr Arg Ile Leu Gly Leu Lys Pro Thr Val Ile Phe Ala Asp Gln Ile
    610                 615                 620

Met Tyr Thr Gly Phe Ala Tyr Ala Ala Arg Ser Gly Ala Ser Val Gly
625                 630                 635                 640

Ile Asp Asp Met Val Ile Pro Glu Lys Lys His Glu Ile Ile Ser Glu
                645                 650                 655

Ala Glu Ala Glu Val Ala Glu Ile Gln Glu Gln Phe Gln Ser Gly Leu
            660                 665                 670

Val Thr Ala Gly Glu Arg Tyr Asn Lys Val Ile Asp Ile Trp Ala Ala
        675                 680                 685

Ala Asn Asp Arg Val Ser Lys Ala Met Met Asp Asn Leu Gln Thr Glu
    690                 695                 700

Thr Val Ile Asn Arg Asp Gly Gln Glu Glu Lys Gln Val Ser Phe Asn
705                 710                 715                 720

Ser Ile Tyr Met Met Ala Asp Ser Gly Ala Arg Gly Ser Ala Ala Gln
                725                 730                 735

Ile Arg Gln Leu Ala Gly Met Arg Gly Leu Met Ala Lys Pro Asp Gly
            740                 745                 750

Ser Ile Ile Glu Thr Pro Ile Thr Ala Asn Phe Arg Glu Gly Leu Asn
        755                 760                 765

Val Leu Gln Tyr Phe Ile Ser Thr His Gly Ala Arg Lys Gly Leu Ala
    770                 775                 780

Asp Thr Ala Leu Lys Thr Ala Asn Ser Gly Tyr Leu Thr Arg Arg Leu
785                 790                 795                 800

Val Asp Val Ala Gln Asp Leu Val Val Thr Glu Asp Cys Gly Thr
                805                 810                 815

His Glu Gly Ile Met Met Thr Pro Val Ile Glu Gly Gly Asp Val Lys
            820                 825                 830

Glu Pro Leu Arg Asp Arg Val Leu Gly Arg Val Thr Ala Glu Asp Val
        835                 840                 845

Leu Lys Pro Gly Thr Ala Asp Ile Leu Val Pro Arg Asn Thr Leu Leu
    850                 855                 860

His Glu Gln Trp Cys Asp Leu Leu Glu Glu Asn Ser Val Asp Ala Val
865                 870                 875                 880

Lys Val Arg Ser Val Val Ser Cys Asp Thr Asp Phe Gly Val Cys Ala
                885                 890                 895

His Cys Tyr Gly Arg Asp Leu Ala Arg Gly His Ile Ile Asn Lys Gly
```

-continued

```
              900             905             910
Glu Ala Ile Gly Val Ile Ala Ala Gln Ser Ile Gly Glu Pro Gly Thr
            915             920             925

Gln Leu Thr Met Arg Thr Phe His Ile Gly Gly Ala Ala Ser Arg Ala
            930             935             940

Ala Ala Glu Ser Ser Ile Gln Val Lys Asn Lys Gly Ser Ile Lys Leu
945             950             955             960

Ser Asn Val Lys Ser Val Val Asn Ser Ser Gly Lys Leu Val Ile Thr
                965             970             975

Ser Arg Asn Thr Glu Leu Lys Leu Ile Asp Glu Phe Gly Arg Thr Lys
            980             985             990

Glu Ser Tyr Lys Val Pro Tyr Gly Ala Val Leu Ala Lys Gly Asp Gly
            995             1000            1005

Glu Gln Val Ala Gly Gly Glu Thr Val Ala Asn Trp Asp Pro His
        1010            1015            1020

Thr Met Pro Val Ile Thr Glu Val Ser Gly Phe Val Arg Phe Thr
        1025            1030            1035

Asp Met Ile Asp Gly Gln Thr Ile Thr Arg Gln Thr Asp Glu Leu
        1040            1045            1050

Thr Gly Leu Ser Ser Leu Val Val Leu Asp Ser Ala Glu Arg Thr
        1055            1060            1065

Ala Gly Gly Lys Asp Leu Arg Pro Ala Leu Lys Ile Val Asp Ala
        1070            1075            1080

Gln Gly Asn Asp Val Leu Ile Pro Gly Thr Asp Met Pro Ala Gln
        1085            1090            1095

Tyr Phe Leu Pro Gly Lys Ala Ile Val Gln Leu Glu Asp Gly Val
        1100            1105            1110

Gln Ile Ser Ser Gly Asp Thr Leu Ala Arg Ile Pro Gln Glu Ser
        1115            1120            1125

Gly Gly Thr Lys Asp Ile Thr Gly Gly Leu Pro Arg Val Ala Asp
        1130            1135            1140

Leu Phe Glu Ala Arg Arg Pro Lys Glu Pro Ala Ile Leu Ala Glu
        1145            1150            1155

Ile Ser Gly Ile Val Ser Phe Gly Lys Glu Thr Lys Gly Lys Arg
        1160            1165            1170

Arg Leu Val Ile Thr Pro Val Asp Gly Ser Asp Pro Tyr Glu Glu
        1175            1180            1185

Met Ile Pro Lys Trp Arg Gln Leu Asn Val Phe Glu Gly Glu Arg
        1190            1195            1200

Val Glu Arg Gly Asp Val Ile Ser Asp Gly Pro Glu Ala Pro His
        1205            1210            1215

Asp Ile Leu Arg Leu Arg Gly Val His Ala Val Thr Arg Tyr Ile
        1220            1225            1230

Val Asn Glu Val Gln Asp Val Tyr Arg Leu Gln Gly Val Lys Ile
        1235            1240            1245

Asn Asp Lys His Ile Glu Val Ile Val Arg Gln Met Leu Arg Lys
        1250            1255            1260

Ala Thr Ile Val Asn Ala Gly Ser Ser Asp Phe Leu Glu Gly Glu
        1265            1270            1275

Gln Val Glu Tyr Ser Arg Val Lys Ile Ala Asn Arg Glu Leu Glu
        1280            1285            1290

Ala Asn Gly Lys Val Gly Ala Thr Tyr Ser Arg Asp Leu Leu Gly
        1295            1300            1305
```

Ile Thr Lys Ala Ser Leu Ala Thr Glu Ser Phe Ile Ser Ala Ala
        1310                1315                1320

Ser Phe Gln Glu Thr Thr Arg Val Leu Thr Glu Ala Ala Val Ala
        1325                1330                1335

Gly Lys Arg Asp Glu Leu Arg Gly Leu Lys Glu Asn Val Ile Val
        1340                1345                1350

Gly Arg Leu Ile Pro Ala Gly Thr Gly Tyr Ala Tyr His Gln Asp
        1355                1360                1365

Arg Met Arg Arg Arg Ala Ala Gly Glu Ala Pro Ala Ala Pro Gln
        1370                1375                1380

Val Thr Ala Glu Asp Ala Ser Ala Ser Leu Ala Glu Leu Leu Asn
        1385                1390                1395

Ala Gly Leu Gly Gly Ser Asp Asn Glu
        1400                1405

<210> SEQ ID NO 29
<211> LENGTH: 720
<212> TYPE: DNA
<213> ORGANISM: Escherichia coli

<400> SEQUENCE: 29
atgcaagaga actacaagat tctggtggtc gatgacgaca tgcgcctgcg tgcgctgctg     60
gaacgttatc tcaccgaaca aggcttccag gttcgaagcg tcgctaatgc agaacagatg    120
gatcgcctgc tgactcgtga atctttccat cttatggtac tggatttaat gttacctggt    180
gaagatggct tgtcgatttg ccgacgtctt cgtagtcaga gcaaccccgat gccgatcatt    240 atggtgacgg cgaaagggga agaagtggac cgtatcgtag gcctggagat tggcgctgac    300
gactacattc aaaaccgtt taacccgcgt gaactgctgg cccgtatccg tgcggtgctg    360
cgtcgtcagg cgaacgaact gccaggcgca ccgtcacagg aagaggcggt aattgctttc    420
ggtaagttca aacttaacct cggtacgcgc gaaatgttcc gcgaagacga gccgatgccg    480
ctcaccagcg gtgagtttgc ggtactgaag gcactggtca gccatccgcg tgagccgctc    540
tcccgcgata gctgatgaa ccttgcccgt ggtcgtgaat attccgcaat ggaacgctcc    600
atcgacgtgc agatttcgcg tctgcgccgc atggtggaag aagatccagc gcatccgcgt    660
tacattcaga ccgtctgggg tctgggctac gtctttgtac cggacggctc taaagcatga    720

<210> SEQ ID NO 30
<211> LENGTH: 239
<212> TYPE: PRT
<213> ORGANISM: Escherichia coli

<400> SEQUENCE: 30

Met Gln Glu Asn Tyr Lys Ile Leu Val Val Asp Asp Met Arg Leu
  1               5                  10                  15

Arg Ala Leu Leu Glu Arg Tyr Leu Thr Glu Gln Gly Phe Gln Val Arg
            20                  25                  30

Ser Val Ala Asn Ala Glu Gln Met Asp Arg Leu Leu Thr Arg Glu Ser
        35                  40                  45

Phe His Leu Met Val Leu Asp Leu Met Leu Pro Gly Glu Asp Gly Leu
    50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
                85                  90                  95

Ile Gly Ala Asp Asp Tyr Ile Pro Lys Pro Phe Asn Pro Arg Glu Leu
            100                 105                 110

Leu Ala Arg Ile Arg Ala Val Leu Arg Arg Gln Ala Asn Glu Leu Pro
        115                 120                 125

Gly Ala Pro Ser Gln Glu Glu Ala Val Ile Ala Phe Gly Lys Phe Lys
    130                 135                 140

Leu Asn Leu Gly Thr Arg Glu Met Phe Arg Glu Asp Glu Pro Met Pro
145                 150                 155                 160

Leu Thr Ser Gly Glu Phe Ala Val Leu Lys Ala Leu Val Ser His Pro
                165                 170                 175

Arg Glu Pro Leu Ser Arg Asp Lys Leu Met Asn Leu Ala Arg Gly Arg
            180                 185                 190

Glu Tyr Ser Ala Met Glu Arg Ser Ile Asp Val Gln Ile Ser Arg Leu
        195                 200                 205

Arg Arg Met Val Glu Glu Asp Pro Ala His Pro Arg Tyr Ile Gln Thr
    210                 215                 220

Val Trp Gly Leu Gly Tyr Val Phe Val Pro Asp Gly Ser Lys Ala
225                 230                 235

<210> SEQ ID NO 31
<211> LENGTH: 672
<212> TYPE: DNA
<213> ORGANISM: Escherichia coli

<400> SEQUENCE: 31
atgcgcgtac tggttgttga agacaatgcg ttgttacgtc accaccttaa agttcagatt      60
caggatgctg gtcatcaggt cgatgacgca gaagatgcca agaagccga ttattatctc     120 aatgaacata taccggatat tgcgattgtc gatctcggat tgccagacga ggacggtctg     180
tcactgattc gccgctggcg tagcaacgat gtttcactgc cgattctggt attaaccgcc     240
cgtgaaagct ggcaggacaa agtcgaagta ttaagtgccg gtgctgatga ttatgtgact     300
aaaccgtttc atattgaaga ggtgatggcg cgaatgcagg cattaatgcg gcgtaatagc     360
ggtctggctt cacaggtcat ttcgctcccc ccgtttcagg ttgatctctc tcgccgtgaa     420
ttatctatta tgacgaagt gatcaaactg accgcgttcg aatacactat tatggaaacg     480
ttgatacgca ataatggcaa agtggtcagc aaagattcgt taatgctcca actctatccg     540
gatgcggagc tgcgggaaag ccataccatt gatgtactga tgggacgtct gcgcaaaaaa     600
attcaggcac aatatccca agaagtgatt accaccgttc gcggccaggg ctatctgttc     660
gaattgcgct ga                                                        672

<210> SEQ ID NO 32
<211> LENGTH: 223
<212> TYPE: PRT
<213> ORGANISM: Escherichia coli

<400> SEQUENCE: 32

Met Arg Val Leu Val Val Glu Asp Asn Ala Leu Leu Arg His His Leu
1               5                   10                  15

Lys Val Gln Ile Gln Asp Ala Gly His Gln Val Asp Asp Ala Glu Asp
            20                  25                  30

Ala Lys Glu Ala Asp Tyr Tyr Leu Asn Glu His Ile Pro Asp Ile Ala
        35                  40                  45

Ile Val Asp Leu Gly Leu Pro Asp Glu Asp Gly Leu Ser Leu Ile Arg
    50                  55                  60

```
Arg Trp Arg Ser Asn Asp Val Ser Leu Pro Ile Leu Val Leu Thr Ala
 65              70                  75                  80

Arg Glu Ser Trp Gln Asp Lys Val Glu Val Leu Ser Ala Gly Ala Asp
             85                  90                  95

Asp Tyr Val Thr Lys Pro Phe His Ile Glu Glu Val Met Ala Arg Met
            100             105                 110

Gln Ala Leu Met Arg Arg Asn Ser Gly Leu Ala Ser Gln Val Ile Ser
            115             120                 125

Leu Pro Pro Phe Gln Val Asp Leu Ser Arg Arg Glu Leu Ser Ile Asn
    130             135             140

Asp Glu Val Ile Lys Leu Thr Ala Phe Glu Tyr Thr Ile Met Glu Thr
145             150                 155                 160

Leu Ile Arg Asn Asn Gly Lys Val Val Ser Lys Asp Ser Leu Met Leu
                165             170                 175

Gln Leu Tyr Pro Asp Ala Glu Leu Arg Glu Ser His Thr Ile Asp Val
            180             185                 190

Leu Met Gly Arg Leu Arg Lys Lys Ile Gln Ala Gln Tyr Pro Gln Glu
        195             200                 205

Val Ile Thr Thr Val Arg Gly Gln Gly Tyr Leu Phe Glu Leu Arg
    210             215                 220

<210> SEQ ID NO 33
<211> LENGTH: 12
<212> TYPE: DNA
<213> ORGANISM: Artificial Sequence
<220> FEATURE:
<223> OTHER INFORMATION: Primer Sequence

<400> SEQUENCE: 33
ctgtctctta ta                                                                12
```

METHODS FOR THE PRODUCTION OF METHACRYLATES

CROSS REFERENCE TO RELATED APPLICATIONS

This application is a § 371 national phase application of PCT Application No. PCT/GB2019/051427, filed on May 23, 2019, which claims priority to British Application No. 1808424.4 filed on May 23, 2018, the entire contents of each of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 1553.8 Sequence_ST25.txt, 97,895 bytes in size, generated on Nov. 2, 2020 and filed via EFS-Web, is provided in lieu of a paper copy. This Sequence Listing is hereby incorporated herein by reference into the specification for its disclosure.

INTRODUCTION

Methyl methacrylate (MMA) is an important monomer in the chemical industry. The principal use of MMA is in the production of plastics for various applications; however, MMA can also be used in bone cements for use in orthopaedic surgery. The most significant polymerisation application is the casting, moulding or extrusion of polymethyl methacrylate (PMMA) to produce high optical clarity plastics. The global consumption of PMMA is estimated at approximately 2.1 million tonnes per annum.

Although the most widely used methacrylate ester is MMA, methacrylic acid or MMA can also be used to produce other methacrylate esters either by direct esterification or by transesterification, respectively. Examples are butyl 2-methylprop-2-enoate (BMA, a methacrylate ester with the chemical formula $C_8H_{14}O_2$), isobutyl methacrylate (iBMA), ethyl methacrylate (EMA) and 2-ethylhexyl methacrylate (2EHMA). BMA is produced from the transesterification of MMA with butanol. All of these esters and PMMA have a wide variety of applications, namely in manufacturing textiles, coatings and adhesives, packaging, lubricants, automotive equipment, LCD screens, medical equipment and household goods.

MMA is currently produced solely by chemical means and current methods for the production of MMA include the acetone cyanohydrin (ACH) route and other routes starting from various $C_2$-$C_4$ precursors. One of the most successful methods for producing MMA is the 'Alpha process' whereby MMA is obtained from the ester, methyl propionate, by anhydrous reaction with formaldehyde. In the Alpha process, the methyl propionate is produced by the carbonylation of ethylene. This ethylene feedstock is derived from fossil fuels. The Alpha process offers many advantages compared to other processes commonly used in the production of MMA. These advantages include a reduction in the use of hazardous chemicals, much higher product selectivity, and a reduced reliance on crude oil derived feedstocks. However, the pricing of the feedstock is linked to the cost of gasoline. It would therefore be desirable to develop an alternative process for the production of MMA which overcomes these deficiencies.

Microorganisms can be used to produce high value chemicals via fermentation, rather than by chemical synthesis. Recombinant DNA technology and synthetic metabolic engineering of such microorganisms has allowed for the reconstruction of metabolic pathways towards the production of specific chemicals. Several sustainable routes towards the bioproduction of acrylates have recently been undergoing development. These methods have generally focused on the production of acrylates from renewable feedstocks via microbial fermentation. For example, WO2016/185211 describes a process for producing methacrylic acid and/or derivatives thereof using recombinant microorganisms.

However, at certain concentrations, accumulation of acrylates such as MMA and BMA during fermentation is generally toxic to the biocatalysts, inhibiting cell growth and/or resulting in cell death. In particular, higher alkyl methacrylates (such as butyl methacrylate (BMA)) are more toxic than lower alkyl methacrylates such as MMA. This can therefore be a limiting factor for the biological production of alkyl methacrylates using microorganisms, in particular at large industrial scale.

It is known that bacteria are able to adapt to environmental stimuli, in particular by adapting regulatory networks that control gene expression. Several such networks exist, including the oxidative stress response and the multidrug resistance system.

In view of the toxic effect of alkyl methacrylates on microorganisms, and the given disadvantages associated with current chemical processes for producing MMA, it would be advantageous to provide microorganisms with improved tolerance to methacrylates for use in methods for the production of alkyl methacrylates.

It is therefore an object of the present invention to obviate or mitigate one or more of these problems, to provide an improved process for the production of methacrylates, in particular BMA and/or MMA and to provide microorganisms with improved tolerance to methacrylates.

SUMMARY

As further described in the examples, the inventors have employed various strategies to select for microorganisms that have acquired resistance to methacrylates upon exposure to methacrylate in culture. Surprisingly, the inventors were able to isolate bacterial strains that survived in the presence of phase separated methacrylates, at a concentration that is usually toxic to wild type bacteria. The resistant strains were isolated and sequenced to identify genetic mutations compared to the wild type that confer resistance. The resistant strains were also further characterised. Knock in and knock out strains were also developed to further assess the mutations responsible for the observed resistance. The inventors found that the mutations which imparted tolerance resided in certain genes encoding components and regulators of the oxidative stress response and the bacterial multidrug resistance system, amongst others. The inventors also found that a combination of certain mutations could enhance the tolerance effect. Thus, the mutations identified can be used to confer tolerance to bacteria by genetically manipulating wild type bacteria to introduce said mutations.

The inventors have thus surprisingly identified, isolated and characterised bacterial strains that are more resistant to methacrylates than wild type bacteria and which can therefore be used in methods for the production of such compounds. Thus, the inventors have demonstrated that mutations in the oxidative stress response and the bacterial multidrug resistance system and its regulators play a crucial role in mediating resistance to methacrylates. In particular, the inventors have shown that mutants of the Acriflavine resistance regulator (acrR) confer tolerance to methacrylates, in particular when combined with one of the global regulators selected from marR, soxR or rob. The inventors have also identified the components and regulators of the oxidative stress response and the bacterial multidrug resistance system which contribute to the observed resistance thus enabling ways to genetically modify microorganisms to confer increased tolerance to methacrylates. Genetically modified microorganisms with increased tolerance to methacrylates are therefore within the scope of the invention. The inventors have also developed a process for the production of methacrylates using a genetically modified microorganism with increased tolerance to methacrylates.

FIGURES

The invention is further described in the following non-limiting figures.

FIG. 1. Effect of the absence [■] or presence [●] of 20% (v/v) BMA on the growth of E. coli. E. coli MG1655 (A), E. coli MG1655 soxR(R20H) (B), E. coli MG1655 soxR(R20H)acrR(V29G) (C), E. coli MG1655 soxR(R20H)acrR(T32fs) (D) were grown in MSX medium, in 250 mL shake flasks at 37° C. and 250 rpm shaking. Means of two replicates are shown and error bars are standard deviations.

Figure 2:
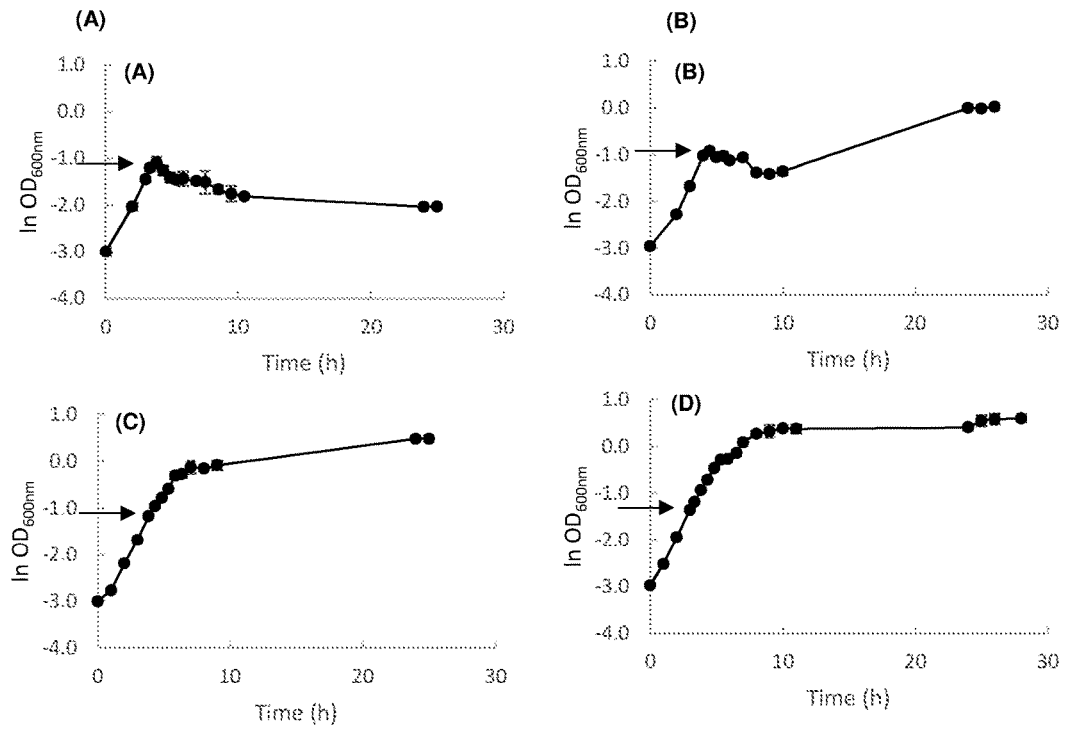

FIG. 2. Effect of the addition of 20% (v/v) BMA during mid exponential phase on the growth of E. coli strains. Shown growth of (A) E. coli MG1655, (B) E. coli MG1655 soxR(R20H), (C) E. coli MG1655 soxR(R20H)acrR(V29G) and (D) E. coli MG1655 soxR(R20H)acrR(T32fs). All strains were grown in 250 mL shake flasks in MSX medium at 37° C. and 250 rpm. BMA or $H_2O$ were added after reaching an OD600 nm of approximately 0.3. Samples were taken at different time intervals to determine the OD600 nm. Means of three replicates are shown and error bars are standard deviations.

Figure 3:
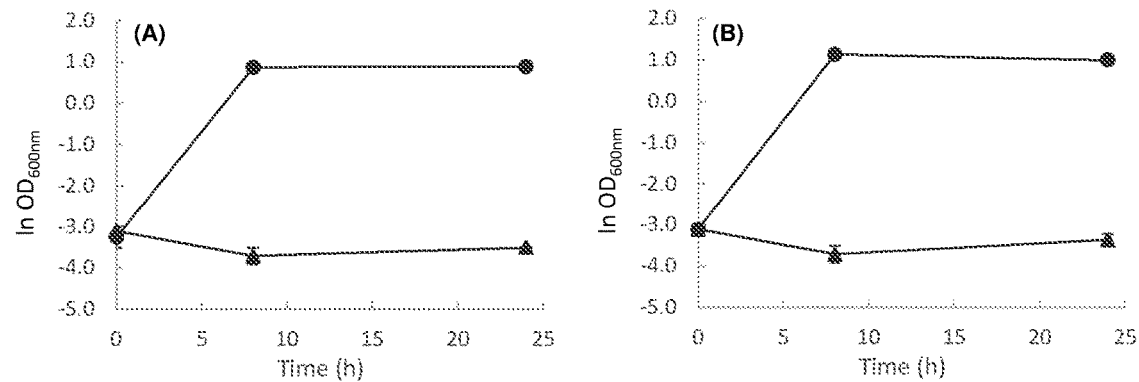

FIG. 3. Effect of the absence [●] or presence [▲] of 20% (v/v) BMA added immediately after inoculation on the growth of single deletants. E. coli BW25115 ΔsoxR (A) and E. coli BW25115 ΔacrR (B) were grown in MSX medium in 30 mL vials at 37° C. and 250 rpm shaking. Samples were taken at 0, 8 and 24 h to determine the OD600 nm. Means of two replicates are shown and error bars are standard deviations.

Figure 4:
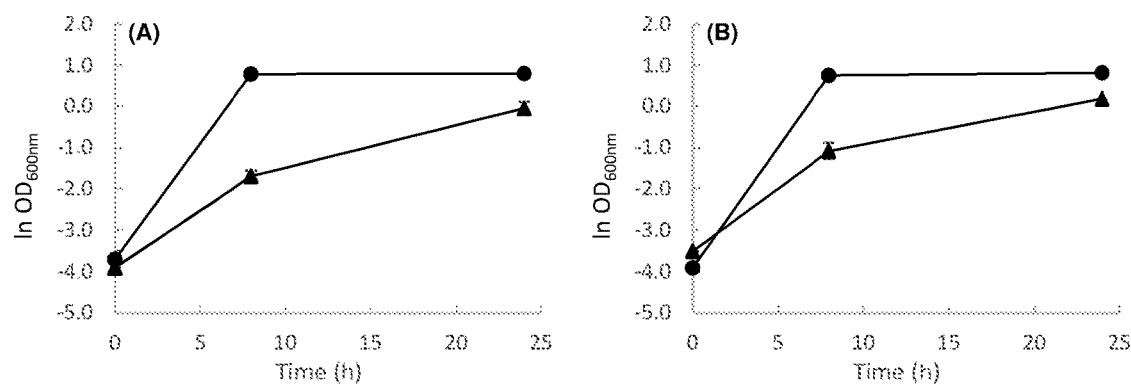

FIG. 4. Effect of the absence [●] or presence [▲] of 20% (v/v) BMA added immediately after inoculation on the growth of single mutation strains. E. coli MG1655 acrR (V29G) (A) and E. coli MG1655 acrR(T32fs) (B) were grown in MSX medium in 30 mL vials at 37° C. and 250 rpm shaking. Samples were taken at 0, 8 and 24 h to determine the OD600 nm. Means of two replicates are shown and error bars are standard deviations.

FIGS. 5a-5k, a) Effect of BMA at low concentrations. Growth of E. coli BW 25113 with BMA at 0% (□), 0.01% (◇), 0.05% (Δ), and 0.1% (x) v/v in M9 minimal medium at 37° C. and 200 RPM using 250 mL conical flasks with 50 mL media. b) Effect of BMA at high concentrations. Growth of E. coli BW 25113 with BMA at 0% (□), 0.5% (◇), 1.0% (Δ), 5.0% (○), 10.0% (x), and 20.0% (+) v/v in M9 minimal medium at 37° C. and 200 RPM using 250 mL conical flasks with 50 mL media. c) Test for inherent tolerance of E. coli towards BMA. Growth of E. coli BW 25113 with BMA at 0% (□), 0.1% (x), 0.5% (*), 0.1% after subculture (◇), 0.5% after subculture (Δ) v/v in M9 minimal medium at 37° C. and 200 RPM using 250 mL conical flasks with 50 mL media (in triplicates). d) ADE-1. Adaptive evolution in serial batch cultures with sequential increases in BMA concentration. E. coli was grown in M9 minimal medium with 10 g L-1 glucose and BMA at 37° C. and 200 RPM in 50 mL FALCON® tubes with 10 mL media in 3 parallel tubes tube 1 (Solid Line), tube 2 (dotted line), and tube 3 (dashed line). BMA concentration was increased in each sequential transfer at 0.1% BMA (x), 0.5% BMA (□), 1% BMA (◇), 5% (Δ), 10% (○), and 20% (+) using the best growing culture as starting culture for each of the 3 tubes. e) ADE-3. Adaptive evolution in serial batch cultures, with 5 serial cultures in each BMA concentration. E. coli was grown in M9 minimal medium with 10 g L-1 glucose and BMA at 37° C. and 200 RPM in 50 mL FALCON® tubes with 10 mL media in 3 parallel tubes tube 1 (Solid Line), tube 2 (dotted line), and tube 3 (dashed line). BMA concentration was increased from 0.1% v/v (x) to 0.5% v/v(□), 1% v/v (◇), 5% v/v(Δ), 10% v/v (*), and 20% v/v(○) using each separate tube as starting culture for subsequent transfer. f) ADE-3. Adaptive evolution in serial batch cultures, with 1 serial cultures at 0.1% v/v BMA, 2 serial transfers at 10% v/v BMA, and 45 serial transfer at 20% v/v BMA. E. coli was grown in M9 minimal medium with 10 g L-1 glucose and BMA at 37° C. and 200 RPM in 50 mL FALCON® tubes with 10 mL media in 3 parallel tubes tube 1 (Solid Line), tube 2 (dotted line), and tube 3 (dashed line). BMA concentration was increased from 0.1% v/v (x) to 10% v/v(□) and 20% v/v (◇) using the best growing culture as starting culture for each of the 3 tubes. g) ADE-4 Adaptive evolution and selection of BMA tolerant E. coli in a chemostat. A Chemostat culture of E. coli in a mini-bioreactor (55 mL working volume) was grown in M9 minimal medium with 1 g L-1 glucose at 37° C. and aeration rate of ~0.3 L h-1 with BMA concentration (♦) gradually increased from 0-20% v/v and dilution rate (□) varied from 0 to 0.55 h-1. Cell concentration (●) was reported in cell dry weight g L-1. h) Growth of isolates from ADE-1 and ADE-2 in M9 minimal medium with 20% v/v BMA at 37° C. and 200 RPM using 250 mL conical flasks with 50 mL media (triplicates). Isolate 2 (Δ), 3 (◇), 5 (*), 6 (–), 7 (○), and Wild type with no BMA (- with dotted line). i) Growth of isolates from ADE-3 in M9 minimal medium with 20% v/v BMA at 37° C. and 200 RPM using 250 mL conical flasks with 50 mL media (triplicates). Isolate 14 (□), 15 (◇), 16 (Δ), 17 (x), 18 (○), and Wild type with no BMA (- with dotted line). j) Growth of isolates from ADE-4 at dilution rate of 0.33 h-1 in M9 minimal medium with 20% v/v BMA at 37° C. and 200 RPM using 250 mL conical flasks with 50 mL media (triplicates). Isolate 8 (□), 9 (◇), 10 (Δ), and Wild type with no BMA (- with dotted line). k) Growth of isolates from ADE-4 at dilution rate of 0.46 h-1 in M9 minimal medium with 20% v/v BMA at 37° C. and 200 RPM using 250 mL conical flasks with 50 mL media (triplicates). Isolate 19 (□), 20 (◇), 21(Δ), and Wild type with no BMA (- with dotted line).

Figure 6:
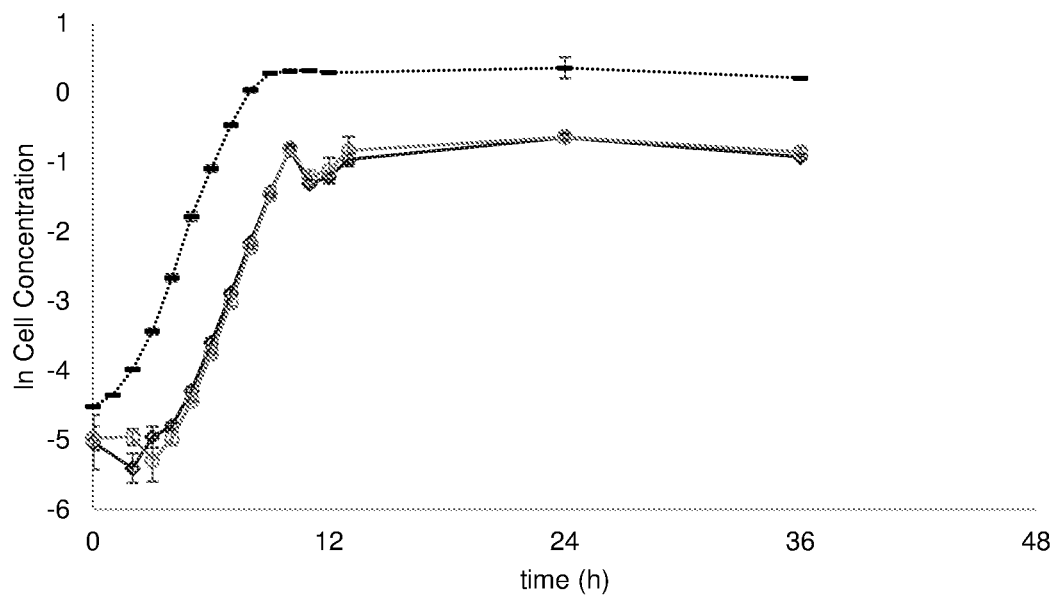

FIG. 6. Growth of isolates from adaptive evolution study at dilution rate of 0.55 h−1 in M9 minimal medium with 20% v/v BMA at 37° C. and 200 RPM using 250 mL conical flasks with 50 mL media (triplicates). Isolate 22 (◇), 23 (○) and Wild type with no BMA (- with dotted line).

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of microbiology, tissue culture, molecular biology, chemistry, biochemistry and recombinant DNA technology, which are within the skill of the art. Such techniques are explained fully in the literature, for example Green and Sambrook: Molecular Cloning: A Laboratory Manual, 4th edition, 2014.

Methods for Producing a Methacrylate, Conferring Tolerance to a Methacrylate to a Microorganism and Growing Methacrylate Tolerant Microorganisms In a first aspect, the invention relates to a method for the production of a methacrylate comprising
a) providing a genetically modified microorganism with increased tolerance to a $C_3$-$C_{12}$ methacrylate ester compared to the wild type microorganism in a fermentation medium and
b) growing the microorganism under conditions whereby a $C_3$-$C_{12}$ methacrylate ester is produced.

In a second aspect, the invention relates to a method for growing or maintaining a microorganism in the presence of a methacrylate comprising providing a genetically modified microorganism with increased tolerance to a $C_3$-$C_{12}$ methacrylate ester compared to a wild type microorganism in a fermentation medium under conditions whereby a $C_3$-$C_{12}$ methacrylate ester is produced.

The invention also relates to a method for conferring or increasing the tolerance of a microorganism to a methacrylate comprising introducing a mutation into a nucleic acid encoding a protein component and/or regulator of the oxidative stress response and the bacterial multidrug resistance systems.

As used herein the terms "tolerance" or "resistance" refer to a microorganism's ability to survive in the presence of a methacrylate, in particular in the presence of a $C_3$-$C_{12}$ methacrylate ester. In one embodiment, the tolerant microorganism can therefore be maintained at a concentration of a methacrylate which is toxic to a wild type microorganism. For example, the microorganism may survive and grow for at least about 2.5 hours longer, preferably, for at least about 5 hours longer, more preferably, for at least about 10 hours longer, most preferably, for at least about 20 hours longer in the presence of butyl methacrylate compared to the wild type microorganism. The survival and growth of the microorganism may be determined by any suitable method known in the art. Preferably, the survival and growth of the microorganism may be determined by measuring the optical density of the microorganism, more preferably the optical density of the microorganism measured at a wavelength of about 600 nm (OD600). For example, the microorganism of the present invention may have an OD600 of at least 0.5 for 2.5 hours longer, preferably, for at least about 5 hours longer, more preferably, for at least about 10 hours longer, most preferably, for at least about 20 hours longer in the presence of butyl methacrylate compared to the wild type microorganism. In another example, an increase in the OD from 0.01-0.1 to 0.15 to 3.0 indicates that the organism is growing. Suitably, the OD600 is measured in a suitable fermentation medium. It will be appreciated by a person skilled in the art that the optical density of the microorganism may be measured at a different wavelength depending upon the fermentation medium used.

In another embodiment, the tolerant microorganism is able to grow at a concentration of a methacrylate which causes death or growth arrest of a wild type microorganism.

The terms "tolerance" or "resistance" and "tolerant" or "resistant" are used interchangeably herein. A genetically modified organism as described herein is characterised by increased "tolerance" or "resistance" to a methacrylate, in particular a $C_3$-$C_{12}$ methacrylate ester, compared to the wild type microorganism which does not comprise the genetic modification(s).

In one embodiment of the aspects of the invention, the microorganism is tolerant to at least 10% to 30% v/v, for example 10, 11, 12, 13, 14, 15, 16, 17, 18, 19, 20% v/v $C_3$-$C_{12}$ methacrylate ester when grown in a liquid medium at about 37° C. Thus, according to various embodiments, the microorganism can be maintained in the presence of a methacrylate at a concentration of at least 10% to 30% v/v, for example 10, 11, 12, 13, 14, 15, 16, 17, 18, 19, 20% v/v $C_3$-$C_{12}$ methacrylate ester.

The terms "increase", "improve" or "enhance" or "increased", "improved", "enhanced" or "increased" are used interchangeably herein.

The term microorganism as used herein refers to a prokaryotic or eukaryotic cell or cells. In one embodiment, the microorganism is a prokaryotic cell. In one embodiment, the microorganism is a bacterium.

In one embodiment, the modified microorganism has a mutation in one or more proteins that regulate or form part of the oxidative stress response and the bacterial multidrug resistance systems, including for example members or regulators of efflux pumps, for example the AcrAB TolC efflux pump complex, and AraC family members identified in *E. coli* (and nucleic acids encoding such proteins). Components and regulators of the oxidative stress response and the bacterial multidrug resistance systems have been characterised in *Escherichia coli* and homologous complexes are found in other organisms, including in many Gram-negative species.

In one embodiment, the microorganism is a Gram negative bacterium. In one embodiment the Gram negative bacterium is of the Enterobacteriaceae family.

In one embodiment, examples of suitable bacteria within the scope of the invention includes enterobacteria belonging to proteobacteria of the genus *Escherichia, Enterobacter, Pantoea, Klebsiella, Serratia, Erwinia, Salmonella, Morganella*, or the like, so-called coryneform bacteria belonging to the genus *Brevibacterium, Corynebacterium* or *Microbacterium* and bacteria belonging to the genus *Alicyclobacillus, Bacillus, Hydrogenobacter, Methanococcus, Acetobacter, Acinetobacter, Agrobacterium, Axorhizobium, Azotobacter, Anaplasma, Bacteroides, Bartonella, Bordetella, Borrelia, Brucella, Burkholderia, Calymmatobacterium, Campylobacter, Chlamydia, Chlamydophila, Clostridium, Coxiella, Cupriavidus, Ehrlichia, Enterococcus, Francisella, Fusobacterium, Gardnerella, Haemophilus, Helicobacter, Klebsiella, Methanobacterium, Micrococcus, Moraxella, Mycobacterium, Mycoplasma, Neisseria, Pasteurella, Peptostreptococcus, Porphyromonas, Prevotella, Pseudomonas, Rhizobium, Rickettsia, Rochalimaea, Rothia, Shigella, Staphylococcus, Stenotrophomonas, Streptococcus, Treponema, Vibrio, Wolbachia, Yersinia*, or the like.

Exemplary bacteria include species selected from *Escherichia coli, Klebsiella oxytoca, Anaerobiospirillum succiniciproducens, Actinobacillus succinogenes, Mannheimia succiniciproducens, Rhizobium etli. Bacillus subtilis, Corynebacterium glutamicum, Gluconobacter oxydans, Zymomonas mobilis, Lactococcus lactis, Lactobacillus plantarum, Streptomyces coelicolor, Clostridium aceto-*

*butylicum, Pseudomonas fluorescens, Hydrogenobacter thermophilus, Methanococcus jannaschii* and *Pseudomonas putida*.

Preferably the bacterium is of the genus *Escherichia, Corynebacterium* or *Pseudomonas*. Preferably the bacterium is *Escherichia coli, Corynebacterium glutamicum. Pseudomonas fluorescens* or *Pseudomonas putida*.

Exemplary yeasts or fungi include those belonging to the genera *Saccharomyces, Schizosaccharomyces, Candida, Kluyveromyces, Aspergillus, Pichia, Crytpococcus*, or the like. Exemplary yeast or fungi species include those selected from *Saccharomyces cerevisiae, Schizosaccharomyces pombe, Kluyveromyces lactis, Kluyveromyces marxianus, Aspergillus terreus, Aspergillus niger, Pichia pastoris* or the like.

In one embodiment, suitable microorganisms are selected from the genera *Escherichia, Erwinia, Providencia*, and *Serratia*. Within the genus *Escherichia*, the species *Escherichia coli* can be used. Exemplary strains include *E. coli* B, *E. coli* C, *E. coli* W, or the like. In one embodiment, the microorganism is *E. coli*, for example a commercially available and/or fully characterized strain *E. coli*, such as K-12 MG1655, BW25113 or W3110.

While aspects and embodiments relating to bacterial cells herein typically refer to genes or proteins according to their designation in *E. coli*, for bacterial cells of another family or species, it is within the level of skill in the art to identify the corresponding gene or protein, e.g., the homolog, ortholog and/or paralog, in the other family or species, typically by identifying sequences having moderate (typically ≥30%) or high (typically ≥50%) identity to the *E. coli* sequence, preferably taking the function of the protein expressed by the gene and/or the locus of the gene in the genome into account. Tables 1a and b below set out the function of the protein encoded by each specific gene, its locus in the *E. coli* BW25113 genome and the SEQ ID number of the coding sequence. Sequences of the wild nucleic acids and encoded proteins are provided herein.

A skilled person would thus understand that the various aspects of the invention extend to mutant proteins and nucleic acid sequences in other microorganisms, preferably in bacteria, for example *E. coli* strains. Thus, reference is also made to regulators and components of the oxidative stress response and the bacterial multidrug resistance system and its regulators that are homologues of the *E. coli* proteins and nucleic acids. As used herein, a homologue of a nucleic acid sequence or amino acid sequence has at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the wild type nucleic acid or amino acid sequence.

"Identity" is a property of sequences that measures their similarity or relationship. The term "sequence identity" or "identity" as used in the present disclosure means the percentage of pair-wise identical residues—following (homologous) alignment of a sequence of a polypeptide of the disclosure with a sequence in question—with respect to the number of residues in the longer of these two sequences. Sequence identity is measured by dividing the number of identical amino acid residues by the total number of residues and multiplying the product by 100.

The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure.

Suitable homologues or orthologues can be identified by sequence comparisons and identifications of conserved domains using databases such as NCBI and Paint ensemble and alignment programmes known to the skilled person. The percentage of sequence homology or sequence identity can, for example, be determined herein using the program BLASTP.

Alignments can be carried out using suitable computer programs such as BLAST2.0, which stands for Basic Local Alignment Search Tool or ClustalW or any other suitable program which is suitable to generate sequence alignments. Accordingly, a wild-type nucleic acid or amino acid sequence can serve as "subject sequence" or "reference sequence", while the amino acid sequence of a mutant nucleic acid or amino acid sequence different from the wild-type described herein serves as "query sequence". The terms "reference sequence" and "wild-type sequence" are used interchangeably herein.

The terms "genetic modification" or "genetic engineering" broadly refer to manipulation of the genome or nucleic acids of a microorganism. Likewise, the term "genetically engineered" or "genetically modified" refers to a microorganism comprising a genome or nucleic acid that is different from the genome or nucleic acid of the wild type microorganism. For example, the genome or nucleic acid may be manipulated using methods of genetic modification such as, heterologous gene expression, gene or promoter insertion or deletion, nucleic acid mutation, altered gene expression or inactivation, enzyme engineering, random mutagenesis methods, gene shuffling, or codon optimization. In one embodiment, the "genetically engineered" or "genetically modified" microorganism refers to an isolated strain, for example of a bacterium, comprising a genome or nucleic acid that is different from the wild type microorganism.

For the purposes of the invention, a "mutant" or "genetically modified" microorganism is a microorganism that has been altered compared to a naturally occurring wild type (WT) microorganism.

As used herein, "mutated" refers to a nucleic acid or protein that is modified in the microorganism of the various aspects of the invention compared to the wild-type microorganism. A mutation in a nucleic acid sequence or amino acid sequence can be a deletion, insertion or substitution of one or more residue. Mutations in a nucleic acid sequence can lead to a missense mutation resulting in the substitution of a single amino acid in the protein. Alternatively, a mutation in a nucleic acid sequence can introduce a premature stop codon resulting in a truncated protein or a change in the subsequent amino acid sequence. A knock out mutation is a mutation that abolishes function of the protein.

A "mutant" or "genetically modified" microorganism are isolated from their natural environment. In one embodiment, a "mutant" or "genetically modified" microorganism is not found in nature.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene" or "gene sequence" is used broadly to refer to a DNA nucleic acid associated with a biological function. Thus, genes may include introns and exons as in the genomic sequence, or may comprise only a coding sequence as in cDNAs, and/or may include cDNAs in combination with regulatory sequences.

The terms "peptide", "polypeptide" and "protein" are used interchangeably herein and refer to amino acids in a polymeric form of any length, linked together by peptide bonds.

For the purposes of the invention, "transgenic", "transgene" or "recombinant" means that with regard to, for example, a nucleic acid sequence, an expression cassette, gene construct or a vector comprising the nucleic acid sequence or a microorganism transformed with a nucleic acid sequence, expression cassette or vector described herein, nucleic acid sequences encoding proteins useful in the methods of the invention are not located in their natural genetic environment or have been modified by recombinant methods. The natural genetic environment is understood as meaning the natural genomic or chromosomal locus in the original microorganism.

The term "heterologous" nucleic acid sequence or gene construct designates a nucleic acid sequence of gene construct that cannot usually be found in the organism.

The mutation in the mutant or modified gene according to the various aspect of the invention may reside in a gene that encodes a protein component or regulator of the oxidative stress response and the bacterial multidrug resistance system and its regulators, for example components or regulators of the AcrAB TolC efflux pump or members of the AraC family of proteins. For example, the mutation in the mutant or modified gene according to the various aspects of the invention may reside in a gene that encodes a protein of the AraC family of transcriptional regulators. In particular, the mutation may reside in a soxR nucleic acid sequence resulting in a mutant SoxR protein, an acrR nucleic acid sequence resulting in a mutant AcrR protein, a rob nucleic acid sequence resulting in a mutant Rob protein and/or a marR nucleic acid sequence resulting in a mutant MarR protein or combinations thereof. In particular, the inventors have shown that mutants of the Acriflavine resistance regulator (acrR) confer tolerance to methacrylates, in particular when combined with one of the global regulators selected from marR, soxR or rob.

Redox-Sensitive Transcriptional Activator (soxR)

In one embodiment, the genetically modified microorganism comprises a mutation in a soxR nucleic acid sequence. Thus, the genetically modified microorganism comprises a mutant soxR nucleic acid sequence compared to a wild type soxR nucleic acid sequence. The mutant soxR nucleic acid sequence encodes a mutant SoxR protein.

soxR encodes a regulator of the MerR family. In the absence of an oxidative stress signal, the SoxR homodimer binds to the promoter region of soxS and prevents enhanced transcription. When the SoxR cluster is oxidised, SoxR becomes an activator of soxS transcription.

The $E.$ $coli$ soxR nucleic acid sequence is shown in SEQ ID NO. 1. This encodes a protein as shown in SEQ ID NO. 2. The 17-kDa SoxR protein is composed of 154 amino acid residues and forms a homodimer, which contains a [2Fe-2S] cluster. It has a DNA binding domain (residues 1-80), a dimerization helix (residues 81-118), and a Fe—S cluster binding domain (residues 119-154). SoxR activation is mediated by oxidation of its Fe—S cluster, which leads to the enhanced transcription of soxS.

In one embodiment, the wild type soxR nucleic acid sequence comprises SEQ ID NO. 1 or a homologue thereof.

The homologue of a soxR nucleic acid sequence or SoxR amino acid sequence has at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the wild type nucleic acid or amino acid sequence represented by SEQ ID NO. 1 and SEQ ID NO. 2 respectively. Preferably, overall sequence identity is 85%, 86%, 87%, 88%, 89%, 90%, 91%, 92%, 93%, 94%, 95%, 96%, 97%, 98% or 99%. The overall sequence identity is determined using a global alignment algorithm known in the art, such as the Needleman Wunsch algorithm in the program GAP (GCG Wisconsin Package, Accelrys).

In one embodiment, the mutation in SoxR facilitates oxidation and/or DNA binding, which consequently increases transcription of the SoxR regulon, including SoxS.

In one embodiment, the microorganism comprises a mutant soxR nucleic acid sequence encoding a mutant SoxR protein with a mutation in the DNA binding domain (residues 1-80) or in the FE-S cluster domain (residues 119-154).

In one embodiment, the mutation in the SoxR protein is selected from one of the following: a substitution of R20 with another amino acid, a substitution of R20 with another amino acid, deletion of residue 146 (deletion of nucleic acid residues 435, 436, 437), or a truncation at residue 139 with reference SEQ ID NO. 2. In one embodiment, substitution of R20 is with H. In one embodiment, substitution of R20 is with L. Also within the scope of the invention are modifications at equivalent positions in homologues of SoxR in microorganisms other than $E.$ $coli$.

In one embodiment, the mutation is not a knock out mutation. In one embodiment, the mutation is a gain of function mutation. The altered protein is able to confer tolerance to methacrylate esters.

Acriflavine Resistance Regulator (acrR)

In one embodiment, the genetically modified microorganism comprises a mutation in an acrR nucleic acid sequence. Thus, the genetically modified microorganism comprises a mutant acrR nucleic acid sequence compared to a wild type acrR sequence. The mutant acrR nucleic acid sequence encodes a mutant AcrR protein.

AcrR regulates the expression of the acrRAB genes associated with the AcrAB-TolC multidrug efflux pump. AcrR homodimer acts as a repressor to acrAB operon by binding to its operator region and is released when an activator molecule binds on its C-terminal ligand binding domain, which allows transcription of acrAB. The acrAB operon encodes AcrA and AcrB, which cooperates with TolC to form the major multidrug efflux pump complex AcrAB-TolC.

AcrR is a dimeric two-domain molecule with an entirely helical architecture similar to members of the TetR family of transcriptional regulators. In $E.$ $coli$, the acrR gene encodes the 215 amino acid AcrR protein, which contains an N-terminal DNA binding domain (residues 7-51) and a C-terminal ligand binding domain (residues 55-204).

In one embodiment, the wild type acrR nucleic acid sequence comprises SEQ ID NO. 3 or a homologue thereof encoding SEQ ID NO. 4.

The homologue of a acrR nucleic acid sequence or AcrR amino acid sequence has at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97% 98%, or 99% overall sequence identity to the wild type nucleic acid or amino acid sequence represented by SEQ ID NO. 3 and SEQ ID NO. 4 respectively. Preferably, overall sequence identity is 85%, 86%, 87%, 88%, 89%, 90%, 91%, 92%, 93%, 94%, 95%, 96%, 97%, 98% or 99%. The overall sequence identity is determined using a global alignment algorithm known in the art, such as the Needleman Wunsch algorithm in the program GAP (GCG Wisconsin Package, Accelrys).

In one embodiment, the microorganism comprises a mutant acrR nucleic acid sequence encoding a mutant AcrR protein with a mutation in the DNA binding domain (residues 7-51) or in the ligand binding domain (residues 55-204).

In one embodiment, the mutation in AcrR is selected from one of the following: a substitution of V29 with another amino acid, a frameshift mutation at Y49, a frameshift mutation at A191 or a frameshift mutation at T32 with reference SEQ ID NO:4. In one embodiment, substitution of V29 is with G. Also within the scope of the invention are modifications at equivalent positions in homologues of AcrR in microorganisms other than *E. coli*.

In one embodiment, the mutation is not a knock out mutation. In one embodiment, the mutation is a gain of function mutation, i.e. a functional protein with altered function compared to the wild type is produced. The altered protein is able to confer tolerance to methacrylate esters.

Right Origin-Binding (Rob)

In one embodiment, the genetically modified microorganism comprises a mutation in a rob nucleic acid sequence. Thus, the genetically modified microorganism comprises a mutant rob nucleic acid sequence compared to a wild type rob sequence. The mutant rob nucleic acid sequence encodes a mutant Rob protein.

The Rob protein in *E. coli* consists of 289 amino acids with an N-terminal DNA binding domain (residues 1-120) and C-terminal domain (residues 121-189). The C-terminal domain is considered essential for preventing its degradation by the Lon protease as well as its activation-deactivation mechanism.

In one embodiment, the wild type rob nucleic acid sequence comprises SEQ ID NO. 5 or a homologue thereof encoding a protein having SEQ ID No. 6.

The homologue of a rob nucleic acid sequence or Rob amino acid sequence has at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97% 98%, or 99% overall sequence identity to the wild type nucleic acid or amino acid sequence represented by SEQ ID NO. 5 and SEQ ID NO. 6 respectively. Preferably, overall sequence identity is 85%, 86%, 87%, 88%, 89%, 90%, 91%, 92%, 93%, 94%, 95%, 96%, 97%, 98% or 99%. The overall sequence identity is determined using a global alignment algorithm known in the art, such as the Needleman Wunsch algorithm in the program GAP (GCG Wisconsin Package, Accelrys).

The mutations found in the BMA tolerant strains caused amino acid substitutions at amino acid residues 70 and 156, which is distant from the DNA binding site of Rob, but may affect the protein-protein interaction involved in self-sequestration or the specificity for activators. Such mutations would either increase the amount of free/active Rob or increase Rob's affinity towards BMA to allow activation or increase activation by BMA. Increased activity of Rob would then result in increased expression of multidrug resistance genes under its regulatory control that could aid in gaining tolerance towards BMA.

In one embodiment, the microorganism comprises a mutant rob nucleic acid sequence encoding a mutant Rob protein with a mutation in the N-terminal DNA binding domain (residues 1-120) and C-terminal domain (residues 121-189).

In one embodiment, the mutation in Rob is selected from one of the following: a substitution of A70, or a substitution of R156 with another amino acid in Rob with reference to SEQ ID NO. 6. In one embodiment, substitution of A70 is with V or T. In one embodiment, substitution of R156 is with H. Also within the scope of the invention are modifications at equivalent positions in homologues of Rob in microorganisms other than *E. coli.*

Multiple Antibiotic Resistance Protein (marR)

In one embodiment, the genetically modified microorganism comprises a mutation in a marR nucleic acid sequence. Thus, the genetically modified microorganism comprises a mutant marR nucleic acid sequence compared to a wild type marR sequence. The mutant marR nucleic acid sequence encodes a mutant MarR protein.

In *E. coli*, the protein product of the marR gene, MarR, is composed of 144 amino acid residues and contains an N-terminal domain, a C-terminal domain, DNA binding site (residue 55-100), and salicylate binding site (residue 70-86). MarR, as a homodimer, acts as a repressor to the marAB operon by binding to its promoter region. Its DNA binding/repressor activity is suppressed by the presence and binding of small molecules such as salicylate, plumbagin, 2,4-dinitrophenol, and menadione, which allows transcription of marA, marB, and marR.

In one embodiment, the wild type marR nucleic acid sequence comprises SEQ ID NO. 7 or a homologue thereof encoding a protein having SEQ ID No. 8.

The homologue of a marR nucleic acid sequence or MarR amino acid sequence has at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97% 98%, or 99% overall sequence identity to the wild type nucleic acid or amino acid sequence represented by SEQ ID NO. 7 and SEQ ID NO. 8 respectively. Preferably, overall sequence identity is 85%, 86%, 87%, 88%, 89%, 90%, 91%, 92%, 93%, 94%, 95%, 96%, 97%, 98%, or 99%. The overall sequence identity is determined using a global alignment algorithm known in the art, such as the Needleman Wunsch algorithm in the program GAP (GCG Wisconsin Package, Accelrys).

In one embodiment, the microorganism comprises a mutant marR nucleic acid sequence encoding a mutant MarR protein with a mutation in the DNA binding and salicylate binding domain (residue 55-100). For example, the mutation may result in a reduction in DNA binding affinity and/or enhancement of affinity towards BMA as an activator.

In one embodiment, the mutation in MarR is a substitution of V84 with another amino acid with reference to SEQ ID NO. 8. In one embodiment, substitution of V84 is with G. Also within the scope of the invention are modifications at an equivalent position in homologues of MarR in microorganisms other than *E. coli*.

In one embodiment, the microorganism has a mutation in the acrR nucleic acid sequence encoding a mutant AcrR protein, e.g. a protein with a mutation in the DNA binding domain (residues 7-51) or in the ligand binding domain (residues 55-204), in combination with a mutation in the nucleic acid sequence of any one of soxR, rob or marR. For example, the microorganisms may comprise a mutation in a acrR and soxR; acrR and rob or acrR and marR nucleic acid sequence. Further mutations, i.e. in other genes, may or may not be present.

In one embodiment, the microorganism may comprise a mutation in the acrR nucleic acid sequence encoding a mutant AcrR protein with a mutation in the DNA binding domain (residues 7-51) or in the ligand binding domain (residues 55-204), comprising one of a substitution of V29 with another amino acid, a frameshift mutation at Y49, a frameshift mutation at A191, or a frameshift mutation at T32 with reference SEQ ID NO:4, in combination with a mutation in soxR selected from any of the following: a substitution of R20 with another amino acid, a substitution of R20 with another amino acid, deletion of residue 146 (deletion of nucleic acid residues 435, 436, 437), or a truncation at residue 139 with reference SEQ ID NO. 2. In one embodiment, substitution of R20 is with H. In one embodiment, substitution of R20 is with L. For example, the microorganism may comprise nucleic acid sequences comprising one of the following combinations of mutations:

acrR(V29) and SoxR(R20 L)
acrR(Y49fs) and SoxR(R20 L)
acrR(A191 fs) and SoxR(R20 L)
acrR(T32fs) and SoxR(R20 L)
acrR(V29) and SoxR(R20H)
acrR(Y49fs) and SoxR(R20H)
acrR(A191 fs) and SoxR(R20H)
acrR(T32fs) and SoxR(R20H)
acrR(V29) and SoxR(146 del)
acrR(Y49fs) and SoxR(146 del)
acrR(A191 fs) and SoxR(146 del)
acrR(T32fs) and SoxR(146 del)
acrR(V29) and SoxR(Leu139X)
acrR(Y49fs) and SoxR(Leu139X)
acrR(A191 fs) and SoxR(Leu139X)
acrR(T32fs) and SoxR(Leu139X)

In one embodiment, the microorganism may comprise a mutation in the acrR nucleic acid sequence encoding a mutant AcrR protein with a mutation in the DNA binding domain (residues 7-51) or in the ligand binding domain (residues 55-204), comprising one of a substitution of V29 with another amino acid, a frameshift mutation at Y49, a frameshift mutation at A191, or a frameshift mutation at T32 with reference SEQ ID NO:4, in combination with a mutation in marR selected from a substitution of V84 with another amino acid with reference to SEQ ID NO. 8. In one embodiment, substitution of V84 is with G. For example, the microorganism may comprise nucleic acid sequences comprising one of the following combinations of mutations:

acrR(V29) and marR(V84G)
acrR(Y49fs) and marR(V84G)
acrR(A191fs) and marR(V84G)
acrR(T32fs) and marR(V84G)

In one embodiment, the microorganism may comprise mutation in the acrR nucleic acid sequence encoding a mutant AcrR protein with a mutation in the DNA binding domain (residues 7-51) or in the ligand binding domain (residues 55-204), comprising one of a substitution of V29 with another amino acid, a frameshift mutation at Y49, a frameshift mutation at A191, or a frameshift mutation at T32 with reference SEQ ID NO:4, in combination with a mutations in rob selected from any one of the following: a substitution of A70, or a substitution of R156 with another amino acid in Rob with reference to SEQ ID NO. 6. In one embodiment, substitution of A70 is with V or T. In one embodiment, substitution of R156 is with H. For example, the microorganism may comprise nucleic acid sequences comprising one of the following combinations of mutations:

acrR(V29) and rob(156H)
acrR(Y49fs) and rob (156H)
acrR(A191 fs) and rob (156H)
acrR(T32fs) and rob (156H)
acrR(V29) and rob (A70T)
acrR(Y49fs) and rob (A70T)
acrR(A191fs) and rob (A70T)
acrR(T32fs) and rob (A70T)
acrR(V29) and rob (A70V)
acrR(Y49fs) and rob (A70V)
acrR(A191fs) and rob (A70V)
acrR(T32fs) and rob (A70V)

For the above embodiments reference is made to certain mutations. As explained herein, these refer to positions in the *E. coli* protein sequences of the genes/protein mentioned (see SEQ ID Nos 2, 4, 6 and 8 respectively for the protein sequences).

In one embodiment, the microorganism may comprise a combination of two or more of the mutant nucleic acid sequences described above. For example, the microorganism may have a mutation in at least two nucleic acid sequences selected from a soxR, rob, acrR and a marR nucleic acid sequence or a homolog thereof. Thus, the microorganism may comprise a mutation in a soxR and a rob nucleic acid sequence, a soxR and an acrR nucleic acid sequence, a soxR and a marR nucleic acid sequence, a rob and an acrR nucleic acid sequence, a rob and a marR nucleic acid sequence or an acrR and a marR nucleic acid sequence or a homolog thereof.

In another embodiment, the microorganism may comprise a mutation in at least three nucleic acid sequences selected from a soxR, rob, acrR and a marR nucleic acid sequence or a homolog thereof. Thus, the microorganism may comprise a mutation in a soxR, acrR and a rob nucleic acid sequence or a homolog thereof. Thus, the microorganism may comprise a mutation in a soxR, acrR and a marR nucleic acid sequence or a homolog thereof. Thus, the microorganism may comprise a mutation in a rob, acrR and a marR nucleic acid sequence or a homolog thereof.

In another embodiment, the microorganism may comprise a mutation in four nucleic acid sequences selected from a soxR, rob, acrR and a marR nucleic acid sequence or a homolog thereof.

In one embodiment, the microorganism may comprises one or more genetic mutation selected from those shown in table 1a.

TABLE 1a

Mutations conferring increased tolerance to methacrylates

| Gene and database references SEQ ID Nos refer to the wild type gene sequence | Gene Description | Cellular Location | Genomic Coordinate in reference sequence (NCBI Reference Sequence: NZ_CP009273.1) | Nucleotide Change/Mutation Before → After | Effect of Nucleotide change; Length of Amino Acid Sequence |
|---|---|---|---|---|---|
| rob Nucleic acid NCBI Reference Sequence: NZ_CP009273.1 Protein UniProtKB - P0ACI0 SEQ ID NO. 5 | Right origin binding protein | Cyt | 4624661 | C → T | missense - Arg156His ; 289 |
| rob SEQ ID NO. 5 | Right origin binding protein | Cyt | 4624919 | G → A | missense - Ala70Val ; 289 |
| rob SEQ ID NO. 5 | Right origin binding (rob) protein | Cyt | 4624920 | C → T | missense - Ala70Thr ; 289 |
| rob SEQ ID NO. 1 | Right origin binding (rob) protein | Cyt | 4625592 | C → T | silent - Val85Val ; 289 |
| SoxR nucleic acid NCBI Reference Sequence: NC_000913.3 protein UniProtKB - P0ACS2 SEQ ID NO. 1 | Superoxide response regulon activator | Cyt | 4267455 | G → T | Missense- Arg20Leu ; 154 |
| SOXR SEQ ID NO. 1 | Superoxide response regulon activator | Cyt | 4267812 | T → A | Truncation- stops at Leu139 ; 154 |
| SOxR SEQ ID NO. 1 | Superoxide response regulon activator | Cyt | 4267830 | 3 bp Deletion | Removal of Ala146 without changing the succeeding sequence ; 154 |
| soxR SEQ ID NO. 1 | Superoxide response regulon activator | Cyt | 4267455 | G → A | Missense- Arg20His; 154 |
| marR SEQ ID NO. 17 | Multiple antibiotic resistance (mar) operon - repressor protein | Cyt | 1613627 | G → A | Missense- Val84Gly; 144 |
| acrR nucleic acid NCBI Reference Sequence: NC_000913.3 protein UniProtKB - P0ACS9 SEQ ID NO. 3 | acriflavine resistance regulator- acrAB operon repressor | Cyt | 481302 | T → G | Missense- Val29Gly; 215 |
| acrR SEQ ID NO. 3 | acriflavine resistance regulator- acrAB operon repressor | Cyt | 481310 | 1 bp deletion | Frameshift and truncation- stops at residue 73; 215 |
| acrR SEQ ID NO. 3 | acriflavine resistance regulator -acrAB operon repressor | Cyt | | Frameshift | Frameshift at position 49 Y |
| acrR SEQ ID NO. 3 | acriflavine resistance regulator -acrAB operon repressor | Cyt | | Frameshift | Frameshift at residue 191 A |

In one embodiment, the microorganism also comprises one or more further mutation, for example in a gene that encodes a protein component of the oxidative stress response or multidrug resistance system. In one embodiment, the mutation is in a rpo nucleic acid sequence, for example rpoB (SEQ ID NO 25) or rpoC (SEQ ID NO 27), ompR (SEQ ID NO 29), acrB (SEQ ID NO 9), yohJ (SEQ ID NO 11), torY (SEQ ID NO 13), ipxM (SEQ ID NO 15), dnaK (SEQ ID NO 17), grol SEQ ID NO 19), ilvN (SEQ ID NO 21), phop SEQ ID NO 31), ygbK(SEQ ID NO 23) or a homolog thereof. In another embodiment, no further modifications of the protein component or regulator of the oxidative stress response or multidrug resistance system are present.

In one embodiment, the one or more further mutation is selected from a genetic mutation listed in table 1b.

TABLE 1b

| Gene and database references SEQ ID Nos refer to the wild type gene sequence | Gene Description | Cellular Location | Genomic Coordinate (NCBI Reference Sequence: NZ_CP009273.1) | Nucleotide Change/ Mutation Before → After | Effect of Nucleotide change; Length of Amino Acid Sequence |
| --- | --- | --- | --- | --- | --- |
| acrB nucleic acid NCBI Reference Sequence: NZ_CP009273.1 protein UniProtKB - P31224 SEQ ID NO. 9 | Part of the acrAB-tolC multi-drug efflux complex | IM | 478518 | C → A | missense - Val448Leu ; 1049 |
| acrB SEQ ID NO. 9 | Part of the acrAB-tolC multi-drug efflux complex | IM | 477159 | C → T | missense - Thr379Ile; 1049 |
| yohJ nucleic acid NCBI Reference Sequence: NZ_CP009273.1 protein UniProtKB - P60632 SEQ ID NO. 11 | Membrane protein | IM | 2224428 | T → G | missense - Leu109Arg; 132 |
| torY nucleic acid NCBI Reference Sequence: NZ_CP009273.1 protein UniProtKB - P52005 SEQ ID NO. 13 | N-oxide and S-oxide reductase subunit | IM | 1952131 | C → T | missense - Ala87Thr ; 366 |
| IpxM nucleic acid NCBI Reference Sequence: NZ_CP009273.1 protein UniProtKB- P24205 SEQ ID NO. 15 | Myristoyl-acyl carrier protein dependent acyltransferase | IM | 1933628 | 20 bp deletion | change in amino acid sequence starting at position 275; 323 |
| dnak nucleic acid NCBI Reference Sequence: NZ_CP009273.1 protein UniProtKB - P0A6Y8 SEQ ID NO. 17 | Molecular chaperone (HSP70) | Cyt | 13292 | T → G | missense - Val377Gly ; 638 |
| groL nucleic acid NCBI Reference Sequence: NZ_CP009273.1 protein UniProtKB - P0A6F5 SEQ ID NO. 19 | Chaperonin groEL (HSP60) | Cyt | 4361677 | C → T | missense - Pro279Leu ; 548 |
| ilvN nucleic acid NCBI Reference Sequence: NZ_CP009273.1 protein UniProtKB - P0ADF8 SEQ ID NO. 21 | Acetolactate synthase isozyme 1 small subunit - Activity regulator | Cyt | 3844331 | C → T | missense - Cys41Tyr ; 96 |

TABLE 1b-continued

| Gene and database references SEQ ID Nos refer to the wild type gene sequence | Gene Description | Cellular Location | Genomic Coordinate (NCBI Reference Sequence: NZ_CP009273.1) | Nucleotide Change/ Mutation Before → After | Effect of Nucleotide change; Length of Amino Acid Sequence |
|---|---|---|---|---|---|
| ygbK nucleic acid NCBI Reference Sequence: NZ_CP009273.1 protein UniProtKB - B7LEF1 SEQ ID NO. 23 | Conserved protein unknown function | Uk | 2856574 | C → A | missense - Ala294Glu ; 388 |
| rpoB nucleic acid NCBI Reference Sequence: NZ_CP009273.1 protein UniProtKB - P0A8V2 SEQ ID NO. 25 | RNA polymerase β subunit | Cyt | 4174281 | A → C | missense - Thr1037Pro ; 1342 |
| rpoC NCBI Reference Sequence: NZ_CP009273.1 Protein UniProtKB - P0A8T7 SEQ ID NO. 27 | RNA polymerase β' subunit | Cyt | 4174281 | T → G | missense - Leu361Arg ; 1407 |
| rpoC SEQ ID NO. 27 | RNA polymerase β' subunit | Cyt | 4177637 | C → T | missense - Ala787Val; 1407 |
| rpoC SEQ ID NO. 27 | RNA polymerase β' subunit | Cyt | 4178500 | C → T | missense - Arg1075Cys ; 1407 |
| ompR nucleic acid NCBI Reference Sequence: NZ_CP009273.1 protein UniProtKB - P0AA16 SEQ ID NO. 29 | Outer membrane porin protein - activator | Cyt | 3529901 | G → T | missense - Arg15Ser ; 239 |
| phoP nucleic acid NCBI Reference Sequence: NZ_CP009273.1 protein UniProtKB - P23836 SEQ ID NO. 31 | Magnesium starvation regulon- regulator | Per | 1185871 | C → A | missense - Leu11Phe ; 223 |

In one embodiment, the microorganism is selected from a microorganism having one or more genetic mutation as listed below:
  rob(R156H)rpoC(L361R)ilvN(C41Y)ygbK(A294E) lpxM(168_185del);
  rob(R156H)ilvN(C41Y) phoP(L11F)acrB(V448 L);
  soxR(Leu139X)580116(G>T);
  ssoxR(A146 del));
  rob(A70V);
  rob(R156H)rpoB(T1037P) torY(A87T) acrR(49Yfs);
  rob(A70T)yohJ(L109R) dnaK(V377G) 927777(C>T) acrR(A191fs);
  marR(V84G)rpoC(R1075C)ompR(R15S) acrB(T379I);
  marR(V84G)rpoC(R1075C)ompR(R15S);
  marR(V84G)rpoC(R1075C) rpoC(A787V)ompR(R15S) acr8(V901I);
  rob(R156H)rpoB(T1037P) groL(P279 L)acrR(49Yfs) 1197659(C>A) or
  soxR(R20 L)rpoC(r1075C) 2133236(T>A)3915915 (T>G).

As explained herein, the mutations shown above can be introduced in a wild type organism to confer resistance to methacrylates. The nucleic acids described herein may be mutated by insertion, substitution or deletion of one or more nucleotides.

Techniques for the manipulation, including inactivation or knockout of target genes are well-known in the art. These techniques include gene target using vectors that target the gene of interest and which allow integration allows for integration of transgene at a specific site. The targeting construct is engineered to recombine with the target gene, which is accomplished by incorporating sequences from the gene itself into the construct. Recombination then occurs in the region of that sequence within the gene, resulting in the insertion of a foreign sequence to disrupt the gene. With its sequence interrupted, the altered gene will be translated into a non-functional protein, if it is translated at all. Other techniques include genome editing (targeted genome engineering) as described below. Mutations can also be introduced by exposing the microorganism to a mutagen. The mutagen may be fast neutron irradiation or a chemical mutagen, for example selected from the following non-limiting list: ethyl methanesulfonate (EMS), methylmethane sulfonate (MMS), N-ethyl-N-nitrosurea (ENU), triethylmelamine (1 'EM), N-methyl-N-nitrosourea (MNU), procarbazine, chlorambucil, cyclophosphamide, diethyl sulfate, acrylamide monomer, melphalan, nitrogen mustard, vincristine, dimethylnitosamine, N-methyl-N'-nitro-Nitrosoguanidine (MNNG), nitrosoguanidine, 2-aminopurine, 7, 12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9 [3-(ethyl-2-chloroethyl)aminopropylamino]acridine dihydrochloride (ICR-170) or formaldehyde.

Recently, genome editing techniques have emerged as alternative methods to conventional mutagenesis methods (such as physical and chemical mutagenesis) or methods using the expression of transgenes in plants to produce mutant plants with improved phenotypes that are important in agriculture. These techniques employ sequence-specific nucleases (SSNs) including zinc finger nucleases (ZFNs), transcription activator-like effector nucleases (TALENs), and the RNA-guided nuclease Cas9 (CRISPR/Cas9), which generate targeted DNA double-strand breaks (DSBs), which are then repaired mainly by either error-prone non-homologous end joining (NHEJ) or high-fidelity homologous recombination (HR). Targeted genome modification or targeted genome editing is a genome engineering technique that uses targeted DNA double-strand breaks (DSBs) to stimulate genome editing through homologous recombination (HR)-mediated recombination events. To achieve effective genome editing via introduction of site-specific DNA DSBs, four major classes of customizable DNA binding proteins can be used: meganucleases derived from microbial mobile genetic elements, ZF nucleases based on eukaryotic transcription factors, transcription activator-like effectors (TALEs) from *Xanthomonas* bacteria, and the RNA-guided DNA endonuclease Cas9 from the type II bacterial adaptive immune system CRISPR (clustered regularly interspaced short palindromic repeats). Meganuclease, ZF, and TALE proteins all recognize specific DNA sequences through protein-DNA interactions. Although meganucleases integrate its nuclease and DNA-binding domains, ZF and TALE proteins consist of individual modules targeting 3 or 1 nucleotides (nt) of DNA, respectively. ZFs and TALEs can be assembled in desired combinations and attached to the nuclease domain of FokI to direct nucleolytic activity toward specific genomic loci. Upon delivery into host cells via the bacterial type III secretion system, TAL effectors enter the nucleus, bind to effector-specific sequences in host gene promoters and activate transcription. Their targeting specificity is determined by a central domain of tandem, 33-35 amino acid repeats. This is followed by a single truncated repeat of 20 amino acids. The majority of naturally occurring TAL effectors examined have between 12 and 27 full repeats.

These repeats only differ from each other by two adjacent amino acids, their repeat-variable di-residue (RVD). The RVD that determines which single nucleotide the TAL effector will recognize: one RVD corresponds to one nucleotide, with the four most common RVDs each preferentially associating with one of the four bases. Naturally occurring recognition sites are uniformly preceded by a T that is required for TAL effector activity. TAL effectors can be fused to the catalytic domain of the FokI nuclease to create a TAL effector nuclease (TALEN) which makes targeted DNA double-strand breaks (DSBs) in vivo for genome editing. The use of this technology in genome editing is well described in the art, for example in U.S. Pat. Nos. 8,440,431, 8,440,432 and 8,450,471. Customized plasmids that can be used with the Golden Gate cloning method to assemble multiple DNA fragments. The Golden Gate method uses Type IIS restriction endonucleases, which cleave outside their recognition sites to create unique 4 bp overhangs. Cloning is expedited by digesting and ligating in the same reaction mixture because correct assembly eliminates the enzyme recognition site. Assembly of a custom TALEN or TAL effector construct and involves two steps: (i) assembly of repeat modules into intermediary arrays of 1-10 repeats and (ii) joining of the intermediary arrays into a backbone to make the final construct.

Another genome editing method that can be used according to the various aspects of the invention is CRISPR. The use of this technology in genome editing is well described in the art, for example in U.S. Pat. No. 8,697,359 and references cited herein. In short, CRISPR is a microbial nuclease system involved in defence against invading phages and plasmids. CRISPR loci in microbial hosts contain a combination of CRISPR-associated (Cas) genes as well as non-coding RNA elements capable of programming the specificity of the CRISPR-mediated nucleic acid cleavage (sgRNA). Three types (I-III) of CRISPR systems have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer). The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRN A: tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

Cas9 is thus the hallmark protein of the type II CRISPR-Cas system, and a large monomeric DNA nuclease guided to a DNA target sequence adjacent to the PAM (protospacer adjacent motif) sequence motif by a complex of two non-coding RNAs: CRIPSR RNA (crRNA) and trans-activating crRNA (tracrRNA). The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA. Heterologous expression of Cas9 together with an sgRNA can introduce site-specific double strand breaks (DSBs) into genomic DNA of live cells from various organisms. For applications in eukaryotic organisms, codon optimized versions of Cas9, which is originally from the bacterium *Streptococcus pyogenes*, have been used.

The single guide RNA (sgRNA) is the second component of the CRISPR/Cas system that forms a complex with the Cas9 nuclease. sgRNA is a synthetic RNA chimera created by fusing crRNA with tracrRNA. The sgRNA guide sequence located at its 5' end confers DNA target specificity. Therefore, by modifying the guide sequence, it is possible to create sgRNAs with different target specificities. The canonical length of the guide sequence is typically 20 bp.

Alternatively, global transcription machinery engineering (gTME) can provide an alternative and useful approach for strain improvement.

In one embodiment, mutants are isolated by selection of resistant mutants from populations of microorganisms by applying selection pressure with BMA. Populations of microorganisms are known to contain spontaneously occurring mutants at low frequencies (<1 in $10^6$), and the application of a selection pressure will result in overgrowth of the fittest mutants. For example, the selection pressure is applied by either gradually increasing the concentration of BMA or by adding high concentrations (10-30%) of BMA from the outset. The selection pressure can include (a) batch culture until growth is observed; (b) sequential batch culture for 2 or more transfers; (c) growth in chemostat culture with increasing concentrations of BMA and increasing dilution rate; (d) growth in pH-auxostat or turbidostat culture with increasing concentrations of BMA.

$C_3$-$C_{12}$ Methacrylate Esters

By the term $C_3$-$C_{12}$ methacrylate esters is generally meant a methacrylate comprising a $C_3$-$C_{12}$ alkyl, hydroxyalkyl, alkenyl, alkylaryl or alkenylaryl group including structural isomers thereof. The $C_3$-$C_{12}$ group may be cyclic, acyclic, or part cyclic, linear or branched, aliphatic, aromatic or part-aromatic/aliphatic. Preferably the $C_3$-$C_{12}$ methacrylate esters of the present invention may include, for example, n-propyl, isopropyl, isobutyl, n-butyl, t-butyl, isopentyl, hexyl, cyclohexyl, 2-ethylhexyl, decyl, dodecyl, hydroxyethyl, hydroxypropyl, isobornyl, allyl or cinnamyl methacrylate.

Preferably the $C_3$-$C_{12}$ methacrylate esters are $C_3$-$C_{12}$ alkyl methacrylates, more preferably, $C_3$-$C_8$ alkyl methacrylates for example n-propyl, isopropyl, isobutyl, n-butyl, isopentyl, hexyl, cyclohexyl, heptyl, octyl, 2-ethylhexyl, decyl or dodecyl methacrylate.

Preferably, the hydroxyalkyl methacrylates are hydroxyethyl or hydroxypropyl methacrylate.

In embodiments, the $C_3$-$C_{12}$ methacrylate esters are $C_3$-$C_{12}$ alkenylaryl methacrylates, for example cinnamyl methacrylate.

The $C_3$-$C_{12}$ alkyl methacrylates are more preferably $C_3$-$C_6$ alkyl methacrylates, such as the propyl, butyl or hexyl methacrylates, including for example, structural isomers thereof. More preferably, the $C_3$-$C_6$ alkyl methacrylates are propyl or butyl methacrylates, in particular isopropyl or n-butyl methacrylate.

In one embodiment, the $C_3$-$C_{12}$ methacrylate ester is butyl methacrylate (BMA).

For the production of MMA, the methods described herein may include the additional steps of c) removing the $C_3$-$C_{12}$ methacrylate ester from the fermentation medium and transesterifying the removed $C_3$-$C_{12}$ methacrylate ester with methanol, to produce methyl methacrylate.

In aspects and embodiments of the present invention, the microorganism may be genetically modified to produce more $C_3$-$C_{12}$ methacrylate ester than the wildtype. Thus, the microorganism has a mutation that renders it more tolerant to a methacrylate ester compared to the wild type as described herein and that is a modified to increase production of $C_3$-$C_{12}$ methacrylate ester compared to the wildtype, for example the microorganism carries a transgenic construct that expresses an enzyme of the $C_3$-$C_{12}$ methacrylate ester biosynthetic pathway.

Thus, the method for the production of a methacrylate as described herein may comprise a) providing a genetically modified microorganism with increased tolerance to a $C_3$-$C_{12}$ methacrylate ester compared to the wild type and that is further modified to increase production of $C_3$-$C_{12}$ methacrylate ester compared to a wild type in a fermentation medium and b) growing the microorganism under conditions whereby a $C_3$-$C_{12}$ methacrylate ester is produced.

Enhancing the production of $C_3$-$C_{12}$ methacrylate ester compared to a wildtype microorganism may include making modifications to existing cellular metabolic processes, nucleic acids and/or proteins by the use of various genetic engineering techniques known in the art. Enhancing the production of $C_3$-$C_{12}$ methacrylate ester may also include modifying the microorganism/s to express one or more heterologous genes in the microorganism/s. These may include genes encoding enzymes of the desired pathway to $C_3$-$C_{12}$ methacrylate ester from carbon based feedstocks, or may include other auxiliary genes which act to promote the functioning and expression of the enzymes in such pathways either directly or indirectly. Accordingly, in one embodiment, the microorganism may be modified to enhance production of $C_3$-$C_{12}$ methacrylate esters. One or more gene/s which may be expressed within the microorganism such that it is modified to produce $C_3$-$C_{12}$ methacrylate ester, preferably $C_3$-$C_{12}$ alkyl methacrylate, includes those encoding any of the following enzymes. Heterologous genes may be expressed by transforming the microorganism with a vector comprising the heterologous gene.

In embodiments, the microorganism may express one or more enzymes which can convert isobutyryl-CoA to methacrylyl-CoA, for example an oxidase, dehydrogenase or oxidoreductase.

The oxidase may be an oxidase acting on CH—CH bonds, under EC number 1.3.x.x, more preferably an oxidase acting on CH—CH bonds using oxygen as an electron acceptor, under EC number EC 1.3.3.x. Still more preferably, the oxidase is an acyl-CoA oxidase, suitably under EC number EC 1.3.3.6. More preferably the acyl-CoA oxidase is selected from any of the following enzymes: ACX4 from *Arabidopsis thaliana*, short chain acyl-CoA oxidase from *Arthrobacter nicotianae*, peroxisomal acyl-CoA oxidase from *Vigna radiata*, acyl-CoA oxidase from *Candida* sp. and acyl-CoA oxidase 4 from *Candida tropicalis*. Most preferably the acyl-CoA oxidase is ACX4 from *Arabidopsis thaliana*.

The oxidoreductase, may be an oxidoreductase under EC group number 1.X.X.X. Preferably, the oxidoreductase is an oxidoreductase acting on the CH—CH group of electron donors, suitably under EC group 1.3.X.X. More preferably, the oxidoreductase acting on the CH—CH group of donors is a FAD dependent oxidoreductase, still more preferably the oxidoreductase is a CoA dehydrogenase under EC group 1.3.8.X. More preferably still, the oxidoreductase is a short chain acyl-CoA dehydrogenase, suitably under EC group 1.3.8.1, an isovaleryl-CoA dehydrogenase, suitably under EC group 1.3.8.4, a 2-methyl-branched-chain acyl-CoA dehydrogenase, suitably under EC group 1.3.8.5 or an acyl-CoA dehydrogenase, suitably under EC group 1.3.8.-, such as an isobutyryl-CoA dehydrogenase. Most preferably the oxidoreductase is selected from any of the following enzymes: short/branched chain acyl-CoA dehydrogenase from *Pseudomonas putida*, isobutyryl-CoA dehydrogenase from *Homo sapiens* and isovaleryl-CoA dehydrogenase from *Arabidopsis thaliana*.

The CoA dehydrogenase enzymes generally require an associated electron transport system to couple oxidation of the substrate with reduction of ubiquinone, which is then regenerated. Such an electron transport system consists of an electron transfer flavoprotein (ETF), and an electron transfer flavoprotein ubiquinone oxidoreductase (ETFQO). The ETF must be compatible with both the acyl-CoA dehydrogenase enzyme and the ETFQO. Accordingly, in the embodiments where an acyl-CoA dehydrogenase is used, one of the following regeneration systems is preferably employed:

- a host microorganism expressing an endogenous CoA dehydrogenase, with activity on isobutyryl-CoA, and its associated electron transport system, such as is in the case of, for example, *Pseudomonas putida*;
- a host microorganism expressing a heterologous CoA dehydrogenase enzyme accompanied by the proteins of the electron transport system from the same organism as the heterologous CoA dehydrogenase. For example, the CoA dehydrogenase and electron transport system components from *Homo sapiens, Pseudomonas putida, Paracoccus denitrificans*, or from *Arabidopsis thaliana*, all expressed in *Escherichia coli* (or another host organism); or
- a host microorganism expressing a heterologous CoA dehydrogenase enzyme, accompanied by electron transport system components also from different microorganisms, whereby those components are compatible with each other and with the CoA dehydrogenase. For example, the CoA dehydrogenase from *Homo sapiens* is compatible with the electron transfer flavoprotein of *Sus scrota* which is in turn compatible with the electron transfer flavoprotein ubiquinone oxidoreductase from *Rhodobacter sphaeroides*. Alternatively, as the ETF-ubiquinone oxidoreductase of *A. thaliana* has good sequence homology with the ETF-ubiquinone oxidoreductase of *R. sphaeroides*, isovaleryl-CoA dehydrogenase and the ETF of *A. thaliana* could form a functional system with the ETF-ubiquinone oxidoreductase from *R. sphaeroides* for the oxidation of isobutyryl-CoA. Finally, the ETF and ETF-ubiquinone oxidoreductase from *Paracoccus denitrificans* are predicted to be compatible with an isobutyryl-CoA dehydrogenase from another source, such as that of *H. sapiens* or homologues from different organisms, due to the similarity of the *P. denitrificans* ETF with the human and porcine ETFs.

In embodiments, the microorganism may express one or more enzymes which can convert methacrylyl-CoA to a $C_3$-$C_{12}$ methacrylate ester, for example an alcohol acyltransferase.

Preferably, the alcohol acyltransferase acts in the presence of an alcohol, more preferably $C_3$-$C_{12}$ alcohol, most preferably, a $C_3$-$C_8$ alcohol, still more preferably in the presence of propanol or butanol, such as, n-propanol, isopropanol, n-butanol, isobutanol, sec-butanol, tert-butanol, pentanols, hexanols, heptanols or octanols. Most preferably, the alcohol acyltransferase acts in the presence of isopropanol or n-butanol.

By the term alcohol herein is meant a species having a hydroxyl group (—OH group) and which is capable of forming an ester group with the methacrylate.

Preferably the alcohol acyltransferase is derived from a plant origin, more preferably the plant belongs to any order selected from the group consisting of Zingiberales, Rosales, Ericales, Cucurbitales, Brassicales and Laurales; still more preferably the plant belongs to any family selected from the group consisting of Musaceae, Rosaceae, Ericaceae, Actinidiaceae, Cucurbitaceae, Caricaceae and Lauraceae; still more preferably the plant belongs to any genus selected from the group consisting of *Musa, Fragaria, Malus, Prunes, Pyrus, Vaccinium, Actinidia, Cucumis, Carica* and *Persea*; still more preferably the plant is any one selected from the group consisting of banana, strawberry, apple, *Prunes mume, Pyrus communis*, blueberry, kiwi, melon, papaya and avocado. Most preferably, the alcohol acyltransferase is derived from a fruit origin such as apple, melon or tomato origin, suitably apple origin.

In embodiments of the present invention the microorganism may express an oxidase and an alcohol acyltransferase for converting isobutyryl CoA to a $C_3$-$C_{12}$ methacrylate ester. Suitable oxidases and alcohol acyltransferases are outlined above. It is particularly preferred if the oxidase is ACX4 from *Arabidopsis thaliana*.

In embodiments, the microorganism may express one or more enzymes which can convert 2-ketoisovaleric acid to isobutyryl-CoA. In embodiments, the one or more enzymes may be an enzyme complex such as a branched chain keto acid dehydrogenase enzyme complex, consisting of the alpha subunit component, the lipoamide acyltransferase component and the lipoamide dehydrogenase component. Most preferably, the dehydrogenase is selected from any of the following enzymes: branched chain keto acid dehydrogenase (BCKD) from *P. putida*, BCKD from *Bacillus subtilis*, BCKD from *P. aeuruginosa*, BCKD from *A. thaliana*, BCKD from *Streptomyces coelicolor* and BCKD from *Thermus thermophilus*.

Alternatively, the conversion of 2-ketoisovaleric acid to isobutyryl-CoA may be catalysed by an oxidoreductase enzyme, suitably under EC group 1.X.X.X, preferably an oxidoreductase acting on the aldehyde or oxo group of donors, suitably under EC group 1.2.X.X, more preferably an oxidoreductase enzyme acting on the aldehyde or oxo group of donors, using an iron-sulfur protein as the electron acceptor, suitably under EC group 1.2.7.X, most preferably a 2-ketoisovalerate ferredoxin reductase (known also as ketovaline ferredoxin oxidoreductases), suitably under EC group number 1.2.7.7, which is a tetramer consisting alpha, beta, gamma and delta subunits. Examples of such enzymes are 2-ketoisovalerate ferredoxin reductase from *Pyrococcus furiosis;* 2-ketoisovalerate ferredoxin reductase from *Pyrococcus* sp.; 2-ketoisovalerate ferredoxin reductase from *Thermococcus* sp2-ketoisovalerate ferredoxin reductase from *Thermococcus litoralis;* 2-ketoisovalerate ferredoxin reductase from *Thermococcus profundus* and 2-ketoisovalerate ferredoxin reductase from *Methanobacterium thermoautotrophicum*.

Alternatively, the microorganism may express one or more enzymes which can convert isobutyric acid to isobutyryl-CoA, for example a ligase. The ligase is suitably under EC group number 6.X.X.X, preferably a carbon-sulfur bond forming ligase under EC group 6.2.X.X, more preferably an acid-thiol forming ligase under EC group 6.2.1.X, more preferably a GDP-forming, an ADP forming or an AMP forming ligase, such as an AMP forming acetate-CoA ligase, suitably under EC group 6.2.1.1, a butyrate-CoA ligase, suitably under EC group 6.2.1.2, a carboxylic acid-CoA ligase, suitably under EC group 6.2.1.10, an ADP forming acetate-CoA ligase, suitably under EC group 6.2.1.13, a propionate-CoA ligase, suitably under EC group 6.2.1.17 or an acid-thiol ligase in EC group 6.2.1.-. Most preferably the ligase is selected from any of the following enzymes: AcsA from *Pseudomonas chlororaphis*, butyryl-CoA synthetase from *Paecilomyces varioti*, butyryl-CoA synthetase from bovine heart mitochondria.

Alternatively, the microorganism may express one or more enzymes which can convert isobutyrate to isobutyryl-CoA. For example, isobutyrate may be converted to isobutyryl-phosphate by a kinase enzyme and isobutyryl-phosphate may be converted to isobutyryl-CoA by a transferase enzyme.

Preferably, the isobutyrate is converted to isobutyryl-phosphate by a kinase enzyme, suitably under EC group number EC 2.X.X.X, preferably under EC 2.7.X.X, more preferably under EC group number EC 2.7.2.X, most preferably an acetate kinase, suitably under EC group 2.7.2.1, a formate kinase under EC 2.7.2.6, a butyrate kinase under EC 2.7.2.7, a branched chain fatty acid kinase under EC 2.7.2.14 or a propionate kinase under EC 2.7.2.15.Most preferably the kinase is selected from any of the following enzymes: branched chain fatty acid kinase from Spirochete MA-2, butyrate kinase from *C. butyricum*.

Preferably, the isobutyryl-phosphate is converted to isobutyryl-CoA by the action of a transferase enzyme, under EC group number 2.X.X.X, more preferably by the action of an acyltransferase under EC group number 2.3.X.X, still more preferably by the action of acyltransferase transferring groups other than amino-acyl groups under EC group number 2.3.1.X. Still more preferably a phosphate acetyltransferase or a phosphate butyryltransferase, under EC group numbers 2.3.1.8 and 2.3.1.19, respectively. More preferably the transferase is phosphate butyryltransferase from *Clostridium acetobutylicum* ATCC824 or phosphate acetyltransferase from *Bacillus subtilis, Corynebacterium glutamicum* ATCC13032, *Thermotoga maritima* and *Clostridium kluyveri*. Other sources of these enzymes include other anaerobic bacteria, especially *Clostridium* species such as *Clostridium pasteurianum* or *Clostridium beijerinckii*.

The microorganism may express one or more enzymes which can convert isobutyric acid to isobutyryl-CoA, for example a synthetase enzyme, preferably an isobutyryl-CoA synthetase, most preferably isobutyryl-CoA synthetase (AcsA) from *P. chloraphis* B23.

Suitable modifications and constructs used are also disclosed in WO2016/185211 incorporated herein by reference.

Fermentation Medium and Fermentation

In another aspect, the invention relates to a fermentation medium comprising an isolated genetically modified microorganism with increased tolerance to a methacrylate compared to a wild type microorganism. The genetically modified microorganism with increased tolerance comprises a modification of a protein component or regulator of the oxidative stress response or multidrug resistance system as described above.

In one embodiment, the microorganism(s) are provided in a fermentation medium under conditions in which said microorganism will produce a $C_3$-$C_{12}$ methacrylate ester.

Various aspects and embodiments of the invention comprise culturing a wild type or genetically modified microorganism in said fermentation medium. Culturing or cultivation suitably requires a carbon based feedstock upon which the microorganism may derive energy and grow. Preferably, therefore, the microorganism/s are cultured on a carbon based feedstock.

The fermentation medium may be a surrounding medium which surrounds the microorganism/s. Preferably a carbon based feedstock is present in the medium, optionally dissolved or suspended in the medium, bubbled through the medium and/or mixed with the medium. Preferably, therefore, the medium comprises the microorganism/s and the carbon based feedstock together with any buffers and salts.

The fermentation medium may be any commercially available medium suitable for the needs of the microorganism. The fermentation medium suitably contains a carbon based feedstock and a nitrogen source, as well as additional compounds required for growth of the microorganism/s and/or the formation of $C_3$-$C_{12}$ methacrylate ester.

Examples of suitable carbon based feedstocks known in the art include glucose, maltose, maltodextrins, sucrose, hydrolysed starch, starch, lignin, aromatics, syngas or its components, methane, ethane, propane, butane, molasses and oils, carbon dioxide. Preferably the carbon based feedstock is derived from biomass. Mixtures may also be used, as well as wastes, such as municipal waste, food waste and lignocellulosic wastes from food processing, forestry or agriculture.

Examples of suitable nitrogen sources known in the art include soy bean meal, corn steep liquor, yeast extract, ammonia, ammonium salts, nitrate salts, urea, nitrogen gas or other nitrogenous sources.

Examples of additional compounds which may be required for growth of the microorganism/s (and therefore may be present in the fermentation medium) include antibiotics, antifungals, anti-oxidants, buffers, phosphate, sulphate, magnesium salts, trace elements and/or vitamins.

Additional compounds required for growth of the microorganism/s and/or for the production of $C_3$-$C_{12}$ methacrylate ester, like phosphate, sulphate or trace elements, may be added in amounts that may vary between different classes of microorganisms, i.e. between fungi, yeasts and bacteria. In addition, the amount of additional compound to be added may be determined by what pathways are used to form the $C_3$-$C_{12}$ methacrylate ester.

The amount of carbon based feedstock and nitrogen source to be added to the medium may vary depending on the needs of the microorganism/s and/or the length of the culturing of the microorganisms. The ratio of the carbon based feedstock to the nitrogen source in the culture medium may vary considerably.

Typically, the amount of each fermentation medium component necessary for growth of a microorganism is determined by measuring the growth yield on the nutrient and further assessed in relation to the amount of carbon based feedstock used in the culturing process, since the amount of biomass formed will be primarily determined by the amount of carbon based feedstock used, and the nutrient limitations imposed during any feeding regime.

In embodiments where the carbon based feedstock is derived from biomass, the biomass preferably comprises a high amount of carbohydrates. Particularly preferable are carbohydrates which are sources of C5 or C6 sugars, carbon based gases, or aromatics, preferably C5 or C6 sugars, more preferably glucose, such as, but not limited to starch, lignin, cellulose, glycogen, arabinoxylan, chitin or pectin.

Alternatively, the biomass may comprise a high amount of fats, particularly preferable are fats or oils which are sources of glycerol and fatty acids, specifically triglycerides. Suitable triglycerides include any oil or fat which is readily available from a plant or animal source. Examples of such oils and fats include palm oil, linseed oil, rapeseed oil, lard, butter, herring oil, coconut oil, vegetable oil, sunflower oil, castor oil, soybean oil, olive oil, cocoa butter, ghee, blubber etc.

The biomass may be composed of one or more different biomass sources. Examples of suitable biomass sources include virgin wood, energy crops, agricultural residues, food waste, municipal waste and industrial waste or co-products.

Virgin wood biomass sources may includes but are not limited to wood chips, bark, brash, logs, sawdust, wood pellets or briquettes.

Energy crop biomass sources may include but are not limited to short rotation coppices or forestry, non-woody grasses such as miscanthus, hemp switchgrass, reeds or rye, agricultural crops such as sugar, starch or oil crops, or aquatic plants such as micro or macroalgae and weeds.

Agricultural residues may include but are not limited to husks, straw, corn stover, flour, grains, poultry litter, manure, slurry, syngas or silage.

Food wastes may include but are not limited to peel/skin, shells, husks, cores, pips/stones, inedible parts of animals or fish, pulp from juice and oil extraction, spent grains or hops from brewing, domestic kitchen waste, lard or oils or fats.

Industrial wastes may include but are not limited to untreated wood including pellets, treated wood, shale gases, wood composites including MDF/OSD, wood laminates, paper pulp/shreddings/waste, textiles including fibre/yarn/effluent, or sewage sludge.

The microorganism may be cultured as a batch, a repeated batch, a fed-batch, a repeated fed-batch or a continuous cultivation (chemostat, turbidostat or auxostat) process.

The culturing process is preferably performed on an industrial scale. An industrial scale process is understood to encompass a culturing process in one or more fermenters of a volume scale which is $\geq 0.01$ m$^3$, preferably $\geq 0.1$ m$^3$, preferably $\geq 0.5$ m$^3$, preferably $\geq 5$ m$^3$, preferably $\geq 10$ m$^3$, more preferably $\geq 25$ m$^3$, more preferably $\geq 50$ m$^3$, more preferably $\geq 100$ m$^3$, most preferably $\geq 200$ m$^3$.

In embodiments, the culturing is performed in a bioreactor. A bioreactor is generally understood to mean a container in which microorganisms are industrially cultured. Bioreactors can be of any size, number and form, and can include inlets for providing nutrients, additional compounds for growth, fresh medium, carbon based feedstocks, additives of gases, such as, but not limited to, air, nitrogen, oxygen or carbon dioxide. Bioreactors may also comprise outlets for removing volumes of the culture medium to collect the $C_3$-$C_{12}$ methacrylate ester from the fermentation medium. The bioreactor may also have an outlet for sampling of the culture. The bioreactor may have a system for measuring and controlling the pH. This pH control system is used to control medium addition in a pH-auxostat culture. In some embodiments, flask cultures may be used.

The bioreactor can generally be configured to mix the fermentation medium, for example, by stirring, rocking, shaking, inverting, bubbling of gas through the culture etc. Alternatively, some continuous cultures do not require mixing, for example microreactor systems using a plug flow system. Bioreactors are common and well known in the art and examples may be found in standard texts, such as 'Biotechnology: A Textbook of Industrial Microbiology, Section Edition (1989) Authors: Wulf Cruegar and Annelise Crueger, translated by Thomas D. Brock Sinauer Associates, Inc., Sunderland, Mass.

The invention also relates to a culture medium comprising a genetically modified organism as described herein. Furthermore, the invention relates to a vessel comprising a fermentation or culture medium comprising a genetically modified organism as described herein. Furthermore, the invention relates to a kit comprising a fermentation or culture medium comprising a genetically modified organism as described herein.

Mutant Organisms and Uses Thereof

In another aspect, the invention also relates to an isolated methacrylate tolerant, in particular a $C_3$-$C_{12}$ methacrylate ester tolerant, genetically modified microorganism for use in the production of a methacrylate, for example a $C_3$-$C_{12}$ methacrylate ester. Furthermore, the invention relates to the use of an isolated methacrylate tolerant, in particular a $C_3$-$C_{12}$ methacrylate ester tolerant, genetically modified microorganism in the production of a methacrylate, for example a $C_3$-$C_{12}$ methacrylate ester. The genetically modified microorganism may be as described in detail above.

In a further aspect, the invention relates to an isolated methacrylate tolerant, in particular a $C_3$-$C_{12}$ methacrylate ester tolerant, genetically modified microorganism comprising a mutation in marR (SEQ ID NO. 7) wherein said mutant marR nucleic acid encodes a protein with substitution of V84 with another amino acid, for example G, with reference to SEQ ID NO. 8. In a further aspect, the invention relates to an isolated methacrylate tolerant, in particular a $C_3$-$C_{12}$ methacrylate ester tolerant, genetically modified microorganism comprising a mutation in rob (SEQ ID NO. 5) wherein said mutant Rob nucleic acid encodes a protein with substitution of A70 or a substitution of R156 with another amino acid in Rob with reference to SEQ ID NO. 6. In a further aspect, the invention relates to an isolated methacrylate tolerant, in particular a $C_3$-$C_{12}$ methacrylate ester tolerant, genetically modified microorganism comprising a mutation in acrR (SEQ ID NO. 3) wherein said mutant acrR nucleic acid encodes a protein with a frameshift mutation at T32 with reference SEQ ID NO:4. In a further aspect, the invention relates to an isolated methacrylate tolerant, in particular a $C_3$-$C_{12}$ methacrylate ester tolerant, genetically modified microorganism comprising a mutation in soxR (SEQ ID NO. 1) wherein said mutant soxR nucleic acid encodes a protein with a substitution of R20 with another amino acid, deletion of residue 146 or a truncation at residue 139 with reference SEQ ID NO. 2.

In a further aspect, the invention relates to an isolated methacrylate tolerant, in particular a $C_3$-$C_{12}$ methacrylate ester tolerant, genetically modified microorganism comprising a mutation in two or more nucleic acids selected from the following: a soxR, acrR, marR and/or a rob nucleic acid or a homolog thereof wherein said nucleic acid encodes a mutant protein.

In a further aspect, the invention relates to an isolated methacrylate tolerant, in particular a $C^3$-$C_{12}$ methacrylate ester tolerant, genetically modified microorganism comprising a mutation in acrR and a mutation in a nucleic acid selected from the following: a soxR, marR or a rob nucleic acid or a homolog thereof wherein said nucleic acid encodes a mutant protein.

According to the various aspects of the invention, the microorganism is as described above and in one embodiment, the microorganism is E. coli.

In one embodiment, the mutant soxR nucleic acid sequence encodes a mutant SoxR protein with a mutation in the DNA binding domain (residues 1-80) or in the FE-S cluster domain (residues 119-154). In one embodiment, the mutation in SoxR is selected from one of the following: a substitution of R20 with another amino acid, a substitution of R20 with another amino acid, deletion of residue 146, or a truncation at residue 139 with reference SEQ ID NO. 2. In one embodiment, substitution of R20 is with H. In one embodiment, substitution of R20 is with L. Also within the scope of the invention are modifications at equivalent positions in homologues of SoxR in microorganisms other than E. coli.

In one embodiment, the acrR nucleic acid sequence encodes a mutant AcrR protein with a mutation in the DNA binding domain (residues 7-51) or in the ligand binding domain (residues 55-204). In one embodiment, the mutation in AcrR is selected from one of the following: a substitution of V29 with another amino acid, a frameshift mutation at T32, a frameshift mutation at Y49, a frameshift mutation occurs at A191, a deletion of residue 146, or a truncation at residue 139 with reference SEQ ID NO:3. In one embodiment, substitution of V29 is with G. Also within the scope of the invention are modifications at equivalent positions in homologues of AcrR in microorganisms other than E. coli.

In one embodiment, the mutant rob nucleic acid sequence encodes a mutant Rob protein with a mutation in the N-terminal DNA binding domain (residues 1-120) and C-terminal domain (residues 121-189). In one embodiment, the mutation in Rob is selected from one of the following: a substitution of A70 or a substitution of R156 with another amino acid in Rob with reference to SEQ ID NO. 6. In one embodiment, substitution of A70 is with V or T. In one embodiment, substitution of R156 is with H. Also within the scope of the invention are modifications at equivalent positions in homologues of Rob in microorganisms other than E. coli.

In one embodiment, the mutant marR nucleic acid sequence encodes a mutant MarR protein with a mutation in the DNA binding domain (residue 55-100). In one embodiment, the mutation in MarR is a substitution of V84 with another amino acid with reference to SEQ ID NO. 8. In one embodiment, substitution of V84 is with G. Also within the scope of the invention are modifications at an equivalent position in homologues of MarR in microorganisms other than E. coli.

In one embodiment, two or more mutations as shown in table 1a are present. In one embodiment, the microorganism is selected from a microorganism having genetic mutations as listed below:
  rob(R156H)rpoC(L361R)ilvN(C41Y)ygbK(A294E) lpxM(168_185del);
  rob(R156H)ilvN(C41Y) phoP(L11F)acrB(V448 L);
  soxR (Leu139X) 580116(G>T);
  soxR(A146del);
  rob(A70V);
  rob(R156H)rpoB(T1037P) torY(A87T) acrR(49Yfs);
  rob(A70T)yohJ(L109R) dnaK(V377G) 927777(C>T) acrR(A191fs);
  marR(V84G)rpoC(R1075C)ompR(R15S) acrB(T379I);
  marR(V84G)rpoC(R1075C)ompR(R15S);
  marR(V84G)rpoC(R1075C) rpoC(A787V)ompR(R15S) acrB(V901I);
  rob(R156H)rpoB(T1037P) groL(P279 L) acrR(49Yfs) 1197659(C>A) or
  soxR(R20 L)rpoC(r1075C) 2133236(T>A)3915915(T>G).

In one embodiment, a mutation in soxR is combined with a mutation in acrR. As demonstrated in the examples, the inventors have surprisingly found that combining mutations in the two genes leads to an additive tolerance effect. In one embodiment, a mutation in soxR is combined with a mutation in marR. In one embodiment, a mutation in soxR is combined with a mutation in rob.

In one embodiment, the microorganism also comprises one or more further mutation, for example in a gene that encodes a protein component or regulator of the oxidative stress response. In one embodiment, the mutation is in a rpo nucleic acid sequence, for example rpoB (SEQ ID NO 25) or rpoC (SEQ ID NO 27), ompR (SEQ ID NO 29), acrB (SEQ ID NO 9), yohJ (SEQ ID NO 11), torY (SEQ ID NO 13), ipxM (SEQ ID NO 15), dnaK (SEQ ID NO 17), grol SEQ ID NO 19), ilvN (SEQ ID NO 21), phop SEQ ID NO 31), ygbK(SEQ ID NO 23). In another embodiment, no further modifications of the protein component or regulator of the oxidative stress response or multidrug resistance system are present.

In one embodiment, a mutation in acrR is combined with one or more mutations in one of marR, rob or soxR. This is based on the surprising finding that a mutation in acrR was found in combination with marR, rob or soxR (see example 2).

In one embodiment, a mutation in acrR is combined with one or more mutations in marR. In one embodiment, a mutation in acrR is combined with one or more mutations in rob. In one embodiment, the one or more further mutation is selected from a mutation listed in table 1b.

Methods for Making Mutant Organisms

The invention also relates to methods for the isolation of a methacrylate tolerant microorganism comprising:
a) providing a microorganism in a fermentation medium
b) contacting the microorganism with a methacrylate; and
c) isolating the viable microorganism of step (b)
wherein the viable microorganism is tolerant to at least 20% v/v a methacrylate when grown in liquid medium at about 37° C.

The microorganism is selected from a microorganism as described above, such as E. coli. In one embodiment, the method employs an adaptive evolution approach which comprises culturing the organism in a medium that comprises sequentially increasing concentrations of a methacrylate, for example BMA. For example, in a first step, the microorganism is contacted with a methacrylate at a concentration of 0.1%. In subsequent steps, the concentration is increased stepwise from 0.1%, to, for example, 0.5%, 1%, 5%, 10% and 20% and the microorganism is exposed to this concentration of a period of time. In another embodiment, the concentration is increased stepwise to 10% and 20%. Contacting the microorganism with a methacrylate at each concentration may be for about (0.1 h to 144 hours) for 1 to 45 times. In another embodiment, the culturing temperature may be altered during the method. The culturing temperature may be maintained at 4° C. to 50° C. In another embodiment, the method comprises incubating one culture with BMA until growth occurs then isolating mutants.

For example, the adaptive evolution can be carried out in the following way: Adaptive evolution of E. coli in a chemostat can be established at a starting dilution rate of about 0.33 h$^{-1}$. The BMA concentration is then gradually increased in a step-wise manner from 0 to 20% v/v at a constant dilution rate. After attaining a stable cell concentration at about 20% v/v BMA, the dilution rate of the culture can be adjusted between about 0.33 h$^{-1}$ and about 0.55 h$^{-1}$ with the BMA concentration kept constant at about 20% v/v. A further adaptive evolution experiment was achieved with a step-wise increases in temperature from 37° C. to 44° C., while maintaining the BMA concentration at about 20% v/v and initial dilution rate of about 0.41 h$^{-1}$. Adaptive evolution with the use of a pH-auxostat can be achieved using a pH feedback control system, where the inflow of nutrients, base, and other additives are initiated only when the pH goes below the set value. The acidification of the media in the bioreactor indicates growth of cells in the culture with its rate controlling the addition of nutrients and consequently the dilution rate. The dilution rate adjusts to match the growth rate of the culture under the imposed condition and allows auto-selection, where the rapidly growing strains persist in the bioreactor and slower growing strains being washed out. The evolution experiment of E. coli in the pH-auxostat can be started with no BMA initially added to the bioreactor. The BMA concentration can gradually be increased from 0 to 0.1%, 0.5%, 1.0%, 5.0%, 10%, and 20% v/v.

The microorganism is grown in a suitable fermentation medium as described above at about 37° C., for example at about 200 RPM.

The methacrylate is as described elsewhere herein.

The invention also relates to a microorganism isolated by a method described above.

All documents mentioned in this specification, including all reference to SEQ ID NOs in gene and protein databases are incorporated herein by reference in their entirety. Sequence versions are version 1 unless otherwise specified.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

The invention is further described in the following non-limiting examples.

EXAMPLES

Example 1: Isolation and Characterisation of BMA Tolerant Mutant Strains

E. coli K12 MG1655 was used in these experiments. This is a common laboratory strain and the complete genome sequence of this strain is available (NCBI Reference Sequence: NC_000913.3). This strain can, for example, be obtained from the Coli Genetic Stock Center (CGSC) (strain 7636) or ATCC.

We isolated E. coli MG1655 variants that are tolerant to BMA. E. coli MG1655 was grown in MSX medium containing 20% (v/v) BMA for 72 hours, in 30 mL vials at 37° C., 250 rpm. Growth was observed after 72 h. A sample from this culture was streaked out onto LB agar plates and incubated overnight at 37° C. Colonies were then isolated and whole genome deep sequencing analysis using Illumina NGS technology according to the manufacturers' directions was performed to characterise the mutants. Fastq output files were analyzed for variants compared to the MG1655 reference genome (accession number NC_00913.1). Sequencing analysis identified the following mutations:
E. coli MG1655 soxR(R20H)
E. coli MG1655 soxR(R20H)acrR(V29G)
E. coli MG1655 soxR(R20H)acrR(T32fs)

In a subsequent screening experiment, wild type E. coli MG1655 and mutants isolated as described above, (E. coli MG1655 soxR(R20H), E. coli MG1655 soxR(R20H)acrR(V29G), E. coli MG1655 soxR(R20H)acrR(T32fs)) were grown in defined medium (MSX) in the absence or presence of 20% (v/v) BMA added immediately after inoculation (FIG. 1). Cultures were grown in 250 mL shake flasks at 37° C. and 250 rpm. The WT strain was unable to grow in the presence of 20% (v/v) BMA, but all mutants were able to grow in the presence of 20% (v/v) BMA demonstrating that the mutations confer resistance to BMA. We also observed that double mutants E. coli MG1655 soxR(R20H)acrR (V29G) and E. coli MG1655 soxR(R20H)acrR(T32fs) were able to grow better than the single mutant with the soxR mutation, showing that the combination of mutations in soxR and acrR provides an additive effect and enhances the tolerant phenotype.

E. coli MG1655, E. coli MG1655 soxR(R20H), E. coli MG1655 soxR(R20H)acrR(V29G) and E. coli MG1655 soxR(R20H)acrR(T32fs) were then grown in MSX medium with 20% (v/v) BMA added during mid-exponential phase (FIG. 2). Cultures were grown in 250 mL shake flasks at 37° C. and 250 rpm. These results show once again that the mutated genes acrR(V29G) and acrR(T32fs) in combination with soxR(R20H) improve the adaptation of the cells and confer enhanced tolerance to BMA compared to the soxR (R20H) mutation alone.

We then created strains in which soxR and acrR respectively were knocked out using standard protocols. The knock-out strains E. coli BW25113 ΔsoxR and E. coli BW25113 ΔacrR were grown in the absence or presence of 20% (v/v) BMA added immediately after inoculation (FIG. 3). Cultures were grown in MSX medium in 30 mL vials at 37° C. and 250 rpm shaking. Although the knock-out strains were able to grow in the medium with no BMA, all of them were unable to grow in the presence of BMA. This shows that the loss of function of acrR and soxR does not confer BMA tolerance. Hence, soxR(R20H) encodes a functional SoxR, capable of regulating the transcription of other genes. Likewise, the mutated genes acrR(V29G) and acrR(T32fs) may encode functional proteins able to confer BMA tolerance.

Strains with single mutations were prepared to understand if acrR(V29G) and acrR(T32fs) could confer BMA tolerance by themselves and, therefore, encode functional proteins. E. coli MG1655 acrR(V29G) and E. coli MG1655 acrR(T32fs) were then grown with or without 20% (v/v) BMA, added immediately after inoculation (FIG. 4). Cultures were grown in MSX medium in 30 mL vials at 37° C. and 250 rpm shaking E. coli MG1655 acrR(V29G) and E. coli MG1655 acrR(T32fs) were all able to grow in the presence of BMA. This suggests that these mutations encode a functional AcrR, able to act as transcription factor, conferring resistance to BMA.

In summary, the results show that mutations in soxR or acrR confer resistance to BMA compared to wild type E. coli and that double mutants that comprise mutations in both soxR or acrR show enhanced resistance.

Example 2: Isolation and Characterisation of BMA Tolerant Mutant Strains by Adaptive Evolution We identified BMA tolerant strains using an adaptive evolution approach. In summary, adaptive evolution involves the extended propagation of a microbial strain under the influence of the desired selective pressure. Mutants with enhanced growth rates due to increased tolerance will occasionally arise and expand within the population over time. Enhanced strains are therefore obtained by repeated isolation, characterization, and sequencing of these mutant isolates.

The experiments used E. coli strain BW25113. This is a common laboratory strain and the complete genome sequence of this strain is available (NCBI Reference Sequence: NZ_CP009273.1, see Grenier et al: Complete Genome Sequence of Escherichia coli BW25113, Genome Announc. 2014 September-October; 2(5): e01038-14). This strain can, for example, be obtained from the Coli Genetic Stock Center (CGSC) (strain 7636) or ATCC.

Figure 5A:
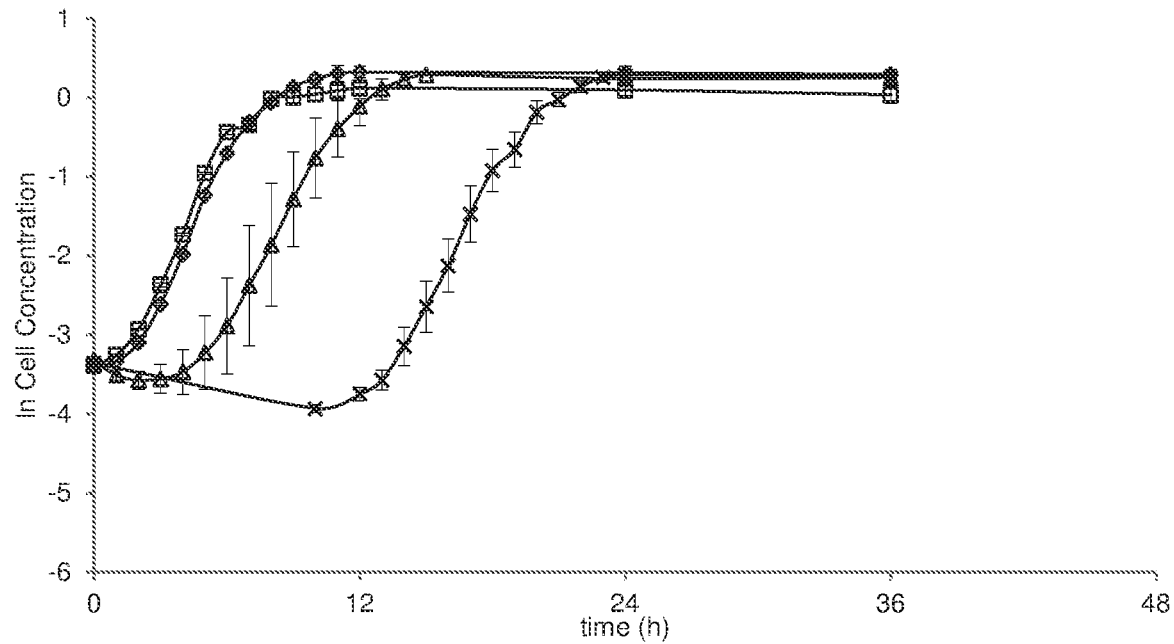
Figure 5B:
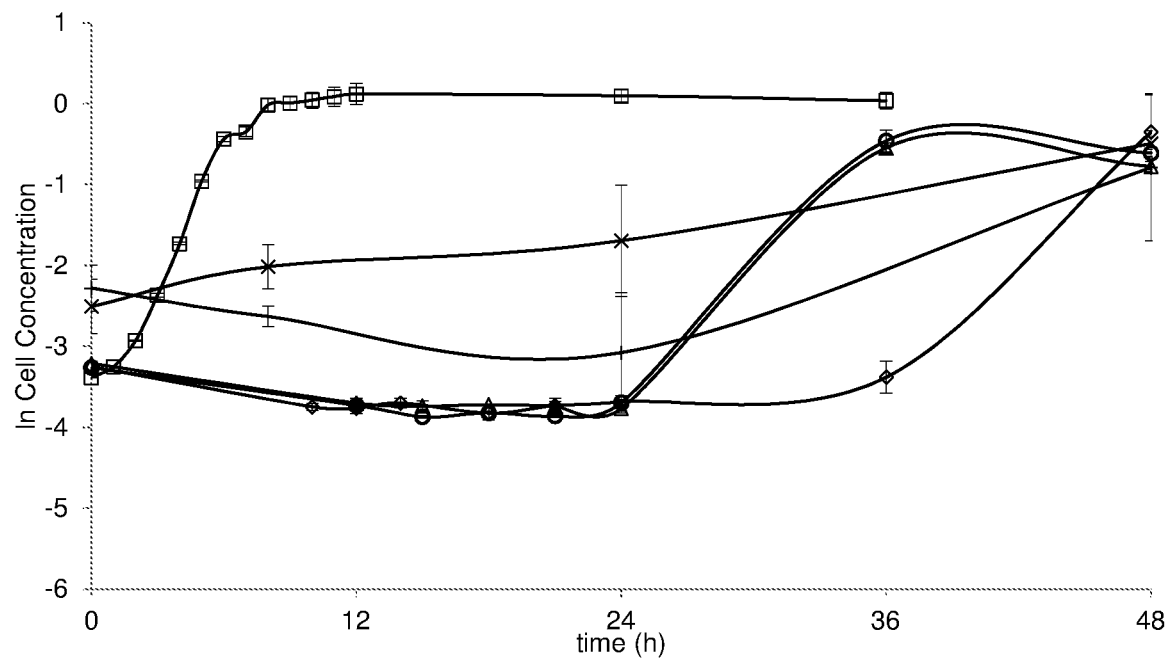

The effect of BMA on its growth was firstly investigated by growing the microorganism in the presence of BMA at a concentration range of 0.01% to 20.0% v/v (FIGS. 5a and 5b). Growth of E. coli at a BMA concentration of 0.01% v/v (FIG. 5.1) was very similar to its growth in the absence of BMA. However, a longer lag phase and lower growth rate was observed as the BMA concentration was increased further to 0.05 and 0.1% v/v (FIG. 5a and Table 2.1). Therefore, BMA inhibits the growth of E. coli at concentrations above 0.05% v/v.

As the BMA concentration was increased further to 20% v/v (FIG. 5b), cell growth was only observed after 24-36 hours of incubation, and growth was inconsistent.

TABLE 2.1

Growth kinetic parameters of E. coli at various BMA concentrations

| BMA content (% v/v) | Max cell concentration (g L$^{-1}$) | Growth rate (h$^{-1}$) | Lag phase (h) |
| --- | --- | --- | --- |
| 0 | 1.436 ± 0.213 | 0.728 ± 0.011 | 1 |
| 0.01 | 1.365 ± 0.120 | 0.617 ± 0.009 | 2 |
| 0.05 | 1.269 ± 0.074 | 0.517 ± 0.014 | 4 |
| 0.1 | 1.335 ± 0.074 | 0.519 ± 0.010 | 12 |

Figure 5C:
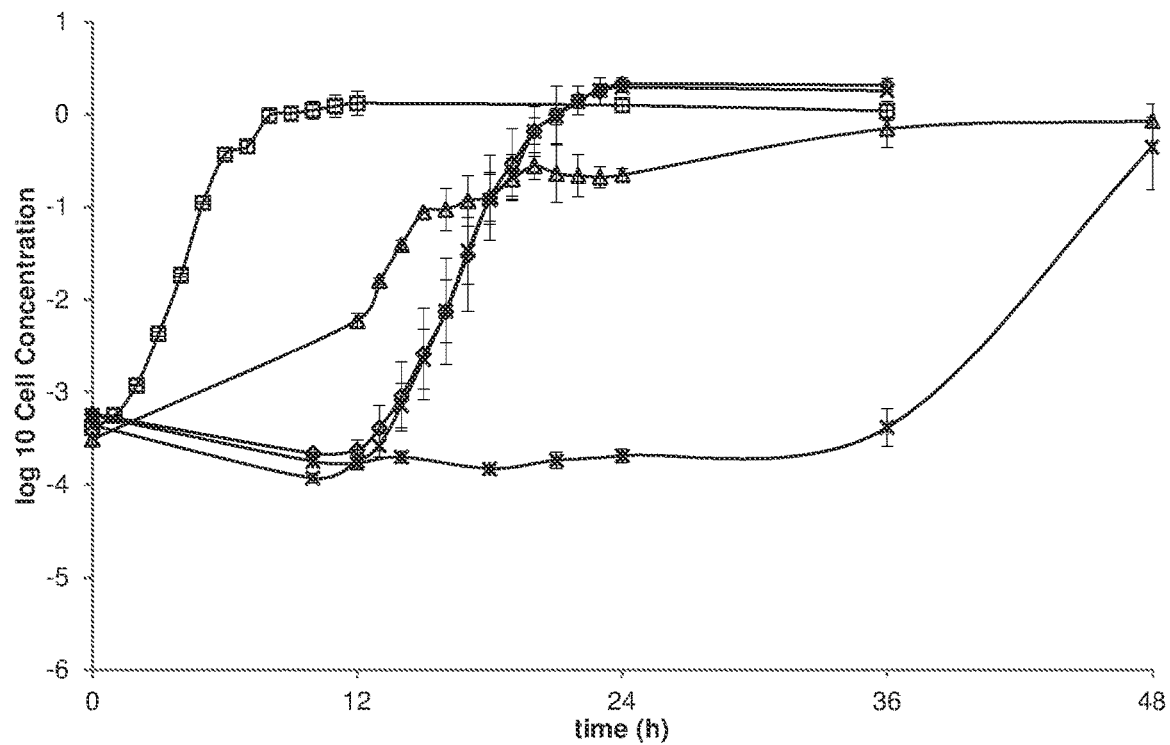

Cultures grown with 0.1 and 0.5% v/v BMA were subcultured (FIG. 5.3) to understand the BMA tolerance limit of E. coli. An aliquot was taken from a culture grown with 0.1% v/v BMA, transferred to fresh medium and grown under the same conditions. The growth pattern of the subculture population was very much the same as for the previous culture (FIG. 5c), which suggests that the tolerance observed at 0.1% v/v BMA is likely due to the inherent tolerance of E. coli. On the other hand, the subculture taken from a culture grown at 0.5% v/v BMA exhibited significant growth after only 12 hours of inoculation, which is much earlier compared to the progenitor culture grown under the same conditions (FIG. 5c). The difference in the growth pattern of the original culture and the subculture suggests that the growth of E. coli in the subculture was not due to inherent tolerance but rather acquired after exposure to 0.5% v/v BMA.

The result from the subculture experiments suggested that the inherent tolerance of E. coli towards BMA is at least 0.1% v/v, but no more than 0.5% v/v.

Figure 5D:
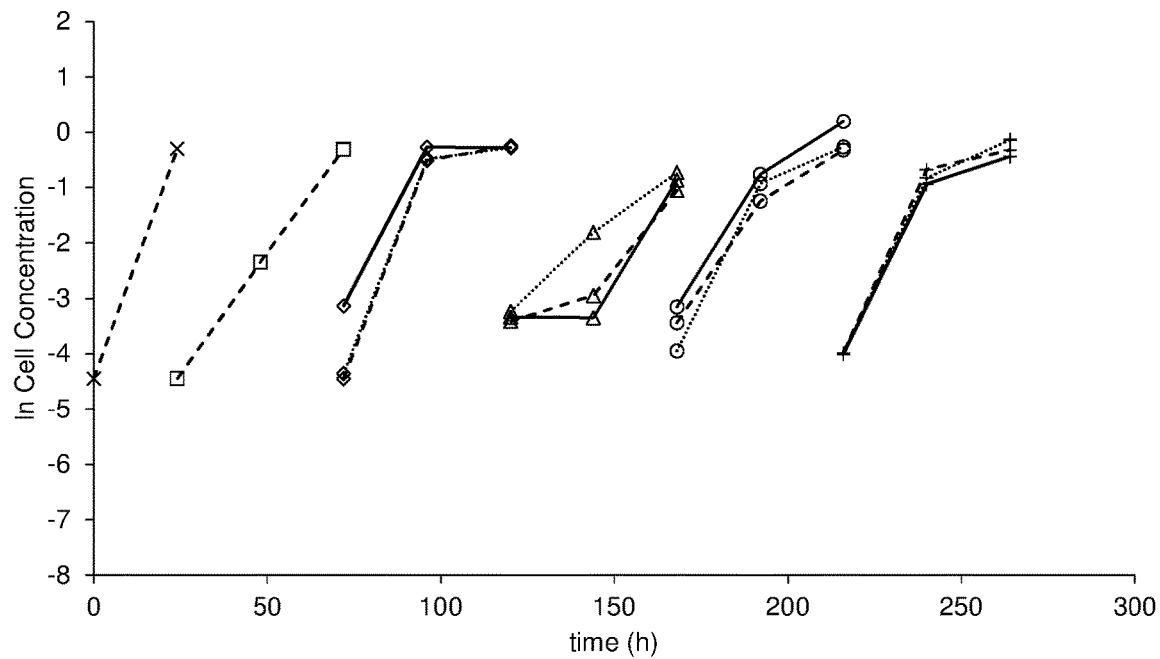

Various adaptive evolution experiments were used to generate BMA tolerant E. coli. In the first experiment (ADE-1; FIG. 5d), three parallel cultures were grown in a 50 mL FALCON® tube containing 10 mL M9 minimal medium with increasing BMA concentration from 0.1% to 0.5%, 1.0%, 5.0%, 10.0%, and 20% v/v, respectively for each sequential transfer. An aliquot of 0.15 mL was used from the previous culture and transferred to the fresh media with higher BMA concentration. The best growing culture was used as the starting culture for the next sequential transfer.

Figure 5E:
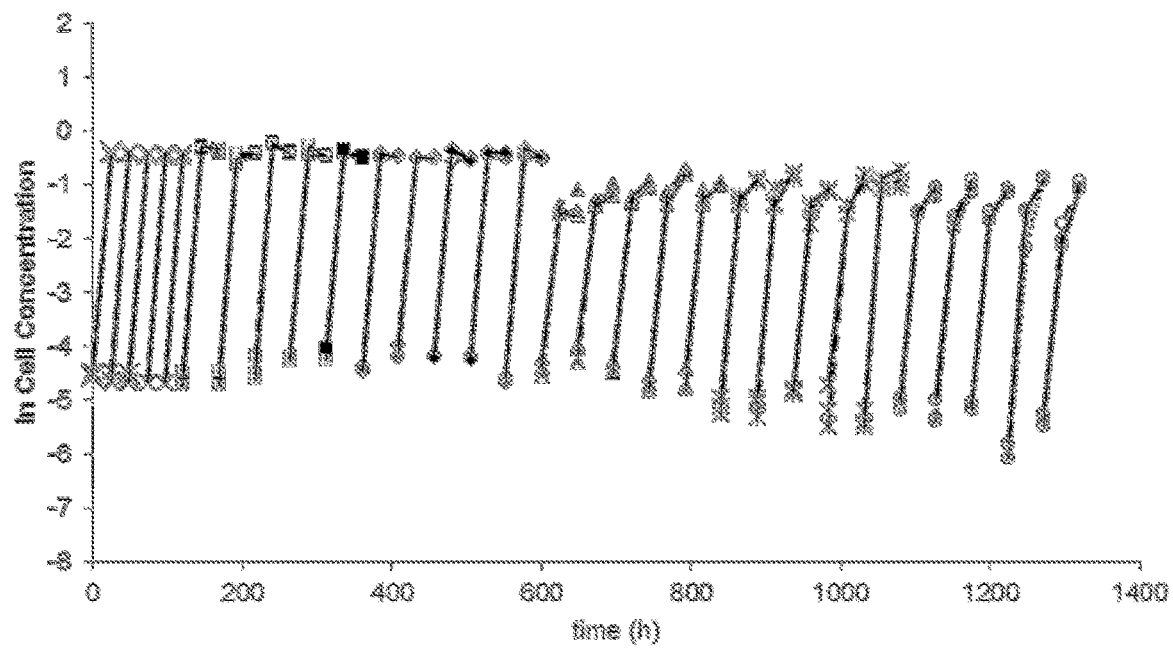

In the second adaptive evolution experiment (ADE-2; FIG. 5e), the cells allowed to undergo five (5) serial transfers at the same BMA concentration prior to increasing the BMA concentration. In this experiment, each of the three cultures were used as a starting culture for the sequential transfer in separate tubes.

Figure 5F:
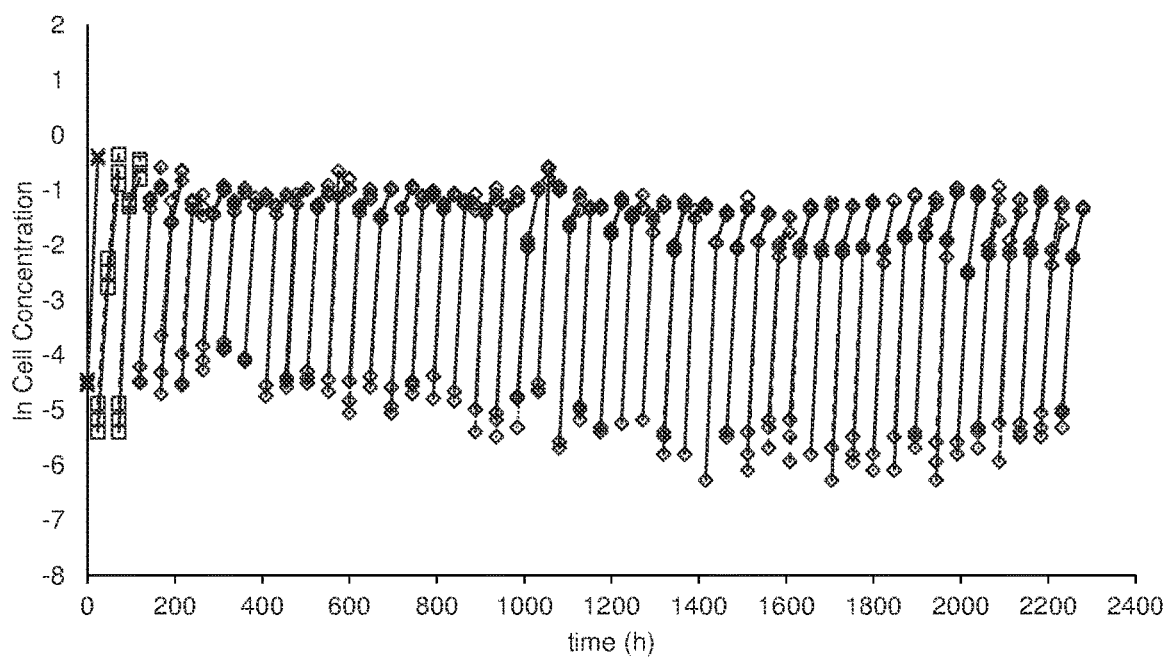

A third adaptive evolution experiment (ADE-3; FIG. 5f) was done by growing E. coli once with 0.1% v/v BMA, then twice with 10% v/v BMA, and finally 45 times with 20% v/v BMA.

Figure 5G:
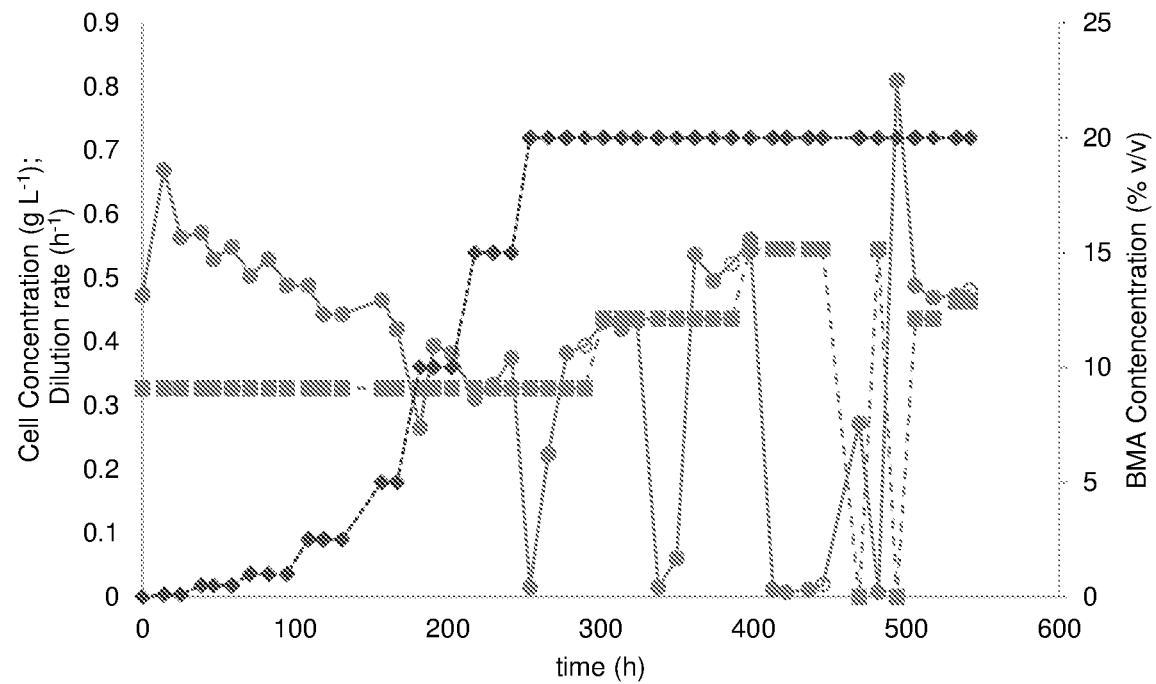
Figure 5H:
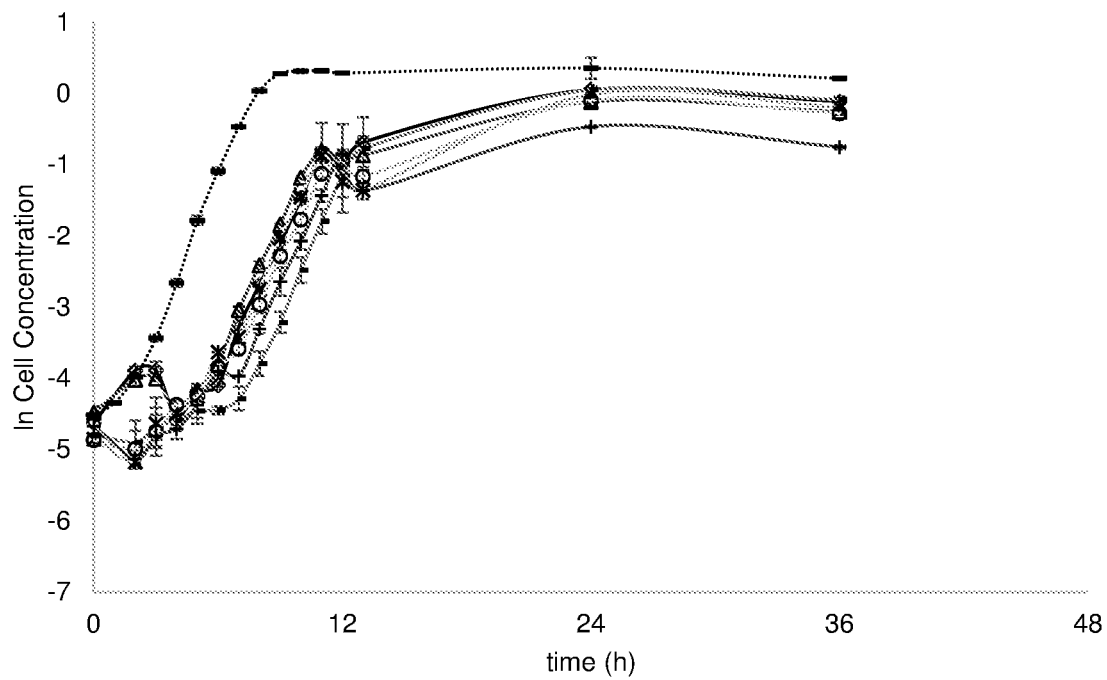
Figure 5I:
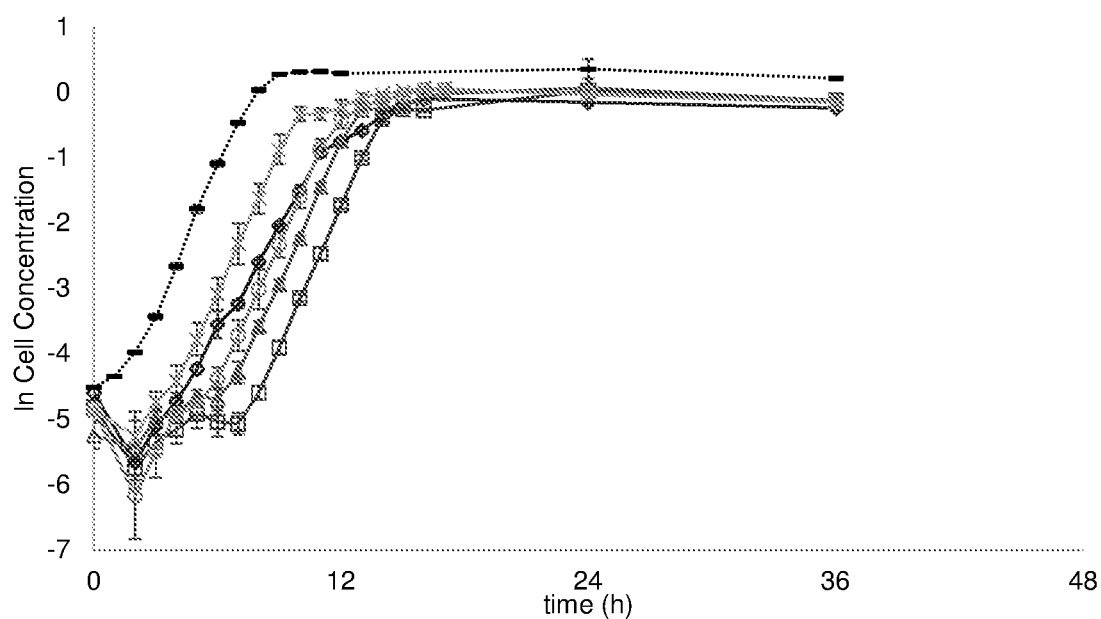
Figure 5J:
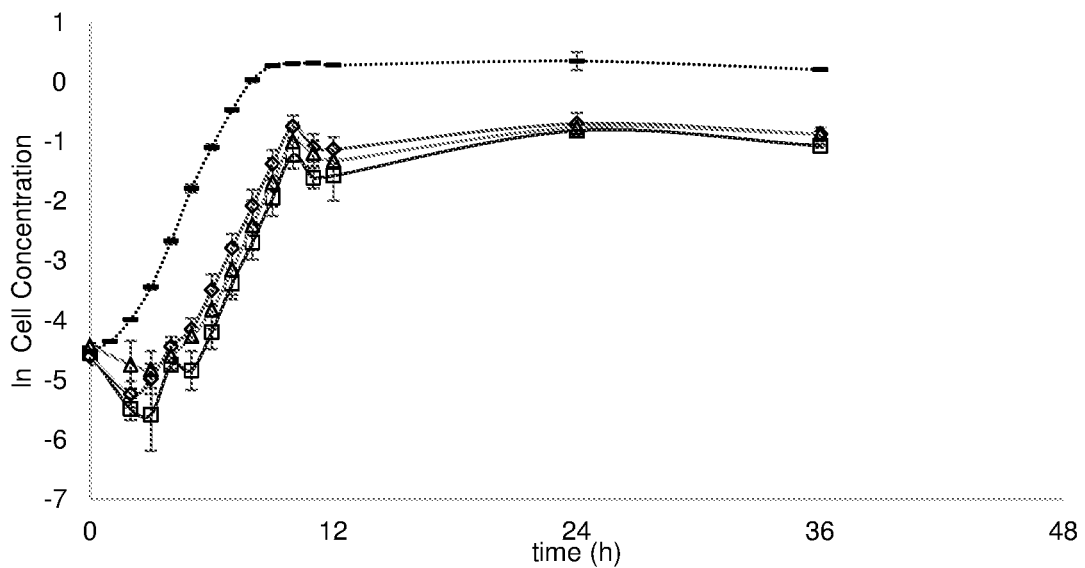
Figure 5K:
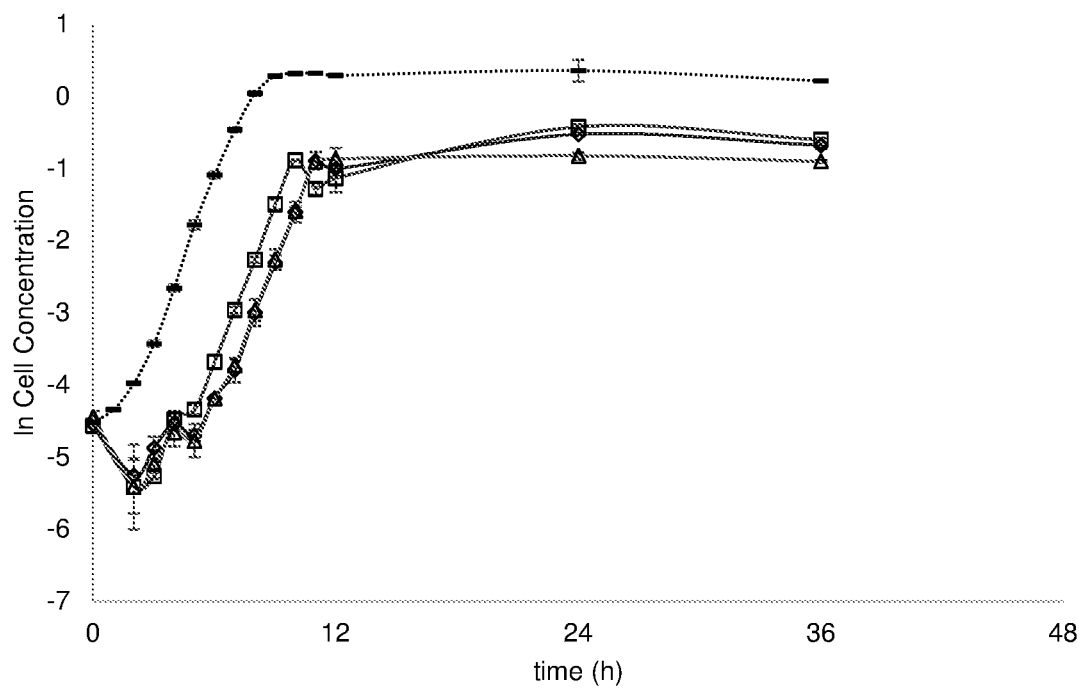

The fourth adaptive evolution experiment was achieved using a chemostat culture (ADE-4; FIG. 5g). The BMA concentration was gradually increased in a step-wise manner from 0 to 20% v/v at a constant dilution rate. After attaining a stable cell concentration at 20% v/v BMA, the dilution rate of the culture was adjusted between 0.33 h$^{-1}$ and 0.55 h$^{-1}$ with the BMA concentration kept constant at 20% v/v.

After the adaptive evolution experiments, an aliquot of the surviving culture was plated into LB agar and a number (at least 6) individual colonies were picked and regrown in liquid media to save stock cultures of each isolated strain. In order to evaluate and compare how BMA affects the growth of each of the isolated strains, their growth kinetics in the presence of 20% v/v BMA were determined. The standard growth conditions used in the determination of strain growth kinetics was a starting optical density (O.D.) of ~0.025 in 50 mL of M9 medium containing 10 g L$^{-1}$ glucose and 20% v/v BMA in a 250 mL conical flasks fitted with suba-seals at 37° C. and 200 rpm using a shaker incubator. Growth was monitored by measuring its O.D. for 36 hours and samples were taken every hour for the first 13-18, 24 and 36 hours after inoculation. A summary of the cell growth kinetic parameters of the isolated strains are listed in Table 2.2. The growth curves of the isolated strains are also shown in FIG. 5.

| Strain; % BMA (v/v) | Max cell concentration (g L$^{-1}$) | Growth rate (h$^{-1}$) | Lag time (h) |
| --- | --- | --- | --- |
| Wild Type; 0 | 1.436 ± 0.213 | 0.728 ± 0.011 | 2 |
| Wild Type; 0.05 | 1.269 ± 0.074 | 0.517 ± 0.014 | 4 |
| Wild Type; 0.1 | 1.335 ± 0.074 | 0.519 ± 0.010 | 12 |
| 2$^a$-rob(R156H) rpoC(L361R) ilvN(C41Y) ygbK(A294E) IpxM(168_185del) | 0.651 ± 0.052 | 0.532 ± 0.028 | 6 |
| 3$^b$-rob(R156H) ilvN(C41Y) phoP(L11F) acrB(V448L) acrR(indels) | 0.790 ± 0.076 | 0.566 ± 0.010 | 4 |
| 5$^c$-soxR(Leu139X), 580116(G > T) acrR(indels) | 0.597 ± 0.096 | 0.625 ± 0.052 | 5 |
| 6$^c$-soxR(A146del), acrR(indels) | 0.588 ± 0.029 | 0.620 ± 0.029 | 4 |

-continued

| Strain; % BMA (v/v) | Max cell concentration (g L$^{-1}$) | Growth rate (h$^{-1}$) | Lag time (h) |
|---|---|---|---|
| 7$^c$-rob(A70V) acrR(indels) | 0.568 ± 0.050 | 0.613 ± 0.033 | 4 |
| 8$^e$-rob(R156H) rpoB(T1037P) torY(A87T) acrR(49Yfs) | 0.435 ± 0.010 | 0.712 ± 0.015 | 5 |
| 18$^d$-rob(A70T)yohJ(L109R) dnaK(V377G) 927777(C > T) acrR(A191fs) | 1.036 ± 0.046 | 0.709 ± 0.015 | 5 |
| 19$^f$-marR(V84G) rpoC(R1075C) ompR(R15S) acrB(T3791) acrR(indels) | 0.653 ± 0.023 | 0.701 ± 0.007 | 5 |
| 20$^f$-marR(V84G) rpoC(R1075C) ompR(R15S) acrR(indels) | 0.589 ± 0.012 | 0.719 ± 0.041 | 5 |
| 21$^f$-marR(V84G) rpoC(R1075C) rpoC(A787V) ompR(R15S) acrB(V901I) acrR(indels) | 0.438 ± 0.022 | 0.703 ± 0.030 | 5 |
| 22$^g$-rob(R156H) rpoB(T1037P) groL(P279L) acrR(49Yfs) 1197659(C > A) | 0.523 ± 0.024 | 0.701 ± 0.015 | 4 |
| 23$^g$-soxR(R20L) rpoC(r1075C) 2133236( T> A) 3915915(T > G) acrR(indels) | 0.529 ± 0.023 | 0.722 ± 0.019 | 4 |

Source of strains: $^a$= FIG. 5.2,
$^b$= ADE-1,
$^c$= ADE-2,
$^d$= ADE-3
$^e$= ADE-4.
$^f$ to $^g$ were taken from ADE-4 at different dilution rates (h1), where $^f$ = 0.46 and $^g$ = 0.54.
NCBI Reference Sequence: NZ_CP009273.1

The genomic DNA sequences of various BMA tolerant strains generated from ADE-1, ADE-2, ADE-3 and ADE-4 were analysed and compared with reference to the parental strain E. coli BW25113 (Tables 2.3, 2.4, and 2.55). Genomic DNA samples for DNA sequencing were prepared from overnight cultures of selected isolates in LB broth using the GeneElute™ Bacterial Genomic DNA Kit with Tris-HCl (10 mM; pH=7.5) as the eluent. The DNA sequence was analyzed using MiSeq v2 150PE (Illumina®) to yield at least 11M+11M reads per run. Reads were trimmed to a minimum length of 36 for quality at the 3' end with a threshold of 30 and adapter sequences of the Nextera XT kit (SEQ ID NO. 33: CTGTCTCTTATA) using Cutadapt version 1.12. Genome alignment and variant calling were undertaken with the Snippy pipeline to identify the difference in genomic DNA sequence between the isolated strains and parental strain/reference genome (Escherichia coli strain BW25113, assembly ASM75055v1, annotation version 34 from Ensembl). Snippy version 3 was used with a minimum of 10 reads covering each position, and 0.9 as the minimum fraction of the reads that must differ from the reference.

TABLE 2.3

Summary of changes in the genomic DNA of the BMA tolerant isolates from various batch culture adaptive evolution encoding gene expression regulatory proteins.

| Gene | Gene Description (Uniprot) | Cellular Location | Genomic Coordinate (NCBI Reference Sequence: NZ_CP009273.1) | Nucleotide Mutation Before → After | Effect of Nucleotide change; Length of Amino Acid Sequence | Strain |
|---|---|---|---|---|---|---|
| rpoB | RNA polymerase β subunit | Cyt | 4174281 | A → C | missense - Thr1037Pro ; 1342 | 8 |
| rpoC | RNA polymerase β' subunit | Cyt | 4174281 | T → G | missense - Leu361Arg ; 1407 | 2 |
| rpoC | RNA polymerase β' subunit | Cyt | 4177637 | C → T | missense - Ala787Val; 1407 | 21 |
| rpoc | RNA polymerase β' subunit | Cyt | 4178500 | C → T | missense - Arg1075Cys ; 1407 | 19, 20, 21,23 |
| rob | Right origin binding protein | Cyt | 4624661 | C → T | missense - Arg156His ; 289 | 2, 3, 8,22 |
| rob | Right origin binding protein | Cyt | 4624919 | G → A | missense - Ala70Val ; 289 | 7 |
| rob | Right origin binding (rob) protein | Cyt | 4624920 | C → T | missense - Ala70Thr ; 289 | 18 |
| rob | Right origin binding (rob) protein | Cyt | 4625592 | C → T | silent - Val85Val; 289 | 18 |
| SOXR | Superoxide response regulon activator | Cyt | 4267455 | G → T | Missense- Arg20Leu; 154 | 23 |

TABLE 2.3-continued

Summary of changes in the genomic DNA of the BMA tolerant isolates from various batch culture adaptive evolution encoding gene expression regulatory proteins.

| Gene | Gene Description (Uniprot) | Cellular Location | Genomic Coordinate (NCBI Reference Sequence: NZ_CP009273.1) | Nucleotide Mutation Before → After | Effect of Nucleotide change; Length of Amino Acid Sequence | Strain |
|---|---|---|---|---|---|---|
| SOXR | Superoxide response regulon activator | Cyt | 4267812 | T → A | Truncation- stops at Leu139 ; 154 | 5 |
| SOXR | Superoxide response regulon activator | Cyt | 4267830 | 3 bp Deletion | Removal of Ala146 without changing the succeeding sequence ; 154 | 6 |
| marR | Multiple antibiotic resistance (mar) operon - repressor protein | Cyt | 1613627 | G → A | Missense-Val84Gly ; 144 | 19, 20, 21 |
| acrR | acriflavine resistance regulator- acrAB operon repressor | Cyt | 481361 | 11 bp deletion | change in amino acid sequence starting at position 53 ; 215 | 8 |
| acrR | acriflavine resistance regulator- acrAB operon repressor | Cyt | | Frameshift | Frameshift at position 49 Y | 8, 22 |
| acrR | acriflavine resistance regulator- acrAB operon repressor | Cyt | | Frameshift | Frameshift at position 191 | 8 |
| acrR | acriflavine resistance regulator -acrAB operon repressor | Cyt | | Indels | Unknown | 2, 3, 5, 6, 7, 19, 20, 21,23 |
| ompR | Outer membrane porin protein - activator | Cyt | 3529901 | G → T | missense - Arg15Ser ; 239 | 19, 20, 21 |
| phoP | Magnesium starvation regulon- regulator | Per | 1185871 | C → A | missense - Leu11Phe ; 223 | 3, |

Notes:
Cellular Location; Cyt- Cytoplasm, Per- Periplasm, IM- Inner Membrane, Uk- Unknown

TABLE 2.4

Summary of changes in the genomic DNA of the BMA tolerant isolates from various batch culture adaptive evolution encoding non-regulatory functional proteins.

| Gene | Gene Description (Uniprot) | Cellular Location | Genomic Coordinate (NCBI Reference Sequence: NZ_CP009273.1) | Nucleotide Change/ Mutation Before → After | Effect of Nucleotide change; Length of Amino Acid Sequence | Strain |
|---|---|---|---|---|---|---|
| acrB | Part of the acrAB-tolC multi-drug efflux complex | IM | 478518 | C → A | missense - Val448Leu ; 1049 | 3 |
| acrB | Part of the acrAB-tolC multi-drug efflux complex | IM | 477159 | C → T | missense - Thr379Ile ; 1049 | 19, 21 |
| yohJ | Membrane protein | IM | 2224428 | T → G | missense - Leu109Arg; 132 | 18 |
| tory | N-oxide and S-oxide reductase subunit | IM | 1952131 | C → T | missense - Ala87Thr ; 366 | 8 |
| IpxM | Myristoyl-acyl carrier protein dependent acyltransferase | IM | 1933628 | 20 bp deletion | change in amino acid sequence starting at position 275; | 2 |

TABLE 2.4-continued

Summary of changes in the genomic DNA of the BMA tolerant isolates from various batch culture adaptive evolution encoding non-regulatory functional proteins.

| Gene | Gene Description (Uniprot) | Cellular Location | Genomic Coordinate (NCBI Reference Sequence: NZ_CP009273.1) | Nucleotide Change/ Mutation Before → After | Effect of Nucleotide change; Length of Amino Acid Sequence | Strain |
|---|---|---|---|---|---|---|
| dnak | Molecular chaperone (HSP70) | Cyt | 13292 | T → G | 323 missense - Val377Gly ; 638 | 18 |
| groL | Chaperonin groEL (HSP60) | Cyt | 4361677 | C → T | missense - Pro279Leu ; 548 | 22 |
| ilvN | Acetolactate synthase isozyme 1 small subunit - Activity regulator | Cyt | 3844331 | C → T | missense - Cys41Tyr ; 96 | 2,3 |
| ygbK | Conserved protein - unknown function | Uk | 2856574 | C → A | missense - Ala294Glu ; 388 | 2 |

Notes:
Cellular Location; Cyt- Cytoplasm, Per- Periplasm, IM- Inner Membrane, Uk- Unknown

TABLE 2.5

Summary of changes in the genomic DNA of the BMA tolerant isolates from various batch culture adaptive evolution in non-coding regions.

| Gene | Gene Description (Genome Viewer) | Cellular Location | Genomic Coordinate (NCBI Reference Sequence: NZ_CP009273.1) | Nucleotide Change/ Mutation Before → After | Effect of Nucleotide change; Length of Amino Acid Sequence | Strain |
|---|---|---|---|---|---|---|
| +230 appY and +19 ompT | Unknown | Uk | 580116 | G → T | unknown | 5 |
| −271 lrp and −274 trxB | unknown | Uk | 927777 | C → T | unknown | 18 |
| +45 cohE and −120 ymfJ | Unknown | Uk | 1197659 | C → A | unknown | 22 |
| +4 asmA and +270 yegH | Unknown | Uk | 2133236 | T → A | unknown | 23 |
| −115 atpI and +502 rsmG | Unknown | Uk | 3915915 | T → G | unknown | 23 |

Notes:
Cellular Location; Cyt- Cytoplasm, Per- Periplasm, IM- Inner Membrane, Uk- Unknown indels- insertion or deletion As can be inferred from Table 2.3 and Table 2.4, each strain had a mutation in acrR. Furthermore, each strain further had a mutation in one of soxR, marR or rob.

Example 3—Transcriptomic Data

Transcriptome analysis was carried out to characterize transcriptional activity in mutant microorganisms using standard methods.

RNA Extraction Protocol
Material:
RNeasy Protect Bacteria Mini kit (50)—Qiagen 74524
RNase-Free DNase Set (50)—Qiagen 79254
RNaseZAP—Cleaning agent for removing Rnase—Sigma-Aldrich R2020-250ML
RNase free eppenfords and 15 ml falcon tubes
RNase free tips
Perform all the extraction in a RNase free "environment", clean everything with RNaseZAP, always use gloves and change gloves frequently.

1. MSX Medium

To prepare 1 L:
Vishniac Trace Elements
Combine EDTA disodium salt (50 g) with water (800 ml), dissolved by adding KOH pellets (2-3 at a time). Add chemicals in the following order; $ZnSO_4$ (2.2 g), $CaCl_2$ (5.54 g), $MnCl_2 \cdot 4H_2O$ (5.06 g), $FeSO_4 \cdot 7H_2O$ (5 g), $(NH_4)_6MO_7O_{24} \cdot 4H_2O$ (1.1 g), $CuSO_4 \cdot 5H_2O$ (1.57 g) and $CoCl_2 \cdot 6H_2O$ (1.61 g).
Adjust to pH 6 using 1M KOH, make up to 1 L using water and store at 4° C. until use.

MSA
$KH_2PO_4$ (6 g) and Vishniac trace elements (2 ml) in water (700 ml)
Adjust to pH 7 using 1M KOH. Make up to 760 ml with water.

MSB
$NH_4Cl$ (3 g) and $MgSO_4 \cdot 7H_2O$ (0.4 g) in water (200 ml).
Sterilize MSA and MSB, then mix and add 40 mL of a stock solution of 12.5% glucose. To make a total 1 L of MSX.

2. Sample Preparation

1) Streak strains onto fresh MSX agar (15 g/L) plates directly from the cryostocks and incubate overnight at 37° C.
2) Isolate single colonies and inoculate pre-cultures in MSX, using 50 ml shake flasks. Incubate overnight at 37° C. and 250 rpm.
3) Inoculate cultures in MSX to an initial OD600 of 0.05, using 250 mL pyrex shake flasks with 24/29 neck join. Incubate at 37° C. and 250 rpm. Do 4 biological replicates (3 replicates for sequencing plus one backup)—4 flasks per strain.
4) Seal shake flasks with sterile Suba seals. To monitor OD, take samples using a sterile syringe and needle after first swabbing the Suba seals with 70% ethanol. Monitor OD.
5) When OD reaches 0.3, collect first sample for RNA extraction ("before" sample) into a pre-chilled falcon. Keep samples on ice.
6) Immediately after, add 20% (v/v) BMA. Re-incubate cultures.
7) Quickly process the samples according to the RNeasy kit protocol, until step 6 of protocol 1. Always keep samples on ice and store it at −80° C. until further use, if possible, flash freeze in liquid nitrogen it before storing.
8) One hour after the first sample collection/BMA addition, collect the second sample for RNA extraction ("after" sample). Proceed as explained before.
9) Continue to monitor the OD until the cultures reach 24 h.

To summarise, each strain tested will have 6 samples to send for sequencing, 3 collected right before the addition and 3 collected one hour after, plus 1 "back-up" for before and after, in case something goes wrong during extraction (8 samples total). Besides the WT strain with the addition of BMA, samples were also collected from a WT culture with no BMA, one hour after reaching OD of 0.3, as a control.

3. RNA Extraction

Proceed according to the RNeasy kit instructions. Protocol 1 and 7—for Gram-negative bacteria grown on minimal media—plus appendix B "On-Column DNase Digestion Using the RNase-Free DNase Set".

Separate final sample into 3 aliquots. Use only one aliquot to check concentration and if there are gDNA contaminations. Do not use this aliquot for sequencing, as thawing and freezing the samples can degrade the RNA.

Check RNA Concentration and RIN Numbers Using TapeStation.

Transcription was compared for a double mutant and the wild-type in the presence and absence of BMA relative to the level in the wild type in the absence of BMA. For the avoidance of doubt the level in the table is the ratio of the level in the strain under the BMA exposure relative to the level in the wild type in the absence of added BMA. Levels of transcription of acrA and acrB were enhanced in the absence of BMA, however this was very variable. For the wild type strain, exposure to BMA actually reduces the expression level of the global regulator. This demonstrates that the principal multi drug resistance pump is strongly over expressed in these strains. The results are shown in Table 2.6 below.

TABLE 2.6

| | acrAB gene expression | | | | | | |
|---|---|---|---|---|---|---|---|
| | LM double mutant | 2 | 5 | 18 | 21 | 22 | 23 | wild type |
| Transcriptomics without BMA added vs wild type | | | | | | | | |
| acrA | 6.88 | 2.81 | 7.54 | 16.98 | 0.75 | 8.31 | 2.49 | |
| acrB | 6.89 | 3.71 | 7.13 | 3.12 | 2.02 | 3.81 | 4.80 | |
| Transcriptomics with added BMA vs wild type without BMA | | | | | | | | |
| acrA | 5.13 | 7.33 | 6.28 | 6.47 | 5.63 | 7.44 | 6.50 | 0.64 |
| acrB | 4.99 | 6.68 | 7.49 | 10.12 | 8.93 | 7.17 | 7.66 | 0.98 |

The transcription levels of some key genes was enhanced or reduced strongly by BMA. The "top 27" enhancements with BMA relative to BW25113 without BMA exposure are shown in the table 2.7. For comparison, the same genes without exposure to BMA are shown in table 2.8. Transcription was compared for a double mutant and the wild-type in the presence and absence of BMA relative to the level in the wild type in the absence of BMA. For the avoidance of doubt the level in the table is the ratio of the level in the strain under the BMA exposure relative to the level in the wild type in the absence of added BMA.

There was no consistent trends for transcription levels in the case where BMA is not fed. In the presence of BMA,

TABLE 2.7

Transcriptomic data of the double mutant compared with wild-type and 6 other strains, with added BMA.

| | double mutant | 2 | 5 | 18 | 21 | 22 | 23 | wild type |
|---|---|---|---|---|---|---|---|---|
| ibpB | 672.54 | 84.03 | 174.50 | 158.35 | 30.97 | 107.99 | 41.67 | 0.42 |
| asr | 711.06 | 95.27 | 160.42 | 74.22 | 11.63 | 225.15 | 123.20 | 0.22 |
| yhjx | 2.32 | 7.35 | 105.59 | 251.44 | 3.11 | 902.70 | 596.44 | 1.72 |
| ydgU | 188.87 | 31.80 | 48.46 | 28.47 | 6.39 | 94.74 | 50.45 | 7.95 |
| narG | 3.23 | 11.38 | 47.85 | 25.46 | 65.34 | 61.85 | 42.52 | 0.40 |
| ibpA | 80.35 | 20.83 | 43.39 | 74.55 | 29.21 | 70.31 | 31.35 | 0.09 |
| soxS | 20.93 | 4.10 | 41.81 | 1.17 | 1.08 | 3.66 | 30.40 | 0.24 |
| ynfM | 29.92 | 14.42 | 40.65 | 55.40 | 65.39 | 61.15 | 41.92 | 0.07 |
| nirB | 3.28 | 8.77 | 34.19 | 23.98 | 39.43 | 20.40 | 25.46 | 0.06 |
| yibT | 43.57 | 36.87 | 29.57 | 83.81 | 95.47 | 77.30 | 42.63 | 0.09 |
| adiY | 10.80 | 5.37 | 24.79 | 21.13 | 10.74 | 23.19 | 6.73 | 0.19 |
| pspA | 27.60 | 15.40 | 23.32 | 20.71 | 21.16 | 47.39 | 32.81 | 0.04 |
| ariR | 8.91 | 35.30 | 21.79 | 25.19 | 6.13 | 12.95 | 14.82 | 0.44 |
| spy | 99.47 | 22.92 | 20.88 | 4.36 | 1.77 | 45.77 | 4.79 | 3.91 |
| bssR | 5.47 | 15.30 | 20.35 | 134.14 | 198.48 | 71.24 | 71.61 | 0.46 |
| ybfA | 59.92 | 18.45 | 20.19 | 24.95 | 33.06 | 36.33 | 29.99 | 0.39 |
| raiA | 36.36 | 14.09 | 20.11 | 44.16 | 22.55 | 52.61 | 31.13 | 0.11 |
| ybhG | 10.78 | 6.87 | 18.33 | 18.85 | 9.26 | 21.92 | 20.82 | 0.19 |
| ldhA | 30.42 | 11.32 | 18.24 | 56.74 | 20.48 | 25.80 | 28.20 | 0.59 |
| ymgC | 11.68 | 42.36 | 17.15 | 12.62 | 1.53 | 5.45 | 7.42 | 6.27 |
| pspB | 11.73 | 11.46 | 16.87 | 20.94 | 14.98 | 35.43 | 27.16 | 0.73 |
| nirD | 3.57 | 4.33 | 16.69 | 34.98 | 42.50 | 26.97 | 25.17 | 0.57 |
| pspc | 11.09 | 11.88 | 16.55 | 21.37 | 14.67 | 39.73 | 28.45 | 0.10 |
| ymgA | 9.97 | 35.59 | 16.41 | 11.97 | 2.43 | 6.44 | 8.84 | 0.16 |
| yohk | 19.51 | 8.45 | 16.04 | 14.54 | 7.09 | 19.75 | 10.04 | 0.13 |
| rmf | 17.63 | 7.05 | 15.45 | 20.96 | 36.77 | 17.43 | 8.80 | 0.28 |
| ybiH | 7.73 | 8.65 | 15.30 | 12.75 | 7.20 | 16.75 | 16.75 | 0.04 |
| pspD | 10.00 | 11.22 | 14.10 | 18.60 | 14.80 | 38.90 | 28.18 | 0.14 |

TABLE 2.8

Transcriptomic data of the double mutant compared with wild-type and 6 other strains, without added BMA.

| | double mutant | 2 | 5 | 18 | 21 | 22 | 23 |
|---|---|---|---|---|---|---|---|
| | Transcriptomics without BMA added vs wild type | | | | | | |
| ibpB | 0.76 | 0.53 | 1.12 | 1.35 | 0.36 | 0.81 | 0.75 |
| asr | 1.45 | 0.89 | 1.54 | 1.16 | 6.45 | 0.92 | 0.71 |
| yhjx | 0.52 | 0.66 | 0.75 | 0.73 | 0.59 | 0.70 | 1.01 |
| ydgU | 0.51 | | 0.86 | 0.54 | 1.30 | 0.44 | 0.74 |
| narG | 6.67 | 0.84 | 4.48 | 25.35 | 42.79 | 1.06 | 6.33 |
| ibpA | 0.74 | 0.74 | 0.86 | 1.11 | 0.21 | 0.58 | 0.79 |
| soxS | 48.09 | 0.82 | 31.44 | 0.43 | 2.23 | 0.51 | 32.04 |
| ynfM | 1.43 | 0.94 | 1.07 | 4.08 | 7.33 | 1.36 | 1.23 |
| nirB | 13.77 | 0.70 | 5.79 | 35.54 | 24.66 | 4.25 | 10.18 |
| yibT | 0.82 | 6.72 | 0.81 | 1.39 | 2.51 | 4.87 | 0.50 |
| adiY | 0.91 | 0.80 | 0.96 | 1.88 | 2.19 | 2.11 | 1.11 |
| pspA | 0.27 | 0.61 | 0.53 | 0.11 | 0.53 | 0.25 | 0.47 |
| ariR | 0.92 | 2.82 | 2.09 | 2.65 | 0.21 | 0.62 | 0.56 |
| spy | 0.42 | 0.48 | 0.75 | 0.42 | 0.28 | 0.28 | 0.40 |
| bssR | 2.52 | 1.08 | 1.48 | 4.39 | 43.23 | 4.43 | 3.69 |
| ybfA | 1.27 | 1.03 | 1.29 | 0.91 | 3.08 | 1.57 | 1.27 |
| raiA | 1.06 | 0.77 | 0.81 | 1.49 | 5.91 | 0.89 | 0.84 |
| ybhG | 1.20 | 0.83 | 1.19 | 0.37 | 0.78 | 0.28 | 0.33 |
| ldhA | 1.18 | 0.78 | 1.13 | 0.92 | 0.90 | 0.95 | 1.09 |
| ymgC | 0.74 | 3.06 | 2.04 | 1.86 | 0.26 | 1.11 | 0.57 |
| pspB | 0.28 | 0.59 | 0.47 | 0.09 | 0.30 | 0.25 | 0.45 |
| nirD | 22.13 | 0.78 | 9.18 | 54.68 | 45.97 | 3.30 | 16.04 |
| pspc | 0.29 | 0.59 | 0.46 | 0.08 | 0.18 | 0.23 | 0.44 |
| ymgA | 0.57 | 2.99 | 2.16 | 2.47 | 0.35 | 0.86 | 0.74 |
| yohK | 1.02 | 1.20 | 1.08 | 0.88 | 1.94 | 1.64 | 0.97 |
| rmf | 1.54 | 1.07 | 1.31 | 1.50 | 4.53 | 1.14 | 0.50 |
| ybiH | 1.21 | 0.93 | 1.05 | 0.46 | 0.69 | 0.54 | 0.61 |
| pspD | 0.28 | 0.58 | 0.48 | 0.08 | 0.12 | 0.21 | 0.40 | ibpA, ibpB, ynfM, yibT, pspA, bssR, ybfA, raiA, ldhA, pspB pspC and pspD are all enhanced by greater than x10 in the strains, but all are reduced in the wild type strain. In the absence of BMA none of ibpA, ibpB, ynfM, yibT, pspA, bssR, ybfA, raiA, ldhA, pspB and pspC were enhanced in the strains. The functions of these genes are listed in Table 2.9.

TABLE 2.9 functions of the genes that were not enhanced when BMA was not fed to cultures.

| gene | function |
|---|---|
| IbpA | heat shock chaperone(ibpA) |
| IbpB | heat shock chaperone(ibpB) |
| pspA | regulatory protein for phage-shock-protein operon(pspA) |
| pspB | Phage shock protein operon transcription co-activator(pspB) |
| pspc | Phage shock protein operon transcription co-activator(pspC) |
| pspD | Phage shock protein operon transcription co-activator(pspD) |
| raiA | cold shock protein associated with 30S ribosomal subunit(raiA) |
| ynfM | putative arabinose efflux transporter(ynfM) |
| yibT | uncharacterized protein(yibT) |
| bssR | repressor of biofilm formation by indole transport regulation (bssR) |
| ybfA | DUF2517 family protein(ybfA) |
| ldhA | fermentative D-lactate dehydrogenase, NAD-dependent(ldhA) |

The invention claimed is:

1. A method for the production of a methacrylate comprising
   a) providing a genetically modified microorganism with increased tolerance to a $C_3$-$C_{12}$ methacrylate ester compared to the wild type microorganism in a fermentation medium and
   b) growing the microorganism under conditions whereby a $C_3$-$C_{12}$ methacrylate ester is produced;
   wherein the microorganism is *E coli;*
   wherein the genetically modified microorganism comprises a mutation in a wild type soxR nucleic acid sequence;
   wherein the wild type soxR nucleic acid sequence comprises SEQ ID NO. 1 or a homologue thereof, and
   wherein the mutant soxR nucleic acid sequence encodes a mutant SoxR protein comprising R20 substituted with H.

2. The method according to claim 1 wherein the microorganism is tolerant to at least 20% v/v $C_3$-$C_{12}$ methacrylate ester when grown in a liquid medium at about 37° C.

3. The method according to claim 1 wherein the genetically modified microorganism further comprises a mutation in one or more of:
   an acrR nucleic acid sequence comprising SEQ ID NO. 3 or a homologue thereof, a rob nucleic acid sequence comprising SEQ ID NO. 5 or a homologue thereof, a marR nucleic acid sequence comprising SEQ ID NO. 7 or a homologue thereof.

4. The method according to claim 3, wherein the mutant acrR nucleic acid sequence encodes a mutant AcrR protein, and wherein the mutation is selected from one of the following: a substitution of V29 with another amino acid, a frameshift mutation at T32, A191 or position 49 in AcrR.

5. A method for growing or maintaining a microorganism in the presence of a $C_3$-$C_{12}$ methacrylate ester comprising providing a genetically modified microorganism with increased tolerance to a $C_3$-$C_{12}$ methacrylate ester compared to a wild type microorganism in a fermentation medium under conditions whereby a $C_3$-$C_{12}$ methacrylate ester is produced,
   wherein the microorganism is *E coli;*
   wherein the genetically modified microorganism comprises a mutation is in a wild type soxR nucleic acid sequence;
   wherein the wild type soxR nucleic acid sequence comprises SEQ ID NO. 1 or a homologue thereof; and
   wherein the mutant soxR nucleic acid sequence encodes a mutant SoxR protein comprising R20 substituted with H.

6. A fermentation medium comprising a $C_3$-$C_{12}$ methacrylate ester and a genetically modified microorganism with increased tolerance to a $C_3$-$C_{12}$ methacrylate ester compared to a wild type microorganism;
   wherein the microorganism is *E. coli;*
   wherein the genetically modified microorganism comprises a mutation is in a wild type soxR nucleic acid sequence;

wherein the wild type soxR nucleic acid sequence comprises SEQ ID NO. 1 or a homologue thereof; and wherein the mutant soxR nucleic acid sequence encodes a mutant SoxR protein comprising R20 substituted with H.

7. A method for the isolation of a methacrylate tolerant microorganism comprising:
   a) providing a microorganism in a fermentation medium
   b) contacting the microorganism with a methacrylate; and
   c) isolating the viable microorganism of step (b)
   wherein the viable microorganism is tolerant to at least 20% v/v a methacrylate when grown in liquid medium at about 37° C.
   wherein the microorganism is *E coli;*
   wherein the microorganism comprises a mutation in a wild type soxR nucleic acid sequence;
   wherein the wild type soxR nucleic acid sequence comprises SEQ ID NO. 1 or a homologue thereof; and
   wherein the mutant soxR nucleic acid sequence encodes a mutant SoxR protein comprising R20 substituted with H.

8. The method according to claim 3, wherein the mutant rob nucleic acid sequence encodes a mutant Rob protein, and wherein the mutation is selected from one of the following: a substitution of A70 or a substitution of R156 with another amino acid in Rob.

9. The method according to claim 3, wherein the mutant marR nucleic acid sequence encodes a mutant MarR protein, and wherein the mutation is a substitution of V84 with another amino acid in MarR.

\* \* \* \* \*

UNITED STATES PATENT AND TRADEMARK OFFICE
CERTIFICATE OF CORRECTION

PATENT NO. : 11,781,160 B2
APPLICATION NO. : 17/057051
DATED : October 10, 2023
INVENTOR(S) : Disley et al.

It is certified that error appears in the above-identified patent and that said Letters Patent is hereby corrected as shown below:

In the Specification

Column 26, Line 54: Please correct "sp2-ketoisovalerate" to read --sp,; 2-ketoisovalerate--

Column 36, Line 50: Please insert the following above the table: --TABLE 2.2 Growth Kinetic Parameters of BMA tolerant strains isolated from various batch and continuous cultures adaptive evolution at 20% v/v BMA.--

Column 39, Table 2.4, 4th Gene entry: Please correct "tory" to read --torY--

Column 41, Table 2.4, 6th Gene entry: Please correct "dnak" to read --dnaK--

Column 45, Table 2.7, 3rd Double Mutant entry: Please correct "yhjx" to read --yhjX--

Column 45, Table 2.7, 23rd Double Mutant entry: Please correct "pspc" to read --pspC--

Column 45, Table 2.7, 25th Double Mutant entry: Please correct "yohk" to read --yohK--

Column 45, Table 2.8, 3rd Double Mutant entry: Please correct "yhjx" to read --yhjX--

Column 45, Table 2.8, 23rd Double Mutant entry: Please correct "pspc" to read --pspC--

Column 46, Table 2.9, 5th Gene entry: Please correct "pspc" to read --pspC--

In the Claims

Column 111, Line 13, Claim 7: Please correct "37° C." to read --37° C.;--

Signed and Sealed this
Twenty-first Day of May, 2024

*Katherine Kelly Vidal*

Katherine Kelly Vidal
*Director of the United States Patent and Trademark Office*